(12) United States Patent
Takinami et al.

(10) Patent No.: US 7,207,952 B2
(45) Date of Patent: Apr. 24, 2007

(54) BODY FLUID COMPOSITION MEASURING APPARATUS

(75) Inventors: Masao Takinami, Kanagawa (JP);
Yoshiaki Yaguchi, Kanagawa (JP);
Kouichi Sonoda, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 392 days.

(21) Appl. No.: 10/333,582

(22) PCT Filed: Jul. 26, 2001

(86) PCT No.: PCT/JP01/06453
§ 371 (c)(1),
(2), (4) Date: Jan. 24, 2003

(87) PCT Pub. No.: WO02/07399
PCT Pub. Date: Jan. 31, 2002

(65) Prior Publication Data
US 2003/0109808 A1    Jun. 12, 2003

(30) Foreign Application Priority Data
Jul. 26, 2000 (JP) ............................ 2000-225936
Aug. 18, 2000 (JP) ............................ 2000-248777
Aug. 18, 2000 (JP) ............................ 2000-248778

(51) Int. Cl.
*A61B 5/00* (2006.01)
*B65D 81/00* (2006.01)
(52) U.S. Cl. .................................................. 600/584
(58) Field of Classification Search ................ 600/573, 600/575–578, 583, 584; 422/56, 82.05, 99–101; 204/403.01; 435/14; 436/180, 148, 169, 436/177
See application file for complete search history.

(56) References Cited

U.S. PATENT DOCUMENTS

| 4,627,445 A | 12/1986 | Garcia et al. |
| 4,637,403 A | 1/1987 | Garcia et al. |
| 5,700,695 A * | 12/1997 | Yassinzadeh et al. ....... 436/180 |

(Continued)

FOREIGN PATENT DOCUMENTS

DE    197 22 934 A1    7/1999

(Continued)

*Primary Examiner*—Max F. Hindenburg
*Assistant Examiner*—Brian Szmal
(74) *Attorney, Agent, or Firm*—Buchanan Ingersoll & Rooney PC

(57) ABSTRACT

A body fluid component measuring apparatus capable of accurately measuring a specific component in a body fluid for a short time includes, in a main body, a measuring device for detecting the sampling of a body fluid and measuring a component of the sampled body fluid, and a pump and an electromagnetic valve which constitute an evacuating mechanism. When the sampling of blood is detected, the pump is stopped to release the evacuation state. Another apparatus according to a second aspect includes a pressure detecting means and a notifying device. A puncturing device is operated only when it is decided on the basis of a result of detection by a sensor, that the housing is in an evacuation state, and after the sampling is detected, the evacuation is released and information is notified. A further apparatus according to a third aspect includes a pressure adjusting means for fluctuating the pressure.

38 Claims, 34 Drawing Sheets

U.S. PATENT DOCUMENTS

| | | | |
|---|---|---|---|
| 6,093,156 A | 7/2000 | Cunningham et al. | |
| 6,206,841 B1 * | 3/2001 | Cunningham et al. | 600/584 |
| 2002/0168290 A1 * | 11/2002 | Yuzhakov et al. | 422/56 |

FOREIGN PATENT DOCUMENTS

| | | |
|---|---|---|
| EP | 0 931 507 A1 | 7/1999 |
| EP | 0 988 828 A1 | 3/2000 |
| JP | 61-286738 | 12/1986 |
| JP | 10-5200 | 1/1998 |
| JP | 2000-14662 | 1/2000 |
| JP | 2000-152923 A | 6/2000 |
| WO | WO 86/05966 | 10/1986 |

* cited by examiner

F I G. 1
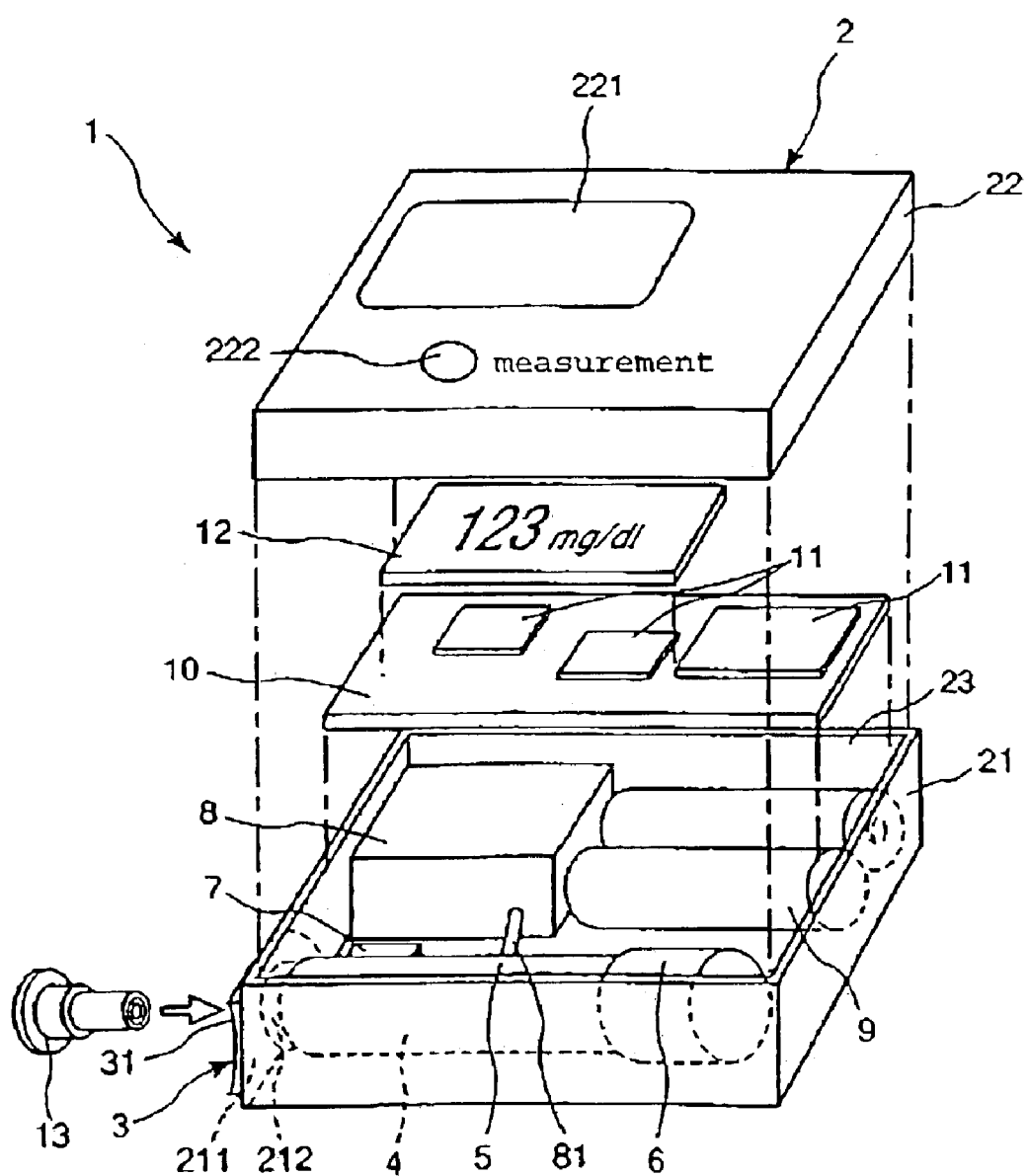

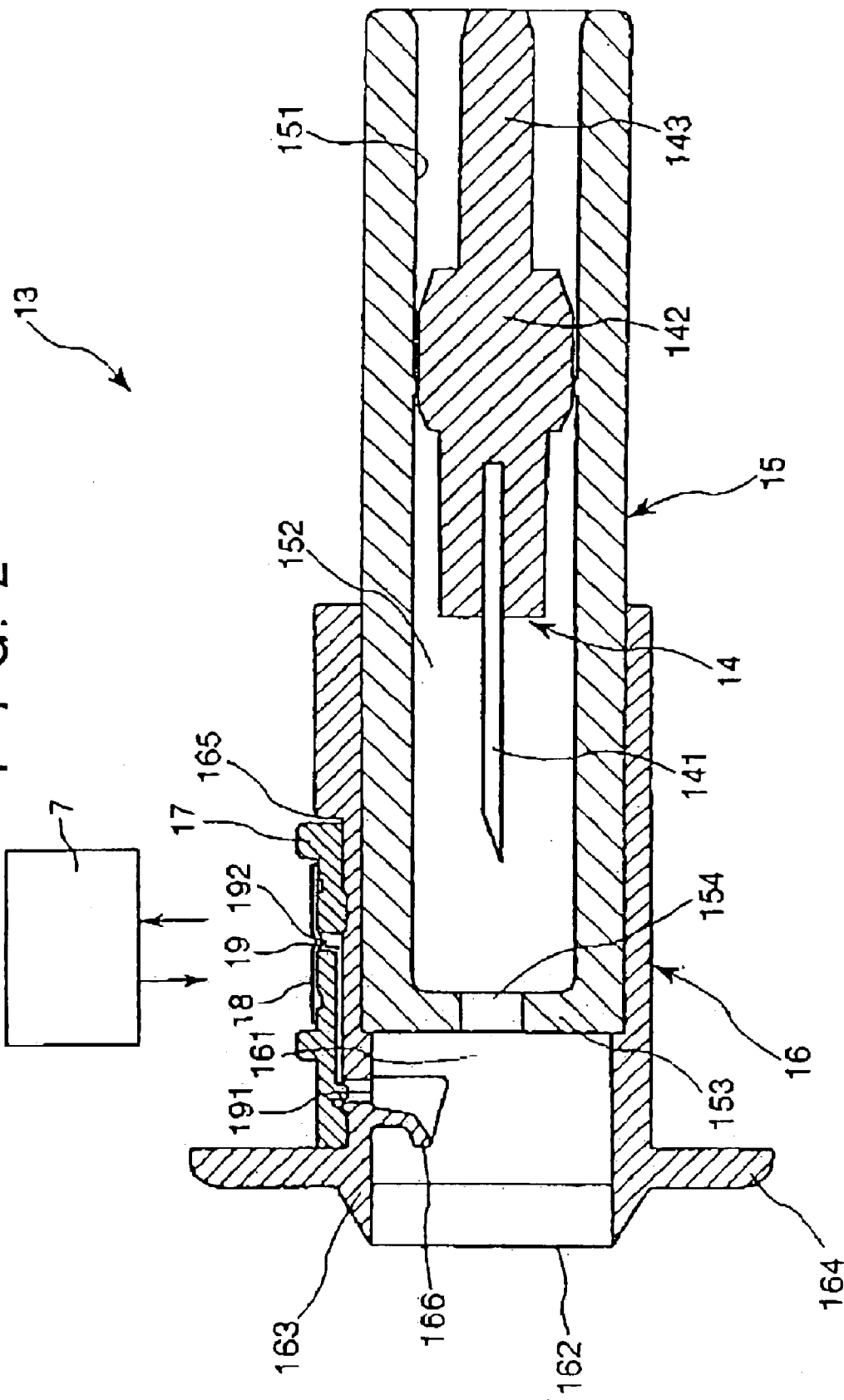

F I G. 2 3
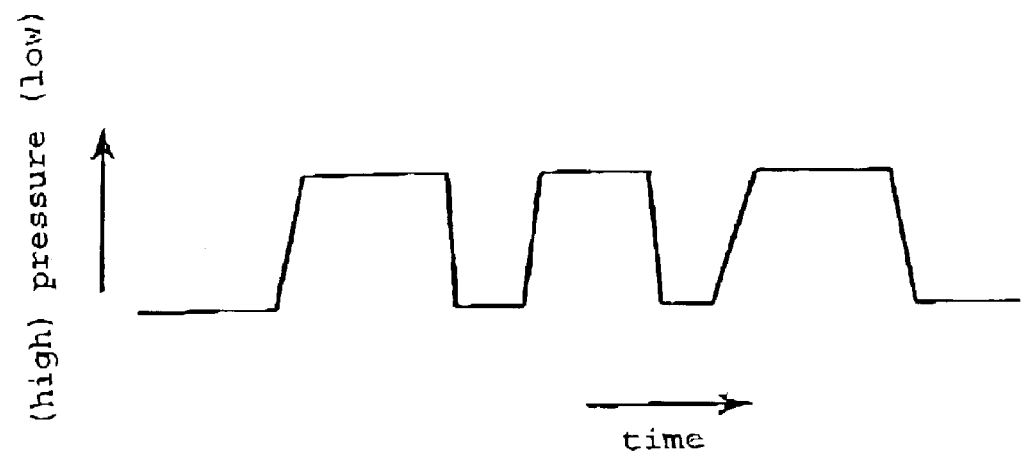
F I G. 2 4
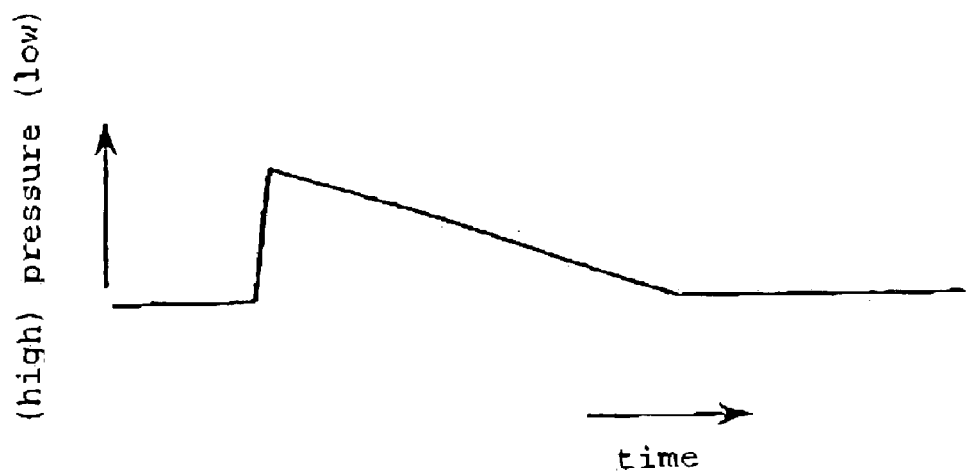

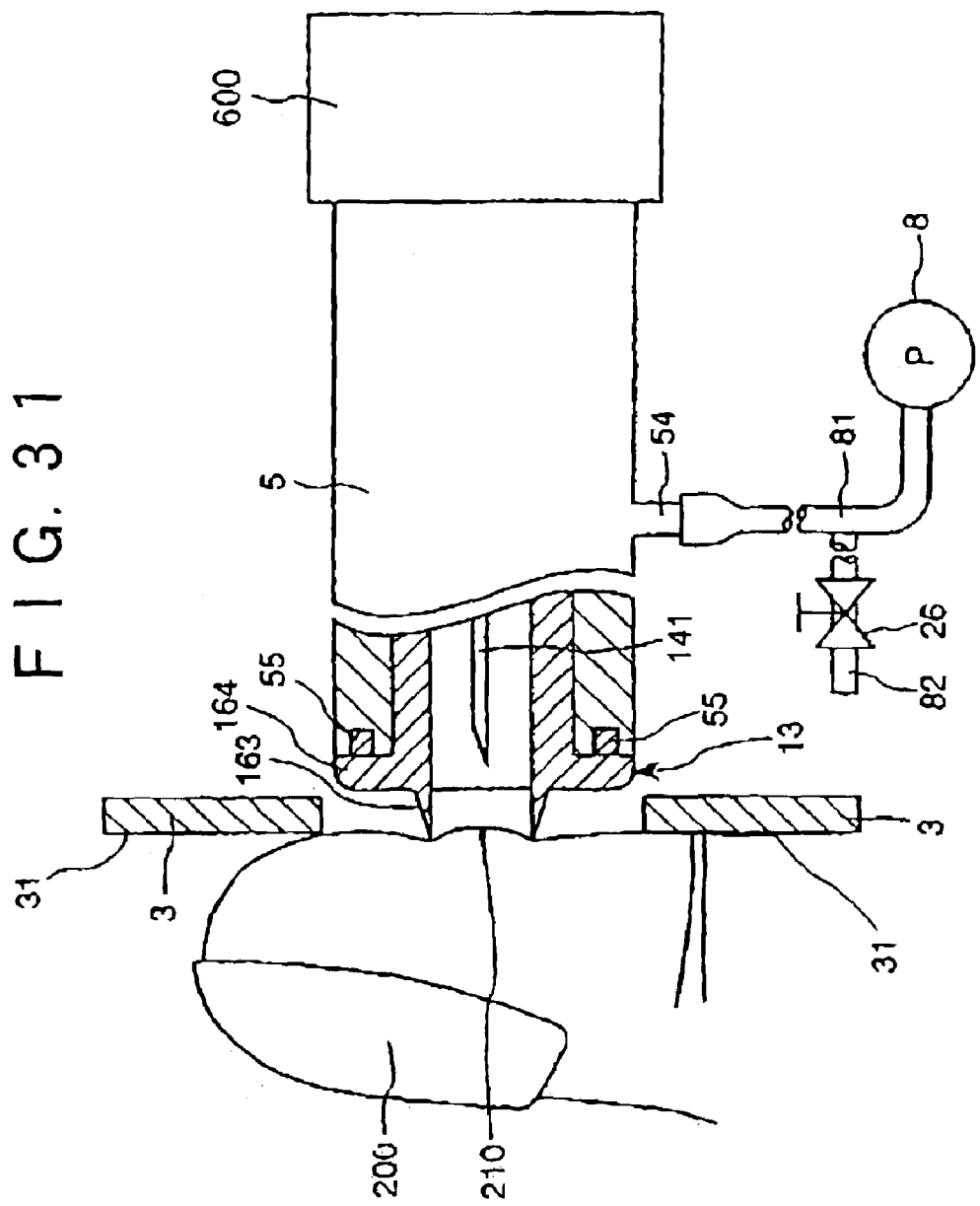
F I G. 31

BODY FLUID COMPOSITION MEASURING APPARATUS

TECHNICAL FIELD

The present invention relates to a body fluid component measuring apparatus, and particularly to a body fluid component measuring apparatus used for inspecting blood by puncturing an epidermis with a puncture needle, sampling blood, and measuring a specific component such as glucose in the blood.

BACKGROUND ART

In recent years, along with the increased number of patients suffering from diabetes, self-monitoring of blood glucose, adapted to allow a patient to daily monitor a variation in blood sugar level of the patient, has come to be recommended.

The measurement of a blood sugar level is performed by using a blood glucose monitoring apparatus in accordance with a manner of mounting a strip of test paper, specified to be colored depending on an amount of glucose in blood, to the apparatus, supplying and diffusing blood to and in the test paper to color the test paper, and optically measuring the degree of coloring of the test paper, thereby quantifying a blood sugar level.

Prior to such measurement, the sampling of blood by a patient is performed by puncturing the skin of an epidermis with a puncture device including a puncture needle or a blade and compressing a portion, around the puncture site, with a finger, for example, so as to squeeze blood therefrom.

A finger tip of a patient is suitable as a portion from which blood is to be sampled because blood capillaries are concentrated at the finger tip; however, since nerves are also concentrated at the finger tip, the puncture of the finger tip may inflict a pain on the patient. The puncture of a finger tip may inflict not only a large bodily pain and a large psychic burden but also a feeling of fear against puncture on a patient, and for this reason, many patients may often fail to continue the self-monitoring of blood glucose.

The prior art monitoring of a blood glucose has a problem in terms of operability because the puncturing operation, the blood sampling operation, and the measuring operation are separately performed.

A blood glucose monitoring apparatus capable of solving such a problem is known in Japanese Patent Application Nos. Hei 10-183794 and Hei 10-330057, which includes a puncturing unit and a measuring unit integrated with each other, and a suction means for squeezing blood.

In operation of the above blood glucose monitoring apparatus, a finger tip is first touched to the tip of a chip so as to air-tightly seal the tip opening.

The finger tip is then punctured with a puncture needle projecting from the tip opening, and in such a state, a sucking means is operated (to cause an evacuation state), to suck blood from a puncture site, thereby sampling the blood. The blood sugar level of the sampled blood is then measured by a measuring unit.

The above blood glucose monitoring apparatus, however, has a problem that since the blood is sucked at a constant pressure, it takes a relatively long time to obtain an amount of blood necessary for measurement of a blood sugar level.

Another problem is that since a gap between the finger and the tip of the chip may occur depending on a position of the finger touched to the tip of the chip, it fails to sufficiently reduce the pressure in spite of the operation of the sucking means, and therefore it fails to obtain an amount of blood necessary for measurement or it takes a relatively long time to obtain a sufficient amount of blood.

One example of a chemical formula between glucose ($_D$-Glucose) in blood and a reagent at the time of measurement of a blood sugar level is shown below, and as is apparent from the chemical formula, a sufficient amount of oxygen is required for measurement of blood sugar level. In other words, if the amount of oxygen is insufficient, it fails to accurately measure a blood sugar level.

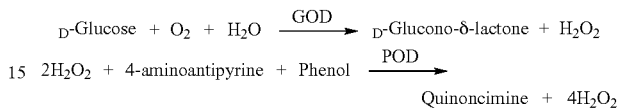

According to the prior art blood glucose monitoring apparatus, however, a blood sugar level may be often measured in the evacuation state, and in this case, there may occur a problem that a blood sugar level cannot be accurately measured because of insufficient amount of oxygen.

To solve such a problem, the present inventor has found that oxygen (component, necessary for measurement, in atmospheric air) can be sufficiently supplied by releasing or relieving the evacuation state prior to measurement, and has accomplished the present invention on the basis of such knowledge.

An object of the present invention is to provide a body fluid component measuring apparatus capable of accurately, certainly measuring a specific component in blood for a short time.

DISCLOSURE OF INVENTION

The above object is achieved by the following configurations (1) to (10) according to a first aspect of the present invention.

(1) A body fluid component measuring apparatus used with a chip mounted thereto, said chip including a puncture needle and a strip of test paper, said apparatus comprising:

a touch portion to which an epidermis to be punctures is touched;

puncturing means for operating said puncture needle so as to puncture the epidermis touched to said touch portion;

evacuating means for evacuating a puncture site of the epidermis to be punctured by said puncture needle as well as a housing space for housing said puncture needle and said test paper;

measuring means for measuring an amount of a specific component of a body fluid sampled from the puncture site and diffused in said test paper;

body fluid sampling detecting means for detecting the sampling of the body fluid; and evacuation releasing means for releasing or relieving the evacuation state of at least said housing space for housing said test paper;

wherein when the sampling of the body fluid is detected by said body fluid sampling detecting means, the evacuation state of at least said housing space for housing said test paper is released or relieved, and then the amount of the specific component in the sampled body fluid is measured by said measuring means.

(2) A body fluid component measuring apparatus described in (1), wherein the measurement of the amount of the specific component in the body fluid requires a specific component in atmospheric air.

(3) A body fluid component measuring apparatus described in (1) or (2), wherein said evacuation releasing means has a flow passage for communicating said housing space to the outside and a valve for opening/closing said flow passage.

(4) A body fluid component measuring apparatus described in (1) or (2), wherein said evacuation releasing means has a flow passage for communicating said housing space to the outside, and at least part of said flow passage has a portion in which an air passing resistance is relatively high.

(5) A body fluid component measuring apparatus described in any one of (1) to (4), wherein at least part of said measuring means and at least part of said body fluid component sampling detecting means are used commonly to each other.

(6) A body fluid component measuring apparatus described in any one of (1) to (5), further comprising a housing for holding said chip and housing said puncturing means, wherein said evacuating means brings said housing space in said housing into an evacuation state.

(7) A body fluid component measuring apparatus described in (6), wherein said evacuation releasing means releases or relives the evacuation state of said housing space in said housing.

(8) A body fluid component measuring apparatus described in any one of (1) to (7), wherein the operation of said puncturing means and the operation of said evacuating means are allowed to be nearly simultaneously started.

According to the first aspect of the present invention, there are further provided a body fluid component measuring apparatus (9) including a pressure detecting means and a notifying means specified in (12) of a second aspect (to be described later), and a body fluid component measuring apparatus (10) including a pressure adjusting means specified in (25) of a third aspect (to be described later).

(9) A body fluid component measuring apparatus described in any one of (1) to (8), further comprising
pressure detecting means for detecting the pressure in said housing space; and
notifying means for notifying specific information;
wherein said housing space are tried to evacuate by said evacuating means, and a notice based on the information from said pressure detecting means is outputted by said notifying means.

(10) A body fluid component measuring apparatus described in any one of (1) to (9), further comprising pressure adjusting means for adjusting the pressure in said housing space for housing said puncture needle.

The above object is achieved by configurations (11) to (21) according to a second aspect of the present invention.

(11) A body fluid component measuring apparatus for sampling a body fluid via an epidermis and measuring a component of the body fluid, said apparatus comprising:
a touch portion to which the epidermis is touched;
a space air-tightly sealed with the epidermis touched to said touch portion;
evacuating means for evacuating said space;
measuring means for measuring an amount and/or a property of a specific component in the body fluid sampled in said space;
pressure detecting means for detecting the pressure in said space; and
notifying means for notifying specific information;
wherein said space is tried to evacuate by said evacuating means, and a notice based on the information from said pressure detecting means is outputted by said notifying means.

(12) A body fluid component measuring apparatus used with a chip mounted thereto, said chip including a puncture needle, said apparatus comprising;
a touch portion to which an epidermis is touched;
puncturing means for operating said puncture needle so as to puncture the epidermis touched to said touch portion;
evacuating means for evacuating the puncture site of the epidermis to be punctured by said puncture needle as well as a housing space for housing said puncture needle;
pressure detecting means for detecting the pressure in said housing space;
measuring means for measuring an amount of a specific component in the body fluid sampled from the puncture site; and
notifying means for notifying specific information;
wherein said housing space is tried to evacuate by said evacuating means, and a notice based on the information from said pressure detecting means is outputted by said notifying means.

(13) A body fluid component measuring apparatus used with a chip mounted thereto, said chip including a puncture needle, said apparatus comprising:
a touch portion to which an epidermis to be punctured is touched;
puncturing means for operating said puncture needle so as to puncture the epidermis touched to said touch portion;
evacuating means for evacuating the puncture site of the epidermis to be punctured by said puncture needle as well as a housing space for housing said puncture needle;
pressure detecting means for detecting the pressure in said housing space;
measuring means for measuring an amount of a specific component in the body fluid sampled from the puncture site; and
notifying means for notifying specific information;
wherein said housing space is tried to evacuate by said evacuating means, and when the evacuation state of said housing space is not detected by said pressure detecting means, a notice about an error is outputted by said notifying means.

(14) A body fluid component measuring apparatus used with a chip mounted thereto, said chip including a puncture needle, said apparatus comprising:
a touch portion to which an epidermis to be punctured is touched;
puncturing means for operating said puncture needle so as to puncture the epidermis touched to said touch portion;
evacuating means for evacuating a puncture site of the epidermis to be punctured by said puncture needle as well as a housing space for housing said puncture needle;
pressure detecting means for detecting the pressure in said housing space;
measuring means for measuring an amount of a specific component in a body fluid sampled from the puncture site;
notifying means for notifying specific information;
wherein said housing space is tried to evacuate by said evacuating means, and when the evacuation state of said housing space is not detected by said pressure detecting means, a notice to correct the position of the epidermis touched to said touch portion is outputted by said notifying means, and when the evacuation state of said housing space is not detected by said pressure detecting means even after a specific time has elapsed, a notice about an error is outputted by said notifying means.

(15) A body fluid component measuring means described in any one of (12) to (14), wherein when the evacuation state of said housing space is detected by said pressure detecting means, said puncture needle is operated by said puncturing means.

(16) A body fluid component measuring apparatus used with a chip mounted thereto, said chip including a puncture needle, said apparatus comprising:

a touch portion to which an epidermis to be punctured is touched;

puncturing means for operating said puncture needle so as to puncture the epidermis touched to said touch portion;

evacuating means for evacuating a puncture site of the epidermis to be punctured by said puncture needle as well as a housing space for housing said puncture needle;

pressure detecting means for detecting the pressure in said housing space; and measuring means for measuring an amount of a specific component in a body fluid sampled from the puncture site;

wherein said housing space is tried to evacuate by said evacuating means, and when the evacuation state of said housing space is detected by said pressure detecting means, said puncture needle is operated by said puncturing means.

(17) A body fluid component measuring means described in (15) or (16), further comprising:

operation starting means including an electrical drive source, said means being used for starting the operation of said puncturing means by drive of said drive source;

wherein the evacuation state of said housing space is detected by said pressure detecting means, the operation of said puncturing means is started by said operation starting means and said puncture needle is operated by said puncturing means.

(18) A body fluid component measuring apparatus described in any one of (12) to (16), wherein said puncturing means has a plunger and an urging member for urging said plunger in the direction toward the tip side.

(19) A body fluid component measuring apparatus described in (18), wherein said plunger has a locking portion for restricting the movement of said plunger in the direction toward the tip side, and when the locking of said locking portion is released in the state that the plunger remains urged by said urging member, said plunger is moved in the direction toward the tip side to allow said puncture needle to puncture the epidermis.

(20) A body fluid component measuring apparatus described in (19), further comprising operation starting means including an electrical drive source, said means being used for releasing the locking of said locking portion by drive of said drive source;

wherein when the evacuation state of said housing space is detected by said pressure detecting means, the locking of said locking portion is released by said operation starting means.

(21) A body fluid component measuring apparatus described in any one of (12) to (20), wherein when the evacuation state of said housing space is detected by said pressure detecting means, the evacuation state is once released, and then the puncture is performed and the puncture site of the finger punctured by said puncture needle as well as said housing space for housing said puncture needle are evacuated.

(22) A body fluid component measuring apparatus described in any one of (12) to (21), further comprising a housing for holding said chip and housing said puncturing means, wherein said evacuating means brings said housing space in said housing into an evacuation state.

(23) A body fluid component measuring apparatus described in (22), wherein said pressure detecting means detects the pressure in said housing space in said housing.

The above object is achieved by configurations (24) to (32) according to a third aspect of the present invention.

(24) A body fluid component measuring apparatus for sampling a body fluid via an epidermis and measuring a component of the body fluid, comprising:

a touch portion to which the epidermis is touched;

a spaced air-tightly sealed by the epidermis touched to said touch portion;

pressure adjusting means for adjusting the pressure in said space; and measuring means for measuring an amount and/or a property of a specific component of the body fluid sampled in said space;

wherein at the time of sampling the body fluid in said space via the epidermis, said space is evacuated by said pressure adjusting means with the pressure fluctuated with elapsed time.

(25) A body fluid component measuring apparatus used with a chip mounted thereto, said chip including a puncture needle, said apparatus comprising:

a touch portion to which an epidermis to be punctured is touched;

puncturing means for operating said puncture needle so as to puncture the epidermis touched to said touch portion;

pressure adjusting means for adjusting the pressure in a housing space for housing said puncture needle; and measuring means for measuring an amount of a specific component in a body fluid sampled from the puncture site;

wherein at the time of sampling the body fluid from the puncture site, said space is evacuated by said pressure adjusting means with the pressure fluctuated with elapsed time.

(26) A body fluid component measuring apparatus described in (25), further comprising:

pressure detecting means for detecting the pressure in said housing space;

wherein the pressure in said housing space is adjusted, on the basis of information from said pressure detecting means, by said pressure adjusting means.

(27) A body fluid component measuring apparatus described in (25) or (26), wherein at the time of sampling the body fluid, the pressure in said housing space is alternately changed, by said pressure adjusting means, between a first pressure lower than atmospheric pressure and a second pressure higher than the first pressure.

(28) A body fluid component measuring apparatus described in (27), wherein said second pressure is equal to or less than atmospheric pressure.

(29) A body fluid component measuring apparatus described in (27) or (28), wherein a difference between said second pressure and said first pressure is in a range of 100 to 600 mmHg.

(30) A body fluid component measuring apparatus described in any one of (27) to (29), wherein a period of the pressure fluctuation is in a range of 1 to 30 sec.

(31) A body fluid component measuring apparatus described in (25) or (26), wherein at the time of sampling body fluid, at least one cycle of reducing the pressure in said housing space once to a first pressure lower than atmospheric pressure and then gradually increasing the pressure in said housing space is performed by said pressure adjusting means.

(32) A body fluid component measuring apparatus described in any one of (27) to (31), wherein said first pressure is in a range of 100 to 600 mmHg.

The first, second, and third aspect of the present invention can be further configured as described below.

(33) A body fluid component measuring apparatus described in any one of (1) to (8), (14) to (23), and (25) to (32), wherein said chip has said touch portion to which the epidermis to be punctured is touched.

(34) A body fluid component measuring apparatus described in any one of (1) to (8), (14) to (23), and (25) to (33), wherein said chip has said test paper and a blood passage for supplying blood to said test paper.

(35) A body fluid component measuring apparatus described in (34), wherein said test paper is specialized for measurement of a blood sugar level.

BRIEF DESCRIPTION OF DRAWINGS

FIG. 1 is a perspective view typically showing a first embodiment of a body fluid component measuring apparatus according to the present invention;

FIG. 2 is a vertical sectional view showing a configuration example of a chip used for the present invention;

FIG. 23 is a graph showing a pressure pattern in a puncture needle housing space (bore portion 52) at the time of sampling blood in the second aspect of the present invention;

FIG. 24 is a graph showing another pressure pattern in a puncture needle housing space (bore portion 52) at the time of sampling blood in the second aspect of the present invention;

FIG. 31 is a vertical sectional view showing the configuration example of the essential portions of the body fluid component measuring apparatus according to the first embodiment of the third aspect of the present invention (in a final state);

BEST MODE FOR CARRYING OUT THE INVENTION

A body fluid component measuring apparatus of the present invention is adapted to sample a body fluid of a user via the epidermis (skin) of the user, and to measure a specific component of the body fluid.

A site of a user, at which a body fluid is to be sampled via the epidermis (called "puncture site" in embodiments), may be selected from a finger, a palm portion, a back portion, and a side portion of a hand, an arm portion, and a thigh portion. In particular, a preferable puncture site is a finger.

The following description will be made by example of a body fluid component measuring apparatus (blood sugar level measuring apparatus) of a type puncturing the epidermis of a finger tip (finger) representative of a puncture site of a user and sampling blood representative of a body fluid from the finger tip.

Several body fluid component measuring apparatuses of the present invention will be hereinafter described on the basis of preferred embodiments shown in the accompanying drawings.

Figure 3:
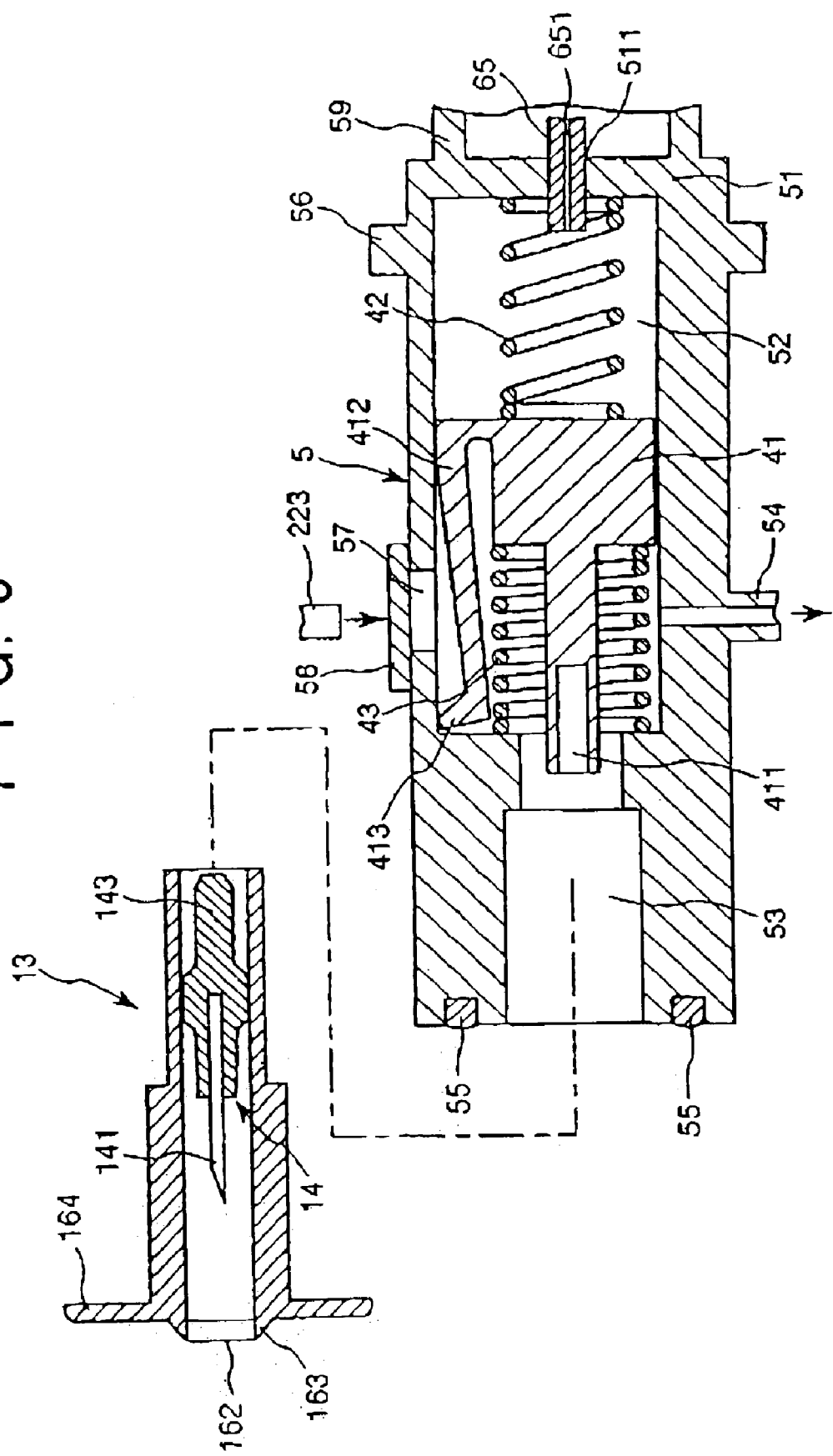
FIG. 3 is a vertical sectional view showing configuration examples of a puncturing means and a housing for housing the puncturing means in the body fluid component measuring apparatus according to the first embodiment (in a state before the chip is mounted to the housing)
Figure 4:
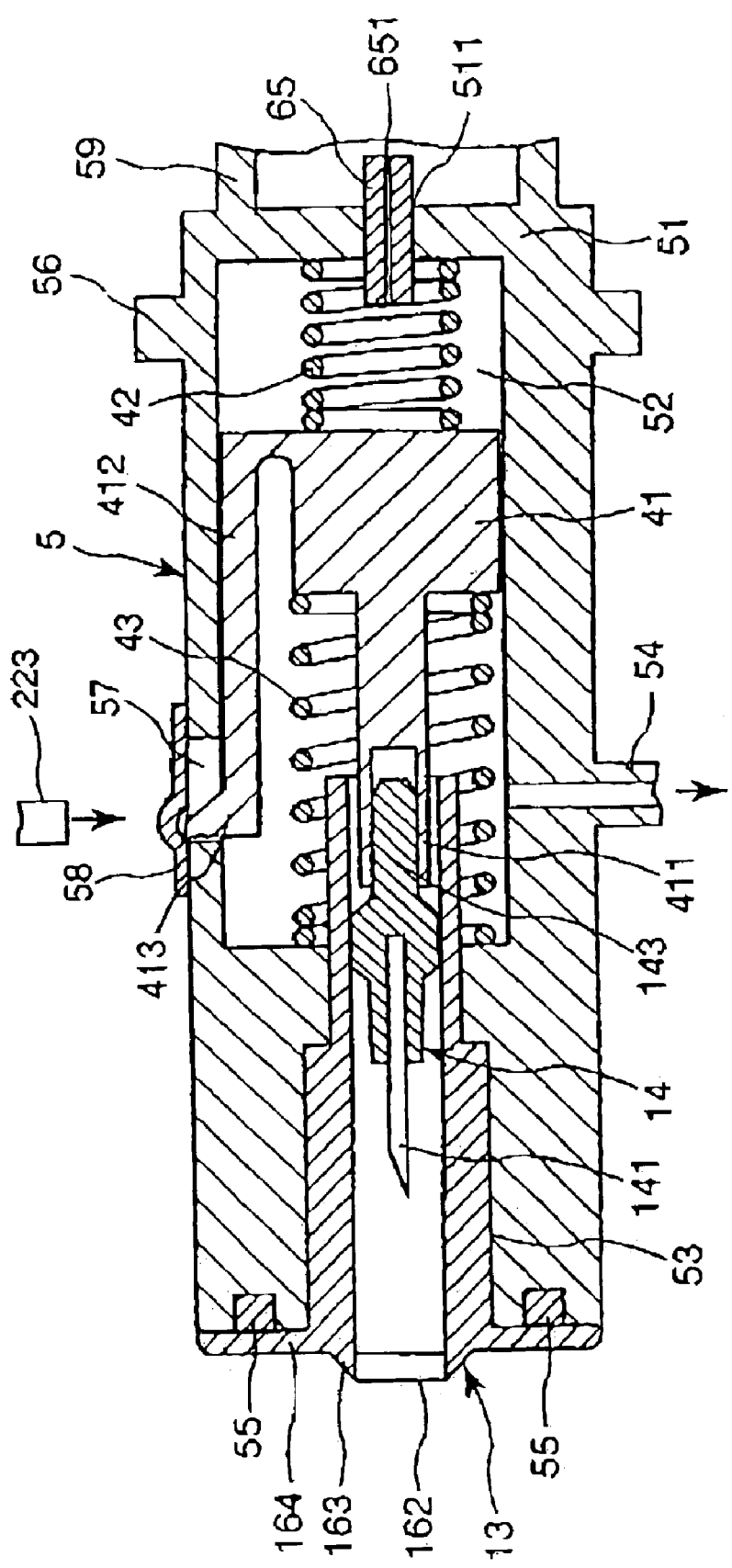
FIG. 4 is a vertical sectional view showing the configuration examples of the puncturing means and the housing for housing the puncturing means in the body fluid component measuring apparatus according to the first embodiment (in a state after the chip is mounted to the housing)
Figure 11:
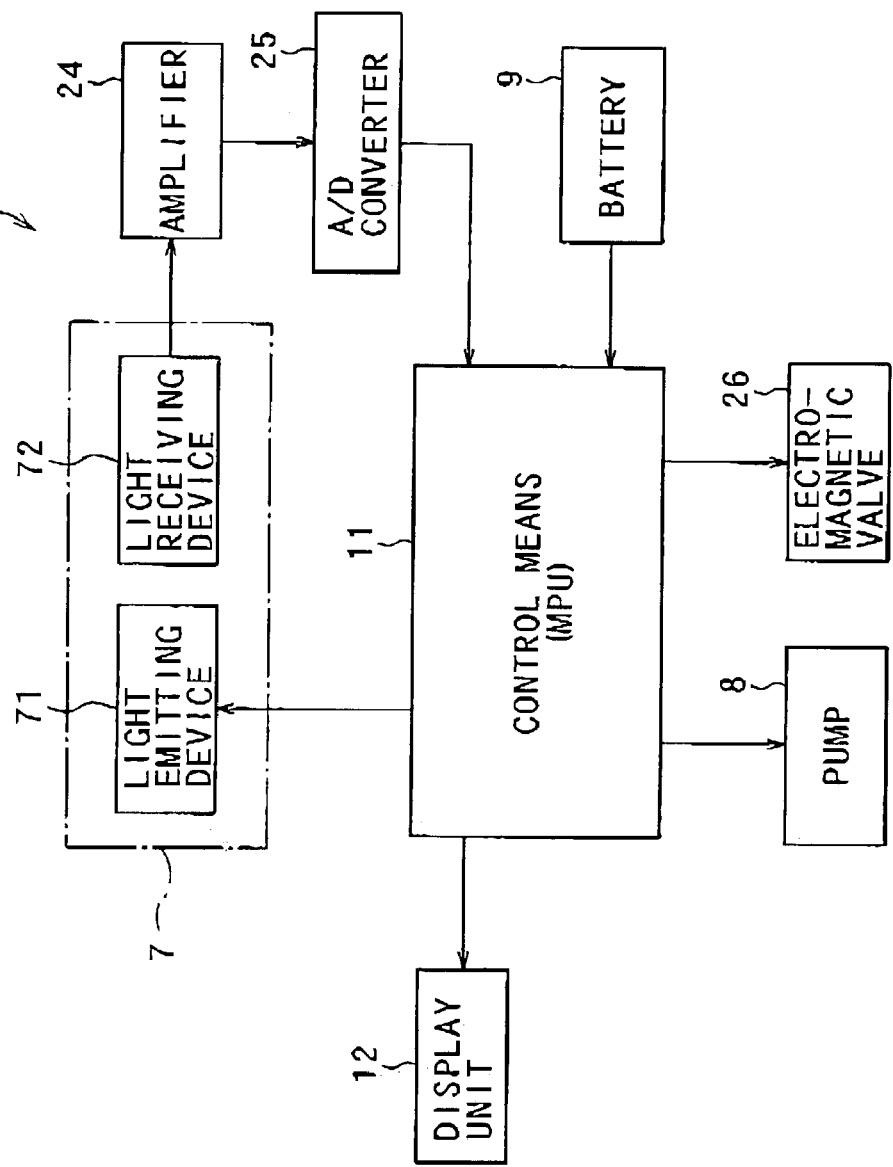
FIG. 11 is a block diagram showing a circuit configuration of the body fluid component measuring apparatus according to the first embodiment.
Figure 12:
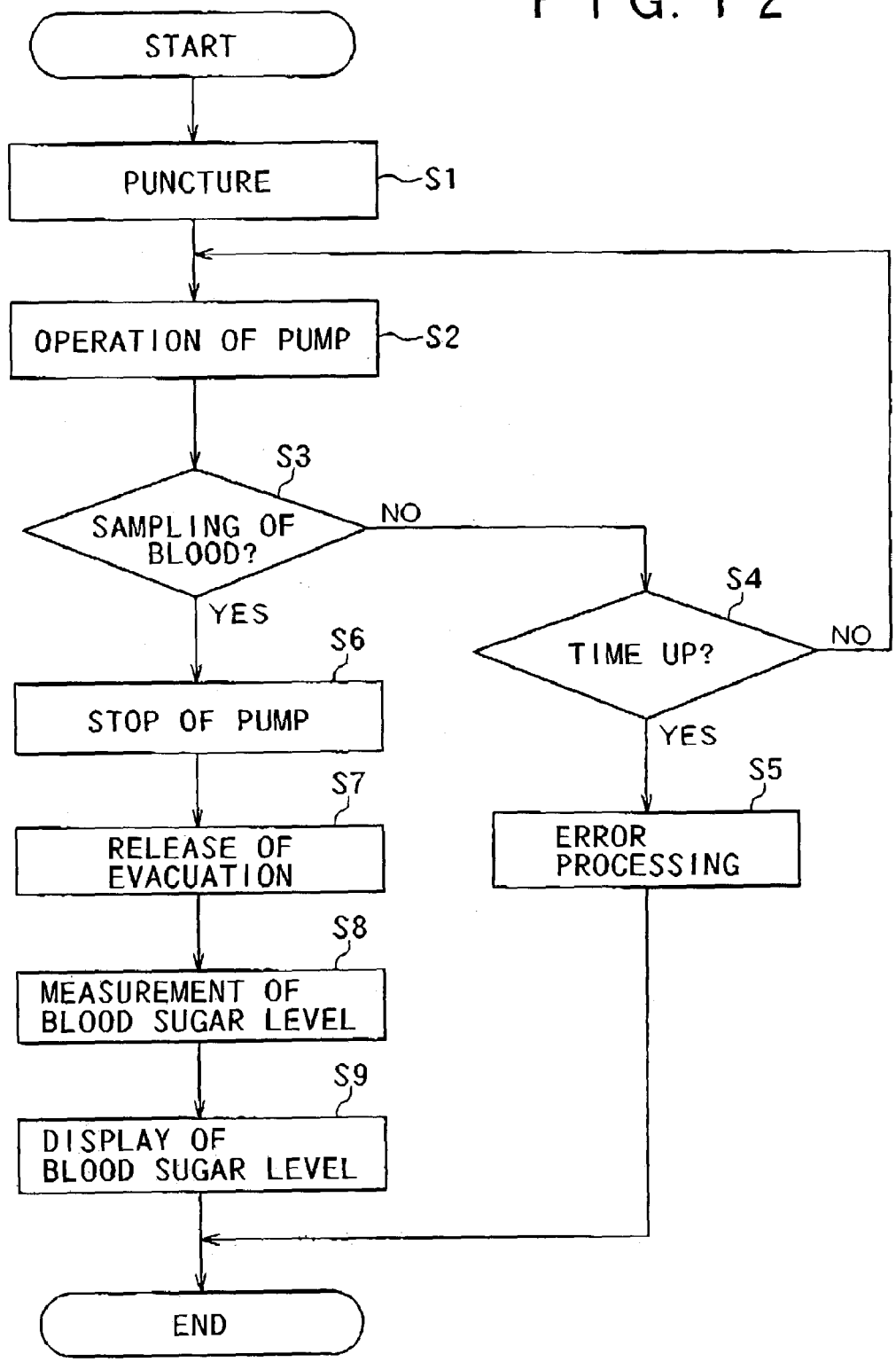
FIG. 12 is a flow chart showing a control operation of a control means for the body fluid component measuring apparatus (which control operation partially includes an action of an operator)

FIG. 1 is a perspective view typically showing a first embodiment of a body fluid component measuring apparatus according to a first aspect of the present invention; FIG. 2 is a vertical sectional view showing a configuration example of a chip shown in the present invention; FIGS. 3 and 4 are vertical sectional views showing configuration examples of a puncturing means and a housing for housing the puncturing means, which are provided in the body fluid component measuring apparatus according to the first embodiment, respectively; FIGS. 5 to 10 are vertical sectional views showing configuration examples of essential portions of the body fluid component measuring apparatus according to the first embodiment, respectively; FIG. 11 is a block diagram showing a circuit configuration of the body fluid component measuring apparatus according to the first embodiment; and FIG. 12 is a flow chart showing control operations of a control means (partially including operations and the like of an operator or user) of the body fluid component measuring apparatus according to the first embodiment. It is to be noted that FIGS. 1 to 10 are depicted with the "base end side" of the apparatus taken as the right side and the "tip side" of the apparatus taken as the left side.

Figure 5:
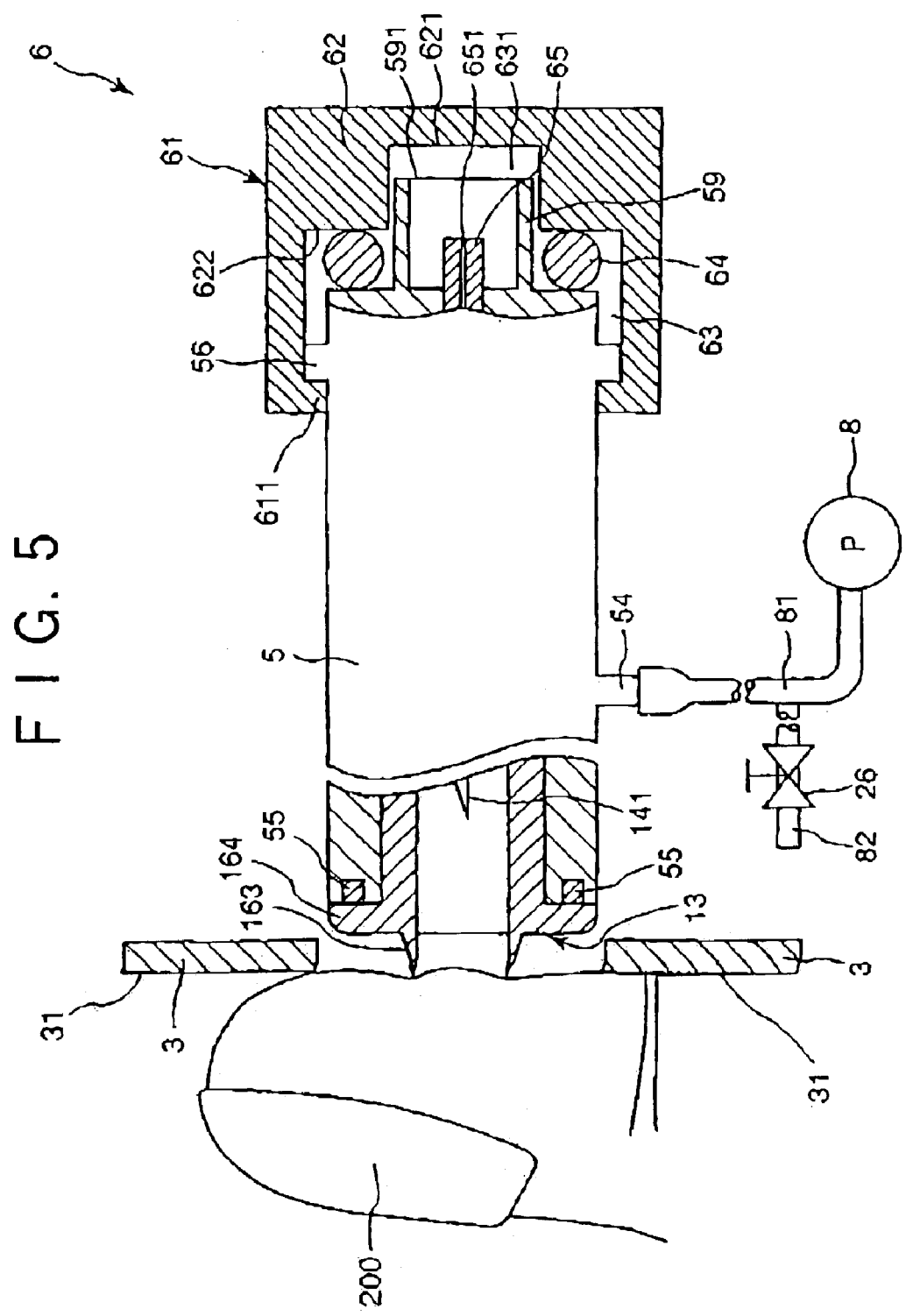
FIG. 5 is a vertical sectional view showing a configuration example of essential portions of the body fluid component measuring apparatus according to the first embodiment (in a state before operation of the puncturing means)

As shown in FIGS. 1, 5 and 11, a body fluid component measuring apparatus (blood component measuring apparatus) 1 according to the first embodiment includes a main body 2, a touch portion 3 disposed on the main body 2, a puncturing means 4 housed in a housing 5, a chip withdrawing mechanism 6 provided on the base end side of the housing 5, a measuring means 7 for detecting the sampling of blood and measuring a specific component in the sampled blood, a pump 8 for evacuating the interior of the housing 5, an electromagnetic valve 26 for releasing, relieving, or holding an evacuation state of the interior of the housing 5, a battery (power source) 9, a control means 11 provided on a circuit board 10, and a display unit 12.

At time of use, the chip 13 is mounted to the body fluid component measuring apparatus 1, and during use of the apparatus 1, a specific component (for example, oxygen, carbon dioxide, or water vapor) is required for chemical reaction upon measurement of a specific component in blood. Each of constituent elements of the apparatus 1 will be described below.

The main body 2 is composed of a housing body 21 and a lid body 22, which are disposed opposite to each other. The main body 2 internally has a housing space 23, in which the puncturing means 4, the housing 5, the chip withdrawing mechanism 6, the measuring means 7, the pump 8, the electromagnetic valve 26, the battery 9, the circuit board 10, the control means 11, and the display unit 12 are housed.

A wall portion 211 on the tip side of the housing body 21 has an opening 212 passing through the housing body 21. The opening 212 has a circular shape in cross-section. The chip 13 is mounted (held) to the housing 5 (to be described later) via the opening 212.

The touch portion 3 is provided on a plane on the tip side of the wall portion 211 so as to surround the outer periphery of the opening 212. The touch portion 3 has a shape corresponding to that of the finger tip (finger). A finger touch plane 31 is formed on the tip side of the touch portion 3. The operator (user) operates the body fluid component measuring apparatus 1 while touching the finger tip to the touch portion 3 (finger touch plane 31).

With such an operation of the apparatus 1, the epidermis of the finger is punctured, blood is sampled therefrom, and an amount of a specific component (represented by glucose in this embodiment) of the sampled blood is measured.

To be more specific, according to such a blood sugar level measurement apparatus, the finger tip is first touched to the tip of the chip so as to air-tightly seal the tip opening 212.

The finger tip is then punctured with a puncture needle projecting from the tip opening 212. In such a state, a sucking means is operated (to cause an evacuation state), whereby blood is sucked from the puncture site and is then sampled. A blood sugar level of the sampled blood is then measured by the measuring apparatus 1.

The upper surface of the lid body 22 has a display window (opening) 221 passing through the lid body 22. The display window 221 is covered with a plate member made from a transparent material.

The display unit 12 is disposed in the containing space 23 at a position corresponding to that of the display window 221. Accordingly, various kinds of information displayed on the display unit 12 can be checked via the display window 221.

The display unit 12 is composed of, for example, a liquid crystal display device (LCD) or the like. Various kinds of information associated with ON/OFF of the power source, power voltage (remaining capacity of the battery), measured value, measurement date & hour, error indication, operation guidance, and the like can be displayed on the display unit 12.

An operating button 222 is provided on the upper surface of the lid body 22. The body fluid component measuring apparatus 1 is configured such that the puncturing means 4 (to be described later) and the pump (evacuating means) 8 are sequentially or nearly simultaneously operated by depressing the operating button 222.

The body fluid component measuring apparatus 1 may be configured such that the power source is turned on by depressing the operating button 222.

The circuit board 10 is disposed under the display unit 12 in FIG. 1. The control means 11 in the form of a microcomputer is mounted on the circuit board 10. The control means 11 controls various operations of the body fluid component measuring apparatus 1, for example, an operation to decide whether or not blood has been sampled. The control means 11 incorporates a calculating portion for calculating an amount of glucose (blood sugar value) in blood on the basis of a signal from the measuring means 7.

The pump 8 is disposed as the evacuating means (sucking means) under the left half of the circuit board 10 in FIG. 1. The pump 8 is electrically operated, and is connected to a ventilation passage 54 formed in the housing 5 (to be described later) via a tube 81. The tube 81 is flexible, and is made from a polymer material selected, for example, from polyolefines such as polyvinyl chloride, polyethylene, polypropylene, and ethylene-vinyl acetate copolymer (EVA), and other polymers such as polyamide, polyester, silicon rubber, and polyurethane.

The pump 8 is operated to suck and discharge air in a bore portion 52 of the housing 5 and thereby evacuate the bore portion 52 of the housing 5.

The pump 8 may be any pump insofar as it can evacuate both the bore portion 52 of the housing 5 and the puncture site of the finger to a degree of vacuum allowing suction of blood from the puncture site of the finger (for example, about 100 to 400 mmHg).

The battery 9 is disposed as the power source under the right half of the circuit board 10 in FIG. 1. The battery 9 is electrically connected to the pump 8, the electromagnetic valve 26, the control means 11, the display unit 12, and the like for supplying a necessary power to each of these constituted elements.

The measuring means 7 is disposed in front of the pump 8 in FIG. 1 The measuring means 7 is adapted to optically detect the supply (sampling) of blood to a strip of test paper 18 provided for the chip 13 (to be described later), and to optically measure an amount of glucose in the blood diffused in the test paper 18. The measuring means 7 is located in the vicinity of a side portion, at which the test paper 18 is positioned, of the chip 13 in a state that the chip 13 is mounted to and held by the housing 5.

In this way, the measuring means 7 has both the function of detecting the sampling of blood and the function of measuring an amount of glucose (specific component) in blood diffused in the test paper 18. As a result, in comparison with an apparatus in which two means having the above-described two functions are separately provided, the apparatus 1 including the measuring means 7 is advantageous in reducing the number of parts, simplifying the configuration of the apparatus 1, and reducing the number of steps of assembling the constituent elements into the apparatus 1.

The measuring means 7 has a light emitting device (light emitting diode) 71 and a light receiving device (photodiode) 72.

The light emitting device 71 is electrically connected to the control means 11, and the light receiving device 72 is electrically connected to the control means 11 via an amplifier 24 and an A/D converter 25.

The light emitting device 71 is operated for emission of light on the basis of a signal from the control means 11. The light emitted from the light emitting device 71 is preferably pulse light emitted intermittently at specific time intervals.

When the light emitting device 71 is turned on in a state that the chip 13 is mounted to the housing 5, the test paper 18 is irradiated with the light emitted from the light emitting device 71. The light is reflected from the test paper 18 and is received by the light receiving device 72. In the light receiving device 72, the light is subjected to photoelectric conversion. An analogue signal corresponding to the quantity of light is outputted from the light receiving device 72, and is suitably amplified by the amplifier 24. The amplified analogue signal is converted into a digital signal by the A/D converter 25, to be inputted in the control means 11.

The control means 11 decides, on the basis of the inputted signal, whether or not blood has been sampled, that is, whether or not blood has been diffused in the test paper 18 of the chip 13.

The control means 11 performs a specific calculating operation on the basis of the inputted signal, and further, a correcting calculation if needed, to determine an amount of glucose (blood sugar level) in the blood. The blood sugar level thus obtained is displayed on the display unit 12.

The housing 5 in which the puncturing means 4 is housed and the chip withdrawing mechanism 6 connected to the base end side of the housing 5 are disposed in front of the measuring means 7 in FIG. 1.

The chip withdrawing mechanism 6 is fixed to the housing body 21 Meanwhile, the housing 5 is not fixed to the housing body 21 but is disposed so as to be movable in the axial direction (from right or left to left or right in FIG. 1) by the chip withdrawing mechanism 6.

As described above, at time of use of the body fluid component measuring apparatus 1, the chip 13 is mounted to the housing 5. As is shown in FIG. 2, the chip 13 includes a puncture needle 14, a first housing 15 for slidably housing the puncture needle 14, a second housing 16 disposed on the outer periphery of the first housing 15, a test paper fixing portion 17 disposed on an outer peripheral portion of the second housing 16, and the test paper 18 fixed to the test paper fixing portion 17.

The puncture needle 14 is composed of a needle body 141 and a hub 142 fixed to the base end side of the needle body 141. The puncture needle 15 is housed in a bore portion 152 of the first housing 15.

The needle body 141 is formed of a hollow member or a solid member made from a metal material such as a stainless steel, aluminum, an aluminum alloy, titanium, or a titanium alloy. A sharp edge (needle tip) is formed at the tip of the needle body 141. The surface (skin) of the finger tip is punctured by the edge of the needle body 141.

The hub 142 is formed of an approximately columnar member. The hub 142 is slid with its outer periphery being in contact with an inner peripheral surface 151 of the first housing 15.

A small-diameter portion 143 is formed on the base end side of the hub 142 The small-diameter portion 143 is fitted in a needle holder 411 of a plunger 41 constituting part of the puncturing means 4 (to be described later).

The first housing 15 is formed of a cylindrical member with its bottom closed with a wall portion 153, and internally has a bore portion 152.

An approximately central portion of the wall portion 153 has a hole 154 formed into a circular shape in cross-section. At the time of puncture of the epidermis of the finger tip (finger), the needle body 141 passes through the hole 154. The diameter of the hole 154 is set to be smaller than the outer diameter of the tip of the hub 142. Accordingly, after the puncture needle 14 is moved in the bore portion 152 in the direction toward the tip side until the tip of the hub 142 comes in contact with the base end of the wall portion 153, the puncture needle 14 is no longer moved in the direction toward the tip side. As a result, at the time of puncture of the finger tip, the length of a portion, projecting from the tip of the chip 13, of the needle body 141 can be kept constant. This is advantageous in that the finger tip can be more certainly prevented from being too deeply punctured with the edge of the needle body 141.

The puncture depth of the edge of the needle body 141 in the finger tip may be adjusted by providing a mechanism for adjusting a movement distance of the plunger 41 (to be described later).

The second housing 16 is fixed to the outer periphery of the first housing 15.

The second housing 16 is formed of an approximately cylindrical member, and internally has a bore portion 161.

A ring-shaped contact portion 163 is formed at the tip of the second housing 16 in such a manner as to project outwardly therefrom. The contact portion 163 is a portion to which the finger tip is to be touched (that is, the touch portion), and internally has a tip opening (opening) 162 through which the bore portion 161 is opened. The outer peripheral edge of the tip of the contact portion 163 is formed into a shape suitable for stimulating, when the finger tip is touched thereto, the neighborhood of the puncture site to moderate pain caused by puncture, and also suitable for suppressing, when the bore portion 161 is evacuated, the flow of air between the tip of the contact portion 163 and the surface of the finger tip as much as possible. It is to be noted that the contact portion 163 is not necessarily provided at the tip of the second housing 16. For example, the tip surface of the second housing 16 may be flattened in place of provision of the contact portion 163 at the tip of the second housing 16.

In the second housing 16, a ring-shaped flange 164 is formed on an outer peripheral portion near the base end of the contact portion 163 in such a manner as to project outwardly therefrom. When the chip 13 is mounted to the housing 5 (to be described later), the base end of the flange 164 is brought into contact with the tip of the housing 5, to determine the position of the chip 13 to the housing 5.

An outer peripheral portion of the second housing 16 has a recess 165. The test paper fixing portion 17 on which the disk-like test paper 18 has been fixed is mounted in the recess 165.

A blood introducing guide 166 is formed on an inner peripheral surface of the second housing 16 in such a manner as to project inwardly therefrom in the bore portion 161. The blood introducing guide 166 has a function of receiving, after puncture of the finger tip, the blood (specimen) having flown from the tip opening 162 into the bore portion 161.

In such a chip 13, a blood passage 19 communicating the bore portion 161 of the second housing 16 to the outside of the chip 13 via the second housing 16 and the test paper fixing portion 17 is formed. The blood passage 19 is a flow passage for introducing the blood obtained by puncture of the finger tip to the test paper 18. The blood passage 19 has both a passage opening 191 opened to the bore portion 161 and a passage opening 192 opened to the outside of the chip 13. It is to be noted that the passage opening 192 is located at a center portion of the test paper 18.

The blood introducing guide 166 is formed near the passage opening 191. Accordingly, the blood received by the blood introducing guide 166 is efficiently introduced from the passage opening 191 to the blood passage 19. The blood flowing in the blood passage 19 reaches the passage opening 192 due to a capillary phenomenon, and is supplied to the center portion of the test paper 18 disposed to cover the passage opening 192, to be thus radially diffused in the test paper 18.

The test paper 18 is configured by supporting a reagent on a carrier capable of absorbing and diffusing blood therein.

The carrier is formed of a sheet-like porous member such as a non-woven fabric, a woven fabric, or an expanded sheet. The porous member preferably has a hydrophilic property.

The reagent to be supported on the carrier is suitably determined depending on a component, to be measured, in blood (specimen). For example, a combination of glucose oxidase (GOD), peroxidase (POD), and a color coupler (coloring reagent) such as 4-aminoantipyrin or N-ethyl-N-(2-hydroxy-3-sulfopropyl)-m-toluidine may be used as a reagent for measurement of a blood sugar level. A combination of a material reactive with a blood component, for example, ascorbate oxidase, alcohol oxidase, or cholesterol oxidase and the above-described color coupler (coloring reagent) may be also used depending on a component to be measured. The reagent may contain a buffer such as a phosphate buffer. It is to be noted that the kind of reagent and a component to be measured are, of course, not limited to those described above.

Such a chip 13 is removably fitted in the housing 5 (fitting portion 53) via the opening 212 of the housing body 21 as described above.

As shown in FIGS. 3 and 4, the housing 5 is formed of a cylindrical member with its bottom closed with a wall portion 51, and internally has a bore portion (housing space) 52. The housing 5 internally has, on the tip side, a small-diameter fitting portion 53. To be more specific, the inner diameter of the fitting portion 53 is set to correspond to the diameter of the outer periphery of the chip 13. The chip 13 is inserted and fixedly fitted in the fitting portion 53. It is to be noted that in FIGS. 3 and 4, the chip 13 is depicted with its structure simplified for easy understanding of description.

A side portion of the housing 5 has the ventilation passage 54 for communicating the bore portion 52 to the outside. The ventilation passage 54 is connected to the pump 8 via the tube 81. Air in the bore portion 52 is sucked via the ventilation passage 54 and the tube 81 by the pump 8, to evacuate the bore portion 52 (including the interior of the chip 13).

As shown in FIG. 5, one end of a tube 82 is branched from a middle point of the tube 81, and the other end of the tube 82 is opened to the outside of the main body 21. The tube 82 is flexible, and may be made, for example, from the same material as that for forming the tube 81.

The electromagnetic valve 26 is provided in a middle point of the tube 82 for opening/closing the flow passage of the tube 82.

When the electromagnetic valve 26 remains closed (OFF state), the evacuation state of the bore portion 52 (including the interior of the chip 13) is kept. On the other hand, when the electromagnetic valve 26 is opened (ON state), air (atmospheric air) is introduced from the outside into the bore portion 52 having been kept in the evacuation state via the tubes 82 and 81 and the ventilation passage 54, to release or relieve the evacuation state of the bore portion 52.

Accordingly, an evacuation releasing means is composed of the tubes (flow passage) 81 and 82 and the electromagnetic valve 26.

As shown in FIGS. 3 and 4, an approximately central portion of the wall portion 51 of the housing 5 has a hole 511. A fine tube 65 internally having an orifice (passage) 651 is provided in the hole 511. Air flows between the bore portion 52 and a volume variable chamber 631 (to be described later), which are disposed on both sides of the fine tube 65, via the orifice 651.

A ring-shaped seal ring (sealing member) 55 is fitted in the tip surface of the housing 5. With this provision of the seal ring 55, when the chip 13 is mounted to the housing 5, the base end of the flange 164 of the chip 13 is brought into contact with the seal ring 55, to keep the air-tightness of the bore portion 52.

The seal ring 55 is made from an elastic material selected, for example, from various kinds of rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluorocarbon rubber, and various kinds of thermoplastic elastomers such as a styrene based elastomer, a polyolefine based elastomer, a polyvinyl chloride based elastomer, a polyurethane based elastomer, a polyester based elastomer, a polyamide based elastomer, a polybutadine based elastomer, and a fluorocarbon rubber based elastomer.

A ring-shaped flange 56 is formed on the outer periphery of a base end portion of the housing 5 in such a manner as to project outwardly therefrom. A cylindrical projection 59 is formed at the base end of the housing 5.

The puncturing means 4 is housed in a portion, on the base end side from the fitting portion 53, of the bore portion 52 of the housing 5. The puncturing means 4 is adapted to move the puncture needle 14 mounted thereto in the direction toward the tip side for puncturing the surface of the finger tip with the cutting edge of the needle body 141.

The puncturing means 4 is composed of the plunger 41, a coil spring (urging member) 42 for urging the plunger 41 in the direction toward the tip side, and a coil spring (urging member) 43 for urging the plunger 41 in the direction toward the base end.

A cup-shaped needle holder 411 is provided at a tip portion of the plunger 41. The small-diameter 143 of the puncture needle 14 is removably fitted in the needle holder 411. An elastically deformable elastic piece 412 is provided on a base end portion of the plunger 41. The elastic piece 412 has, at its tip, a locking portion 413 having the shape of a projecting arm.

In a state before the chip 13 is mounted to the housing 5, that is, in a state before the puncture needle 14 is mounted to the plunger 41 (see FIG. 3), the locking portion 413 is urged upwardly in FIG. 3 by the elastic force of the elastic piece 412, to be brought into contact with the inner peripheral surface of the housing 5. On the other hand, in a state that the chip 13 is mounted to the housing 5, that is, in a state that the puncture needle 14 is mounted to the plunger 41 (see FIG. 4), the locking portion 413 is inserted in an opening 57 formed so as to pass through the housing 5, to be locked with an edge portion of the opening 57. In this case, the movement of the plunger 41 in the direction toward the tip side is restricted. In addition, the opening 57 is closed with a flat seal sheet (sealing member) 58 to keep the air-tightness of the bore portion 52. The seal sheet 58 may be made from the same material as that for forming the above-described seal ring 55.

The coil spring (spring for puncture) 42 is disposed on the base end side of the plunger 41 in a state that both ends thereof are in contact with the plunger 41 and the wall portion 51. On the other hand, the coil spring (spring for return) 43 is disposed on the tip side of the plunger 41 in a state that both ends thereof are in contact with the plunger 41 and the fitting portion 53.

As shown in FIGS. 3 and 4, a locking releasing member 223 capable of moving the locking portion 413 toward the interior of the bore portion 52 (in the direction shown by an arrow in the figure) is provided outside the housing 5. The locking releasing member 223 is moved in interlocking with the above-described depressing operation of the operating button 222.

In the state that the locking portion 413 is locked with the edge portion of the opening 57, the coil spring 42 is in the compression state. In such a compression state, the coil spring 42 urges the plunger 41 in the direction toward the tip side. When the operating button 222 is depressed to move the locking releasing member 223 in the direction shown by the arrow in the figure, that is, to release the locking state of the locking member 413, the coil spring 42 is extended to move the plunger 41 in the direction toward the tip side, thereby causing the cutting edge of the needle body 141 to puncture the surface (skin) of the finger tip.

At the time, the coil spring 43 is compressed to urge the plunger 41 in the direction toward the base end side, that is, to return the plunger 41 in the direction toward the base end side. Thereafter, the movement of the plunger 41 is attenuated, and the plunger 41 is rested at a position where the elastic force of the coil spring 42 is balanced against the elastic force of the coil spring 43.

In the state that the plunger 41 is rested, the cutting edge of the needle body 141 is in a state being housed in she chip 13.

The chip withdrawing mechanism 6 is provided on the base end side of the housing 5.

The chip withdrawing mechanism 6 is adapted to move the housing 5 and the chip 13 mounted thereto in the direction away from the finger tip (denoted by reference numeral 200 in FIG. 5), that is, in the direction toward the base end side.

As shown in FIGS. 5 to 10, the chip withdrawing mechanism 6 includes a main body portion 61, a seal ring 64, and the fine tube 65.

The main body portion 61 is formed of a cylindrical member with its bottom closed with a wall portion 62, and internally has a bore portion 63. The base end side of the housing 5 is inserted in the bore portion 63.

A ring-shaped projection 611 is formed at the tip of the main body portion 61 in such a manner as to project inwardly therefrom. In a state before the chip withdrawing mechanism 6 is operated, the base end of the projection 611 is in contact with the tip of the flange 56. As a result, the movement of the housing 5 in the direction toward the tip side is restricted. In other words, the housing 5 is prevented from being slipped off from the main body portion 61.

At this time, the tip of the contact portion 163 nearly aligns with the finger touch plane 31 or slightly projects from the finger touch plane 31 (see FIG. 5). As a result, when the finger tip 200 is touched to the touch portion 3, the surface of the finger tip 200 certainly comes in contact with the contact portion 163, to certainly close the tip opening 162.

An approximately central portion of the wall portion 62 has a recess 621 formed into a circular shape in cross-section. The diameter of the recess 621 is set to be substantially equal to the outer diameter of the projection 59. The projection 59 is inserted in the recess 621. The outer diameter of the flange 56 is set to be substantially equal to the inner diameter of the main body portion 61. With this configuration, the offset in the vertical direction in the figure (more specifically, the offset between the center of the housing 5 and the center of the main body portion 61) can be certainly prevented irrespective of the position of the housing 5 in the axial direction.

The ring-shaped seal ring 64 is disposed between the outer periphery of the projection 59, that is, the base end of the housing 5 and a plane 622 on the tip side of the wall portion 62. The seal ring 64 is brought into air-tight contact with each of the base end of the housing 5 and the plane 622. As a result, the volume variable chamber (evaluation chamber) 631 having air-tightness is defined in a region surrounded by the seal ring 64, the base end of the housing 5, the plane 622, and the inner surface of the recess 621.

The seal ring 64 is formed of an elastic body, and therefore, in an operational state of the chip withdrawing mechanism 6 (in the state shown in FIG. 8), the housing 5 is urged in the direction toward the tip side by the elastic force of the seal ring 64. The seal ring 64 thus functions as an urging means. The seal ring 64 may be made from the same elastic material as that for forming the above-described seal ring 55 or the like.

The fine tube 65 is formed of a cylindrical member, and internally has the orifice (passage) 651. The orifice 651 is a passage communicating the bore portion 52 of the housing 5 to the volume variable chamber 631. The orifice 651 is required to be narrow enough to keep a large passing resistance of air. The diameter of the orifice 651 is not particularly limited but is preferably in a range of about 0.01 to 0.3 mm. By setting the diameter of the orifice 651 within the above range, it is possible to certainly keep the necessary passing (flow) resistance of air.

The timing of start of the operation of the chip withdrawing mechanisms after the operation of the pump 8 can be controlled by adjusting the diameter of the orifice 651.

The fine tube 65 is not limited to that shown in the figure, and although only one fine tube 65 is provided in this embodiment, a plurality of the fine tubes 65 may be provided if needed.

In such a chip withdrawing mechanism 6, when the pump 8 is operated in the state that the finger tip 200 is brought into contact with the contact portion 163 to seal the tip opening 162, the bore portion 52 (including the interior of the chip 13) is first evacuated, and then air in the volume variable chamber 631 flows in the bore portion 52 via the orifice 651, to start the evacuation of the volume variable chamber 631. Since the passing resistance of air in the orifice 651 is high, the volume of the volume variable chamber 631 is gradually reduced, so that the housing 5 and the chip 13 mounted thereto are gradually moved in the direction away from the finger tip 200.

Figure 8:
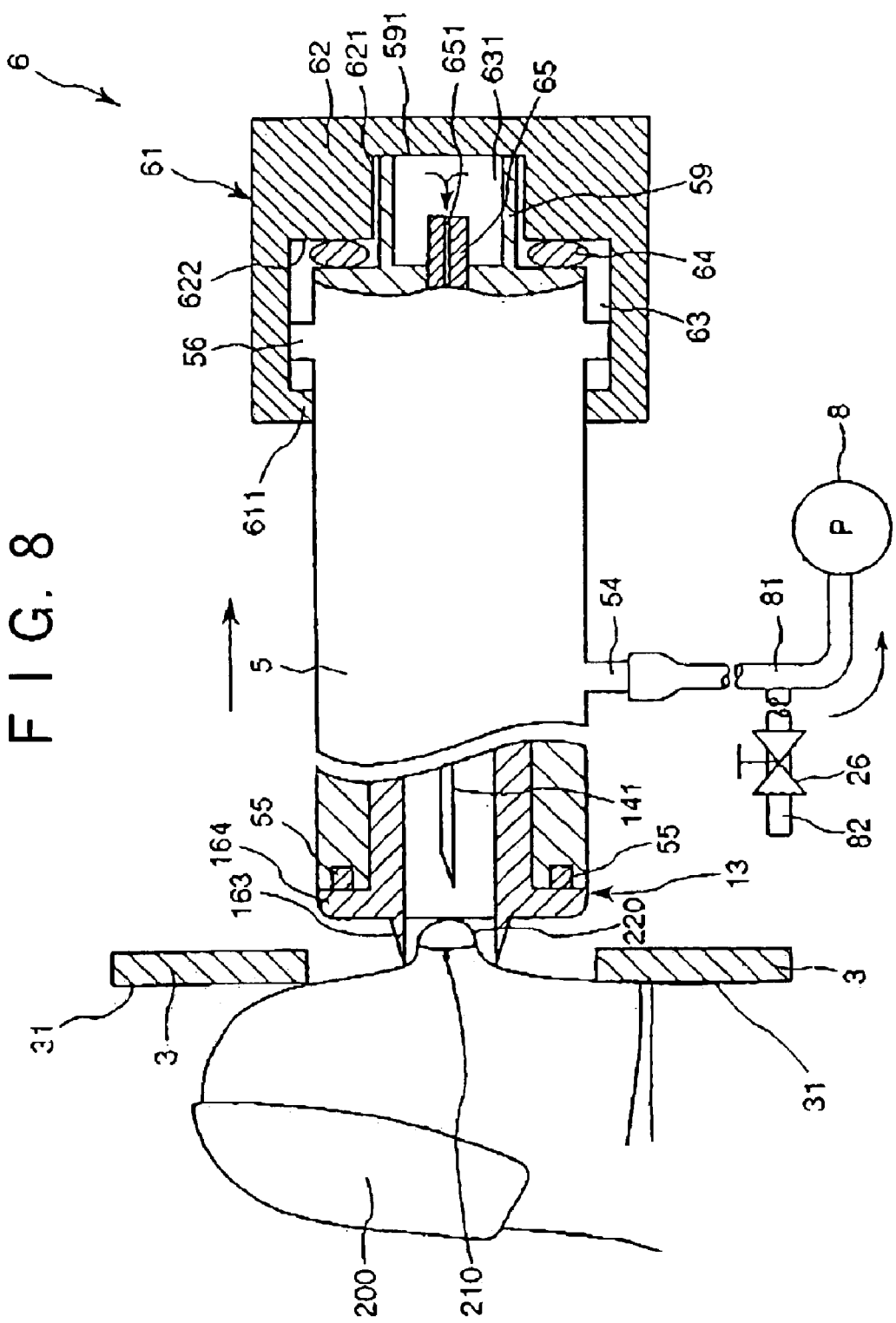
FIG. 8 is a vertical sectional view showing the configuration example of the essential portions of the body fluid component measuring apparatus according to the first embodiment (in a state at the time of operation of a chip withdrawing mechanism)

When the base end 591 of the projection 59 comes into contact with the bottom surface of the recess 621, the movement of the housing 5 and the chip 13 mounted thereto in the direction toward the base end side is stopped (see FIG. 8). Accordingly, it is possible to prevent the chip 13 from being excessively apart from the finger tip 200 by adjusting the axial length of the projection 59. In this way, a means for restricting the movement distance of the chip 13 from the finger tip 200, which is the maximum withdrawal distance, (movement distance restricting means) is composed of the projection 59 and the bottom surface, to be brought into contact with the projection 59, of the recess 621.

The separation distance between the chip 13 and the finger tip 200 (the maximum withdrawal distance of the chip 13) is not particularly limited but is preferably in a range of about 0.2 to 2.5 mm, more preferably, in a range of about 0.5 to 1.5 mm. By setting the separation distance within the above range, it is possible to more certainly sample a sufficient amount of blood for a short time, and also to more certainly prevent the finger tip 200 from being separated from the tip opening 162.

The operation of the chip withdrawing mechanism 6 follows the operation of the pump 8. To be more specific, after the pump 8 evacuates the bore portion 52 to attract the finger tip 200 at the tip opening 162, the chip withdrawing mechanism 6 gradually withdraws (moves) the chip 13 in the direction toward the base end side. As a result, the chip withdrawing mechanism 6 can separate the chip 13 from the finger tip 200 while keeping the evacuation state of the puncture site (which is denoted by reference numeral 210 in FIG. 6) of the finger tip 200.

Such a chip withdrawing mechanism 6 acts by making use of the evacuation force caused by the pump 8. From this viewpoint, the pump (evacuating means) 8 may be regarded as one of the constituent elements of the chip withdrawing mechanism 6.

Since the chip withdrawing mechanism 6 does not require provision of any additional drive source, such a mechanism 6 is advantageous in reducing the size and weight of the body fluid component measuring apparatus 1 and also reducing the production cost thereof.

Figure 6:
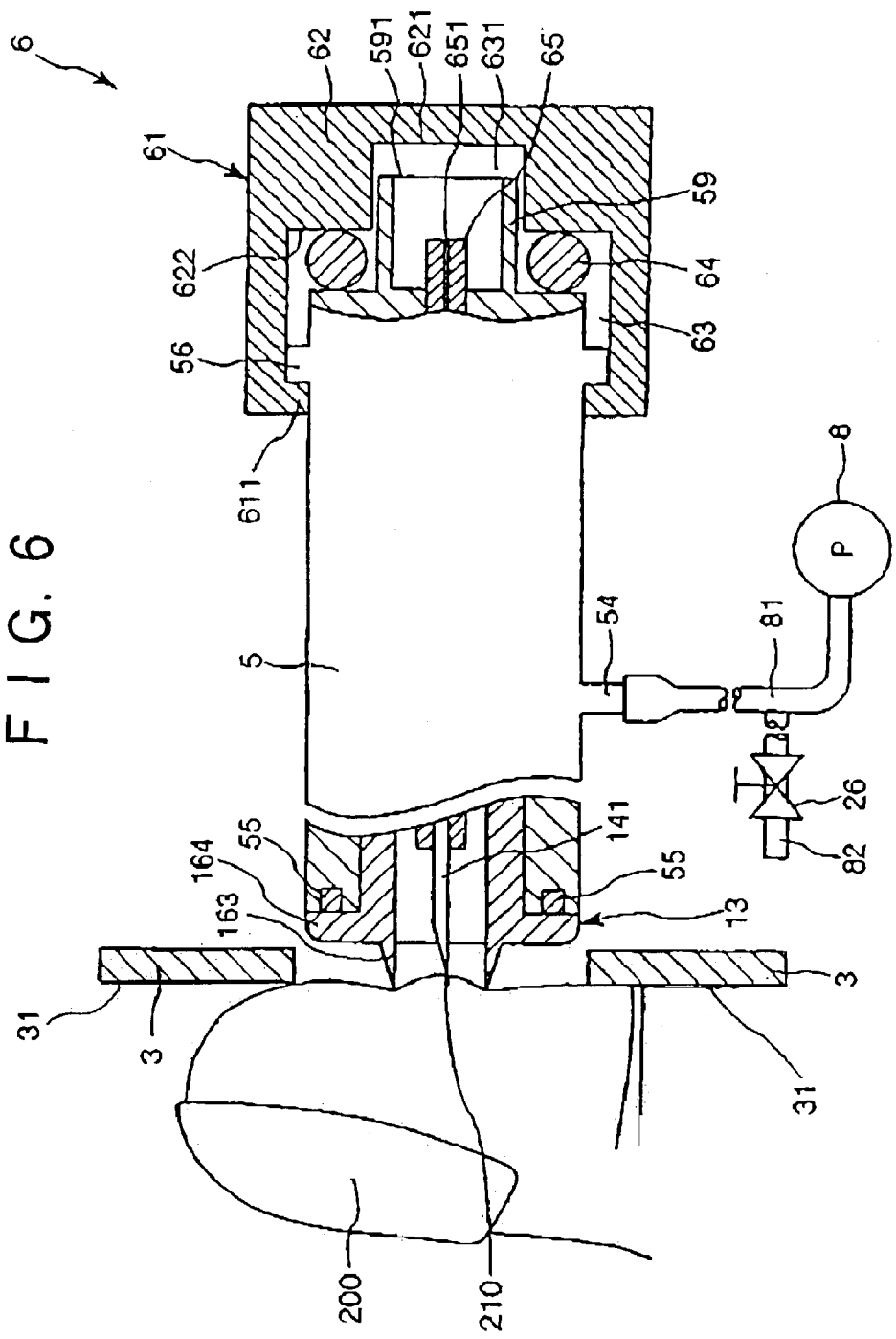
FIG. 6 is a vertical sectional view showing the configuration example of the essential portions of the body fluid component measuring apparatus according to the first embodiment (in a state at the time of operation of the puncturing means)
Figure 7:
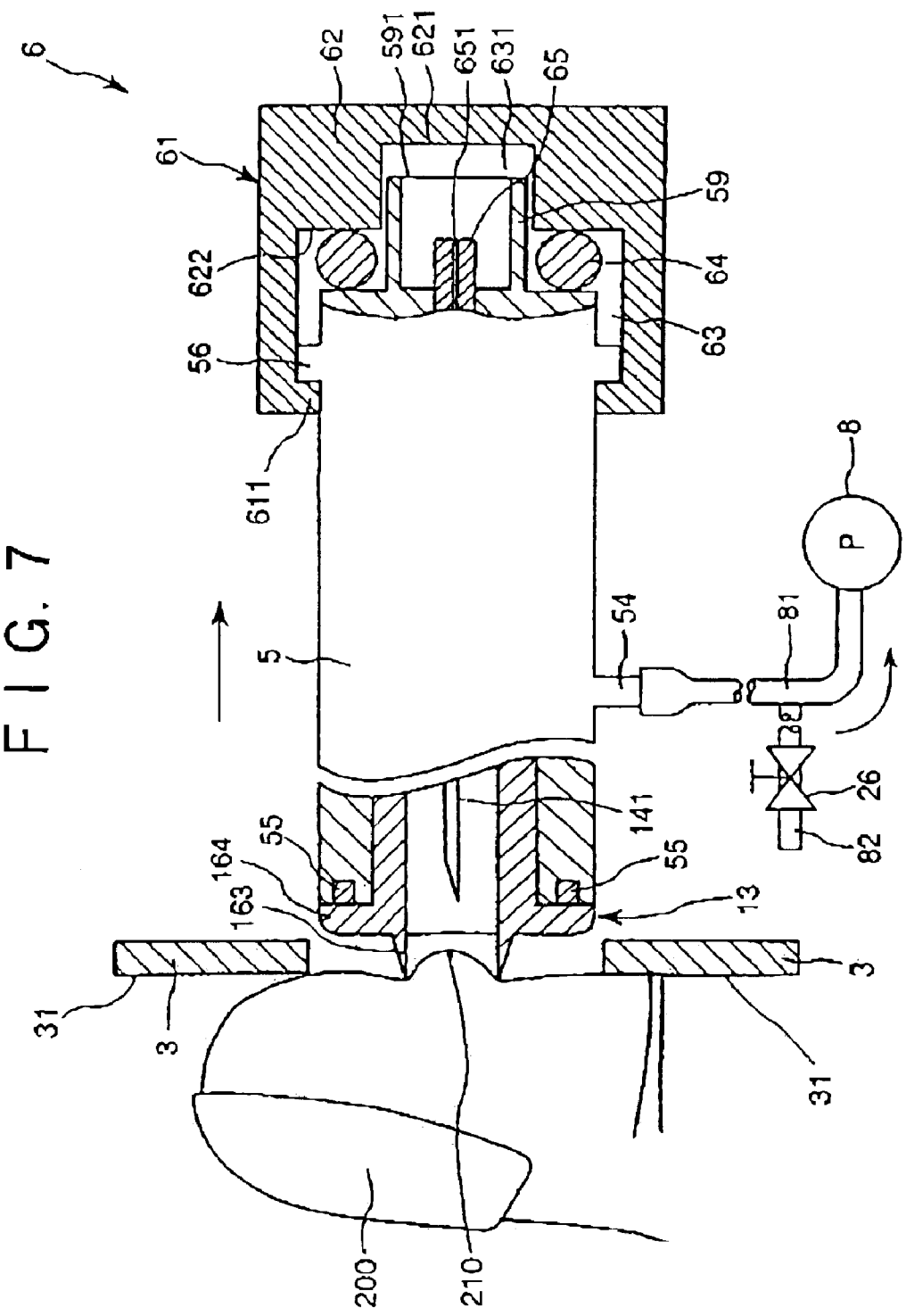
FIG. 7 is a vertical sectional view showing the configuration example of the essential portions of the body fluid component measuring apparatus according to the first embodiment (in a state at the time of operation of an evacuating means)

According to the body fluid component measuring apparatus 1, as shown in FIG. 6, when the finger tip 200 is touched to the touch portion 3, the surface of the finger tip 200 comes into contact with the tip of the contact portion 163, with a result that blood capillaries of a portion around the puncture site 210 are compressed by the contact portion 163; however, since the chip 13 can be separated from the finger tip 200 while the puncture site 210 of the finger tip 200 is kept in the evacuation state, the blood capillaries of the portion around the puncture site 210, which have been compressed by the tip of the contact portion 163, are released. As a result, the blood, which is denoted by reference numeral 220 in FIG. 8, can be more certainly sucked from the puncture site 210 for a short time, and thereby an amount of blood necessary for measurement of an amount of glucose can be sufficiently sampled.

In the operational state of the chip withdrawing mechanism 6 (the state shown in FIG. 8), the housing 5 is moved in the direction toward the base end, to compress the seal ring 64. Since the seal ring 64 is formed of an elastic body as described above, in the state shown in FIG. 8, the seal ring 64 urges the housing 5 in the direction toward the tip side. Accordingly, by the opening the electromagnetic valve 26 to release the evacuation state, the seal ring 64 is returned nearly to the original shape by the self-elastic force to move the housing 5 in the direction toward the tip side (see FIGS. 9 and 10) In this case, after the tip of the flange 56 of the housing 5 comes into contact with the base end of the projection 611 of the main body portion 61, the tip of the flange 56 is no longer moved in the direction toward the tip side (see FIG. 10). In this way, the housing 5 and the chip 13 mounted thereto are returned to the positions in the state before the operation of the chip withdrawing mechanism 6.

Actions of respective constituent elements and control operations of the control means in the case of puncturing the finger tip, sampling blood therefrom, diffusing the blood in the test paper, and measuring a blood sugar level by using the body fluid component measuring apparatus will be described below with reference to the configurations of the constituent elements shown in FIGS. 2 to 10 and a flow chart shown in FIG. 12.

[1] The chip 13 is inserted in the fitting portion 53 of the housing 5 via the opening 212 of the housing body 21, and the small-diameter portion 143 of the puncture needle 14 is fitted in the needle holder 411 (see FIG. 4).

The chip 13 is further pressed in the direction toward the base end side, to push the plunger 41 against the urging force of the coil spring 42 in the direction toward the base end side. Along with the movement of the plunger 41, the locking portion 413, which is in contact with the inner peripheral surface of the bore portion 52 while being urged by the elastic force of the elastic piece 412, is moved in the direction toward the base end side. When reaching the position of the opening 57, the locking portion 413 is inserted in the opening 57 (see FIG. 4). In this state, even if the pressing force of the chip 13, which force is applied to the plunger 41 in the direction toward the base end side, is released, the movement of the plunger 41 in the direction toward the tip side is restricted by locking of the locking portion 413 with the opening 57. At this time, the coil spring 42 is in the compression state. The preparation of puncturing the finger tip with the puncturing means 4 and the preparation of sampling blood (specimen) are thus accomplished.

[2] The power switch (not shown) is turned on, to activate the constituent elements of the body fluid component measuring apparatus 1, thereby bringing them into measurable states. In this state, the electromagnetic valve 26 remains closed.

[3] The finger tip (finger) 20 is touched to the touch portion 3, so that the finger tip 200 is brought into press-contact with the contact portion 163 of the chip 13. At this time, the tip opening 162 may be blocked with the finger tip 200 in such a manner as to make the leakage of air as small as possible (see FIG. 5).

[4] The operating button 222 is depressed, to cause the needle body 141 to puncture the surface of the finger tip 200 (step S1 in FIG. 12).

When the operating button 222 is depressed, the locking releasing member 223 connected to the operating button 222 is moved downwardly in FIG. 4. The locking releasing member 223 is thus brought into contact with the locking portion 413, to push down the locking portion 413 into the bore portion 52. As a result, the locking of the locking portion 413 is released, to allow the plunger 41 to be moved in the direction toward the tip side by the elastic force of the compressed coil spring 42, so that the needle body 141 projects from the tip opening 162 to puncture the surface of the finger tip 200 (see FIG. 6). Blood flows out of the puncture site 210 punctured by the needle body 141.

An operating switch (not shown) of the pump 8 is turned on nearly simultaneously with the above-described depressing operation of the operating button 222.

[5] After the finger tip 200 is punctured by the needle body 141, the plunger 41 is pushed back in the direction toward the base end side by the elastic force of the coil spring 43. The movement of the plunger 41 is attenuated, and finally the plunger 41 is rested at the position where the elastic force of the coil spring 43 is balanced against the elastic force of the coil spring 42 (see FIG. 7). At this time, the cutting edge of the needle body 141 is in the state being housed in the chip 13. In this way, the edge of the needle body 141 does not project from the tip opening 162 except that it is used for puncture of the finger tip, to thereby eliminate erroneous damages of the skin of the finger tip and preventing infection via the needle body 141. The body fluid component measuring apparatus 1 is thus advantageous in carrying out the sampling of blood with a high safety.

[6] On the basis of the turn-on of the operating switch of the pump 8, the pump 8 is operated by the control means (see step S2 in FIG. 12).

To be more specific, the pump 8 is operated nearly simultaneously with the operation described in the item [4], to start suction of air in the bore portion 52 of the housing 5, thereby reducing the pressure in the bore portion 52 (including the interior of the chip 13) The bore portion 52 is thus brought into the evacuation state.

At this time, the puncture site 210, punctured by the needle body 141, of the finger tip 200 is also brought into the evacuation state. In this state, however, a portion, positioned inside the contact portion 163 (tip opening 162), of the finger tip 200 is inwardly swelled in a round shape in the chip 13, with a result that blood capillaries at a portion around the puncture site 210 being in contact with the tip of the contact portion 163 are compressed.

[7] Along with continuation of the suction of the bore portion 52 by the pump 8, air in the volume variable chambe are gradually released, with a result that blood 220 is sucked from the puncture site 210 (see FIG. 8). In this way, as compared with a configuration that the chip 13 is not separated from the finger tip 200, the flow of the blood is promoted. This is advantageous in sampling a necessary amount of blood for a short time.

It is preferable to set the minimum pressure caused by the pump 8 in a range of about 100 to 400 mmHg.

The base end 591 of the projection 59 is eventually brought into contact with the bottom surface of the recess 621, to stop the movement of the housing 5 and the chip 13 mounted thereto in the direction toward the base end side. Since the chip 13 is stopped after being separated from the finger tip 200 by an appropriate distance, the finger tip 200 is prevented from being separated from the tip opening 162. This certainly prevents occurrence of an inconvenience that the blood 220 sucked from the puncture site 210 be scattered to contaminate the surroundings. In this way, the body fluid component measuring apparatus 1 is advantageous in sampling blood with a high safety.

As described above, according to the body fluid component measuring apparatus 1, the puncturing operation and the evacuating operation are nearly simultaneously performed by only one depressing operation of the operating button 222, the withdrawing action of the chip 13 is performed by making use of the evacuated pressure caused by the pump 8, and the evacuation releasing action (to be described later) is automatically started. The body fluid component measuring apparatus 1, therefore, is very excellent in its operability.

[8] The blood 220 raised in a granular shape from the puncture site 210 as a result of the operation described in the item [7] is sucked in the chip 13, to be brought into contact with the blood introducing guide 166 formed in the chip 13. The blood 220 is then introduced to the test paper 18 via the blood passage 19, being supplied to the center portion of the test paper 18, and is diffused radially in the test paper 18 (see FIG. 2).

Along with the supply and diffusion of the blood 220 on and in the test paper 18, glucose (component to be measured) in the blood 220 reacts with the reagent supported by the test paper 18, with a result that the test paper 18 is colored to a degree depending on the amount of glucose.

On the other hand, after executing step S2 shown in FIG. 12, the control means 11 drives the measuring means 7, to monitor the coloring of the test paper 18 via the measuring means 7, thereby deciding whether or not the blood has been sampled (step S3 in FIG. 12).

In step S3, if the voltage level of a signal inputted from the light receiving device 72 of the measuring means 7 is more than a predetermined threshold value, it is decided that the blood has been sampled, and it the voltage level of the above signal is equal to or less than the threshold value, it is decided that the blood has been not sampled.

The threshold value is set to a value sufficiently larger than a voltage level of the signal before coloring of the test paper 18 and sufficiently smaller than a voltage level of the signal at the time of coloring of the test paper 18.

If it is decided in step S3 that the blood has been not sampled, it is decided whether or not a predetermined time has elapsed (step S4 in FIG. 12).

If it is decided in step S4 that the predetermined time has not elapsed, the process is returned to step S2 to execute steps S2 and S3 again, whereas if it is decided in step S4 that the predetermined time has elapsed, an error processing is executed (step S5 in FIG. 12).

In step S5, the pump 8 is stopped to open the electromagnetic valve 26, thereby releasing the evacuation state, and also an error indication is displayed on the display unit 12.

Such an error indication allows the operator (user) to comprehend that an error (trouble) has occurred during operation.

It is to be noted that the function by opening the electromagnetic valve 26 will be fully described later.

If it is decided in step S3 that the blood has been sampled, the pump 8 is stopped (step S6 in FIG. 12).

The electromagnetic valve 26 is opened to release the evacuation state (step S7 in FIG. 12).

Figure 9:
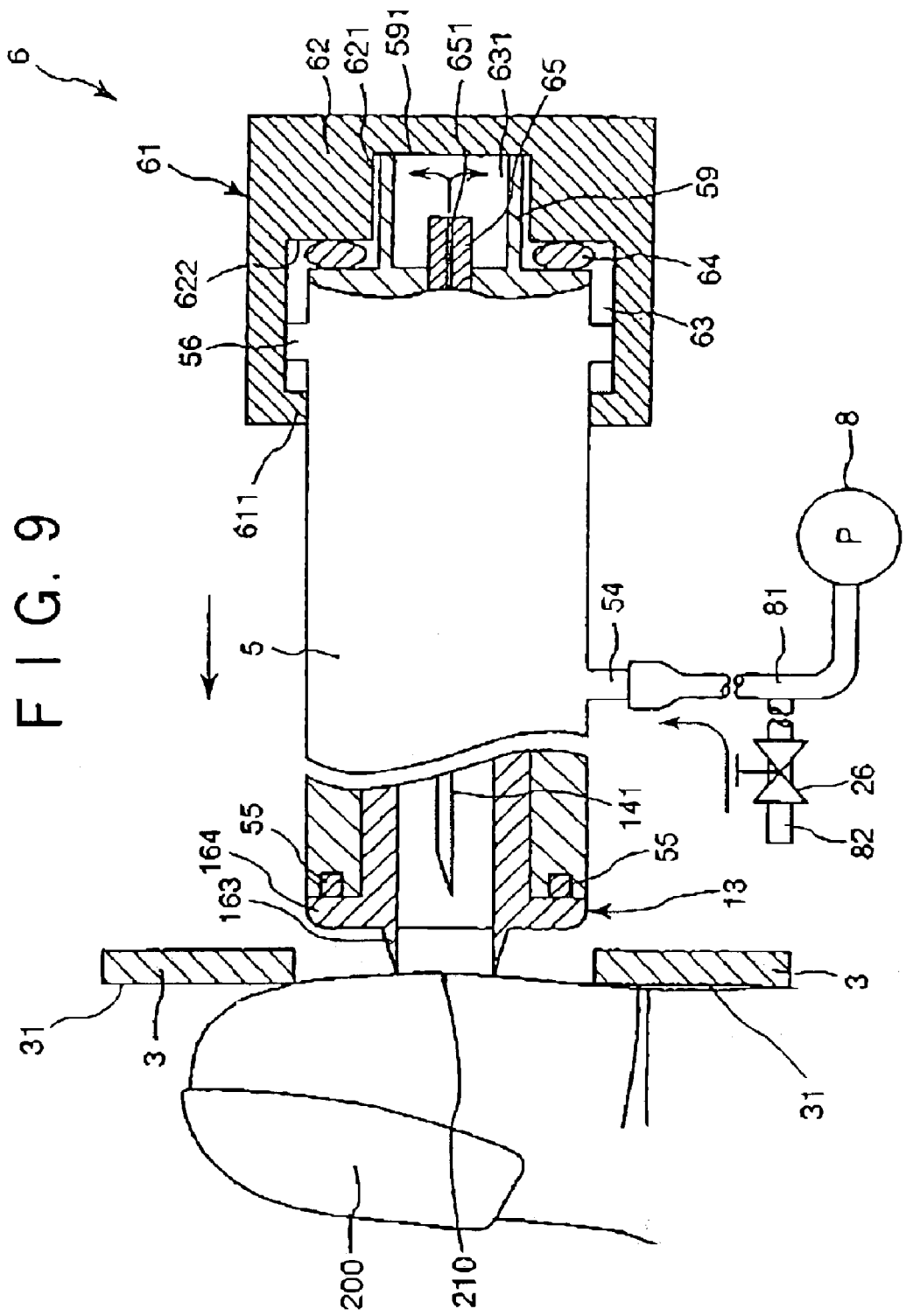
FIG. 9 is a vertical sectional view showing the configuration example of the essential portions of the body fluid component measuring apparatus according to the first embodiment (in a state at the time of operation of an evacuation releasing means)

When the electromagnetic valve 26 is opened, outside air (atmospheric air) flows in the bore portion 52 (including the interior of the chip 13) and the puncture site 210 via the tubes 82, 81 and the ventilation passage 54, whereby the pressure in the bore portion 52 (including the interior of the chip 13) and the puncture site 210 is returned to atmospheric air (see FIG. 9).

Figure 10:
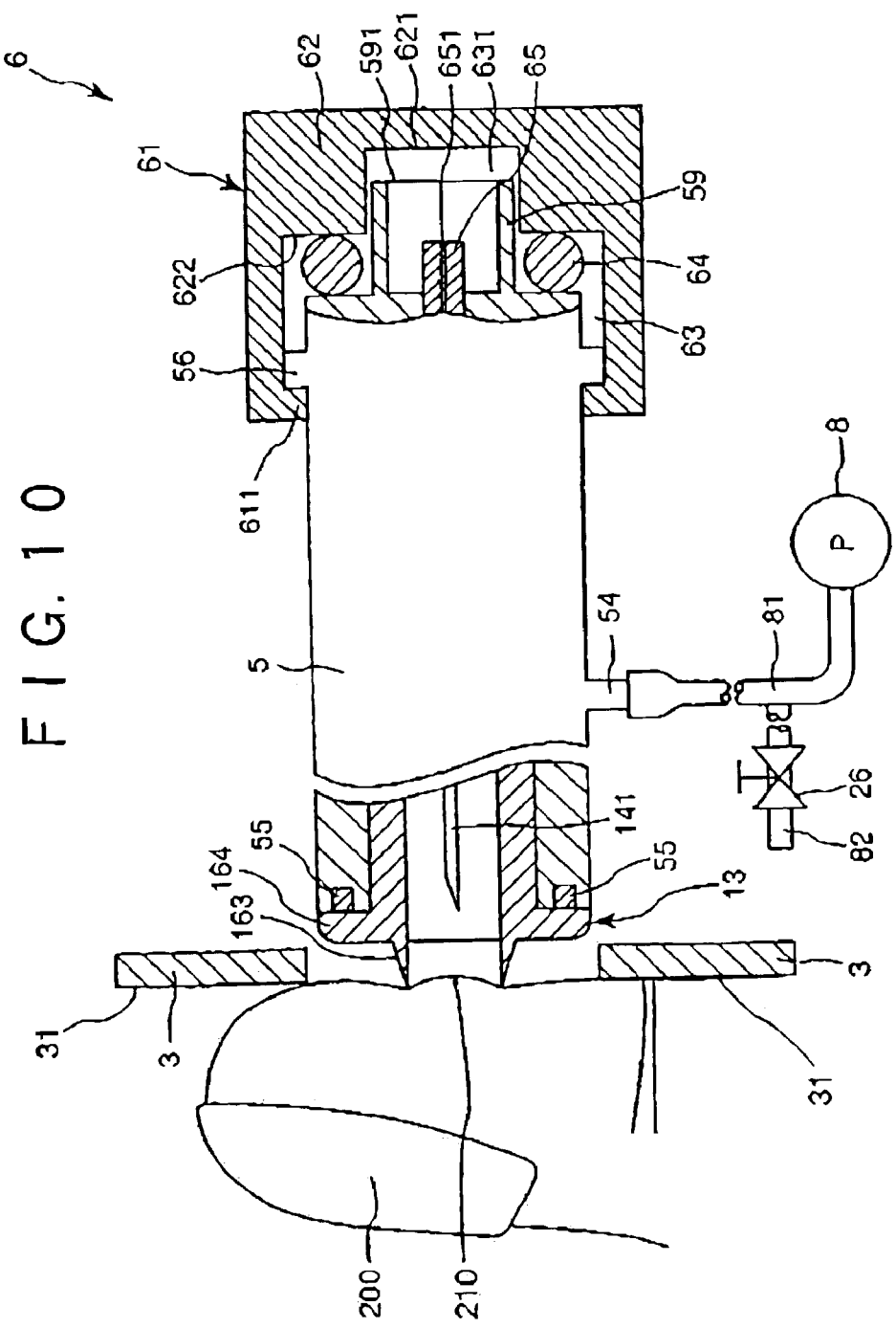
FIG. 10 is a vertical sectional view showing the configuration example of the essential portions of the body fluid component measuring apparatus according to the first embodiment (in a final state)

The seal ring 64 is also nearly returned to the original shape by the self-elastic force, to move the housing 5 in the direction toward the tip side (see FIGS. 9 and 10). After a while, the tip of the flange 56 of the housing 5 is brought into contact with the base end of the projection 611 of the main body portion 61, to restrict the movement of the housing 5 in the direction toward the tip side (see FIG. 10).

When the operator becomes insensible of suction at the portion, around the puncture site 210, of the finger tip 200 and thereby recognizes that the internal pressure is returned to atmospheric pressure, he or she separates the finger tip 200 from the contact portion 163 of the chip 13.

[9] After executing step S7 shown in FIG. 12, the control means 11 causes the measuring means 7 to measure the degree of coloring of the test paper 18, executes arithmetic operation based on the data thus obtained, and performs correcting calculation such as temperature correcting calculation or hematocrit value correcting calculation, to quantify the blood sugar level (step S8 in FIG. 12).

In this case, since the evacuation state of the bore portion 52 (including the interior of the chip 13), that is, the evacuation state of the housing space of the test paper 18 is released, a component in atmospheric air necessary for reaction between glucose (component to be measured) in the blood 220 and the reagent supported by the test paper 18 can be sufficiently supplied to the test paper 18, whereby the blood sugar level can be accurately measured.

The blood sugar level thus calculated is displayed on the display unit 12 (step S9 in FIG. 12).

The operator can thus confirm his or her blood sugar level from the value displayed on the display unit 12.

As described above, according to the body fluid component measuring apparatus 1, it is possible to certainly sample a sufficient amount of blood necessary for measurement for a short time and to accurately, certainly measure the blood sugar level (amount of a specific component in blood).

Since the test paper 18 is provided on the chip 13, it is possible to continuously perform the puncture of the finger tip, sampling of blood, diffusion of blood in the test paper 18, and measurement (quantitative determination) of blood, and hence to easily measure the blood sugar level (component) in blood for a short time.

Since the preparation for operating the body fluid component measuring apparatus 1 is facilitated, the apparatus 1 is advantageous for periodical or repeated use thereof.

According to the body fluid component measuring apparatus 1, it is possible to prevent occurrence of an accident such as erroneous puncture of the skin of the operator again after puncture necessary for sampling of blood, and hence to sample blood with a high safety. The apparatus 1 is also advantageous in that the operator can use the apparatus 1 with less sensation of fear against puncture because the puncture needle 14 is out of the eyeshot of the operator.

Accordingly, the body fluid component measuring apparatus 1 is suitable for the operator (patient) to measure his or her blood sugar level.

The body fluid component measuring apparatus 1 is advantageous in terms of simple configuration, small size and light weight, low cost, and suitability for mass-production.

A second embodiment of the body fluid component measuring apparatus according to the first aspect of the present invention will be described below. The body fluid component measuring apparatus according to the second embodiment is different from the above-described body fluid component measuring apparatus 1 according to the first embodiment in configuration of the evacuation releasing means.

Figure 13:
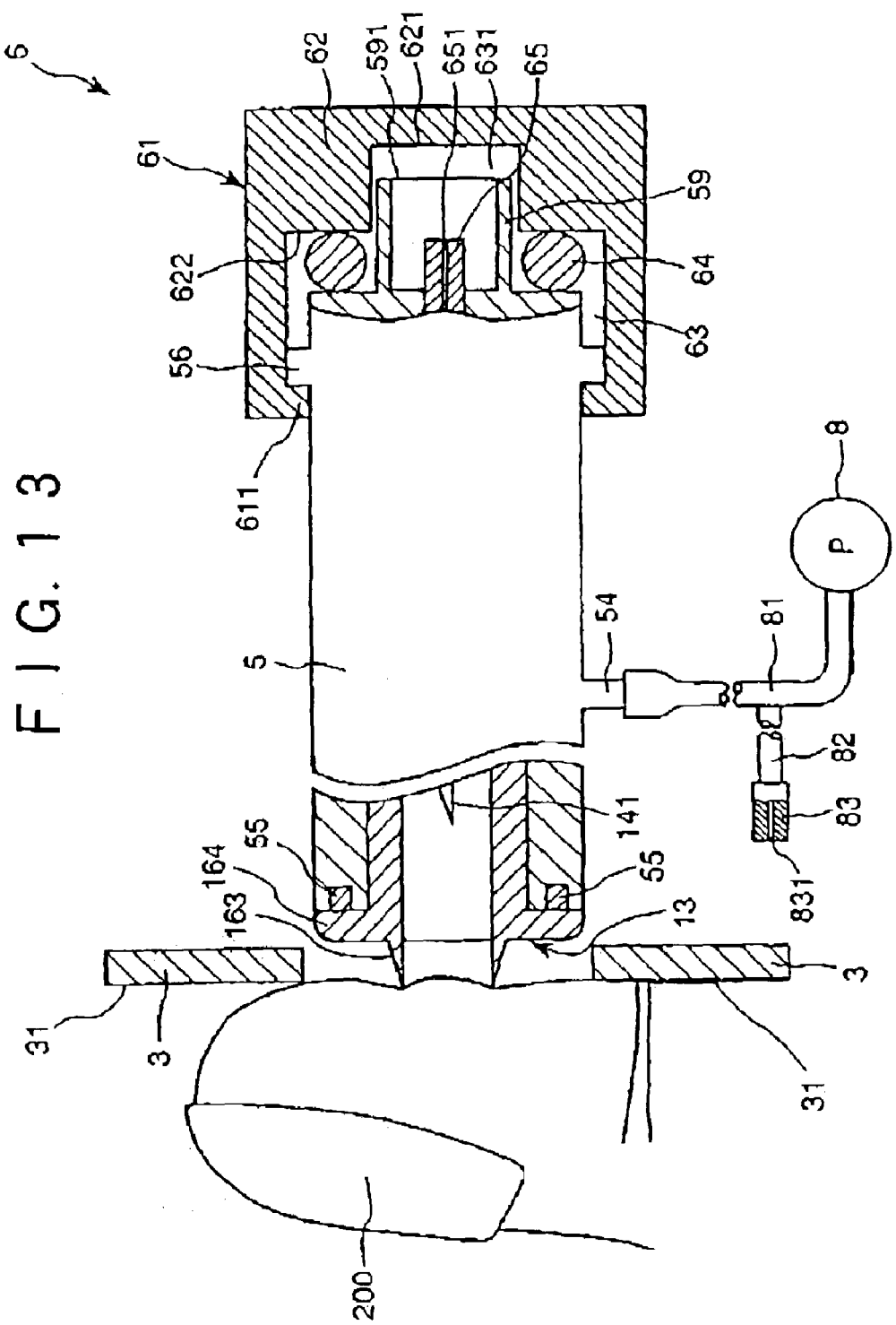
FIG. 13 is a vertical perspective view showing essential portions of a second embodiment of the body fluid component measuring apparatus according to the present invention;.
Figure 14:
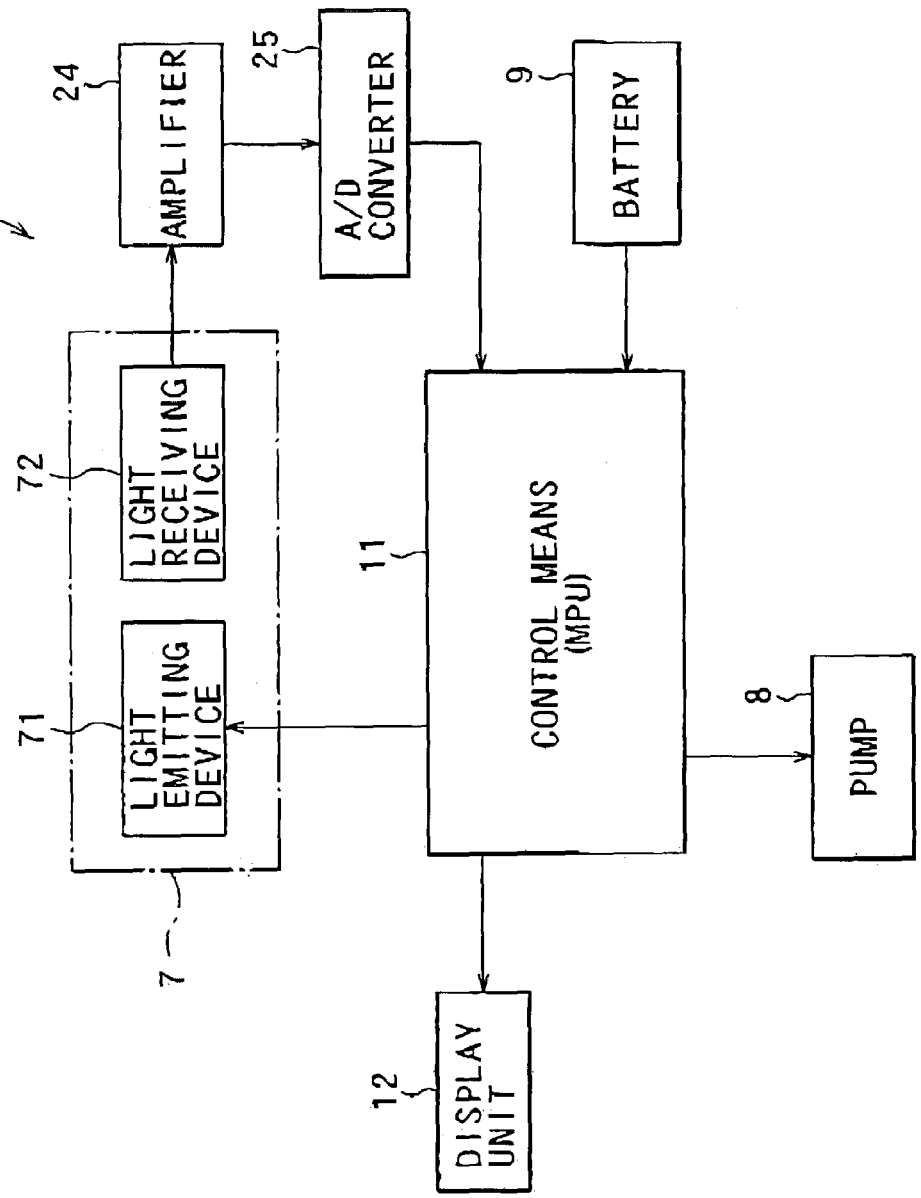
FIG. 14 is a block diagram showing a circuit configuration of the body fluid component measuring apparatus according to the second embodiment.

FIG. 13 is a vertical sectional view showing a configuration of essential portions of the body fluid component measuring apparatus according to the second embodiment, and FIG. 14 is a block diagram showing a circuit configuration of the body fluid component measuring apparatus according to the second embodiment.

The body fluid component measuring apparatus according to the second embodiment will be described, principally, about different points from the body fluid component measuring apparatus 1 according to the first embodiment, with the overlapped description of the same constituent elements as those of the body fluid component measuring apparatus 1 according to the first embodiment being omitted. It is to be noted that FIG. 13 is depicted with the "base end side" of the apparatus taken as the right side and the "tip side" of the apparatus taken as the left side.

As shown in FIGS. 13 and 14, in the body fluid component measuring apparatus 1 according to the second embodiment, a fine tube 83 is provided in place of the electromagnetic valve 26 of the above-described body fluid component measuring apparatus 1 according to the first embodiment.

The fine tube 83 is formed of a cylindrical member and internally has an orifice (flow passage) 831. The fine tube 83 is connected to an end portion of the tube 82, and the tip of the fine tube 83 (orifice 831) is opened to the outside of the main body 21.

The orifice 831 of the fine tube 83 is required to be narrow enough to keep a large passing resistance of air. The diameter of the orifice 831 is not particularly limited but is preferably in a range of about 0.01 to 0.3 mm. The length of the orifice 831 is not particularly limited but is preferably in a range of about 5 to 15 mm. By setting the diameter of the orifice 831 within the above range, it is possible to certainly keep the necessary passing (flow) resistance of air.

An evacuation releasing means is composed of the tubes (flow passage) 81, 82 and the fine tube 83.

It is to be noted that the fine tube 83 is not limited to that shown in the figure, and although only one fine tube 83 is provided in this embodiment, a plurality of fine tubes (orifices) may be provided if needed.

The operation of the body fluid component measuring apparatus 1 will be described below with reference to the flow chart shown in FIG. 12, principally, about the different points from the above-described body fluid component measuring apparatus 1 according to the first embodiment.

First, steps S1 to S6 shown in FIG. 12 are executed nearly in the same manner as that described for the above-described body fluid component measuring apparatus 1 according to the first embodiment.

In operation of the body fluid component measuring apparatus 1 according to this embodiment, since the flow rate of air sucked by the pump 8 is larger than the flow rate of outside air (atmospheric air) flowing from the orifice 831 of the fine tube 83, when the pump 8 is operated in step S2, the suction of air in the bore portion 52 of the housing 5 is started, whereby the pressure in the bore portion 52 (including the interior of the chip 13) is reduced, to thereby bring the bore portion 52 into an evacuation state.

In the body fluid component measuring apparatus 1 according to this embodiment, when the pump 8 is stopped in step S6, outside air (atmospheric air) flows in the bore portion 52 (including the interior of the chip 13) and the puncture site 210 via the orifice 831 of the fine tube 83, the tubes 82 and 81, and the ventilation passage 54, to release the evacuation state of the bore portion 52 (including the interior of the chip 13) and the puncture site 210 (step S7 in FIG. 12). The pressure in the bore portion 52 (including the interior of the chip 13) and the puncture site 210 is thus returned to atmospheric pressure.

The subsequent steps S8 and S9 shown in FIG. 12 are executed in the same manner as that described for the body fluid component measuring apparatus 1 according to the first embodiment.

The body fluid component measuring apparatus 1 according to this embodiment can obtain the same effect as that obtained by the above-described body fluid component measuring apparatus 1 according to the first embodiment.

While the body fluid component measuring apparatus according to the first aspect of the present invention has been described on the basis of the first and second embodiments shown in the figures, the present invention is not limited thereto. For example, the configuration of each of the constituent elements described in the embodiments may be replaced with any configuration exhibiting the same function.

The component to be measured is represented by glucose (blood sugar level) in the embodiments; however, according to the present invention, the component to be measured is not limited thereto but may be exemplified by protein, cholesterol, uric acid, creatinine, alcohol, or ions of an inorganic matter such as sodium.

The means (called "measuring means") used as not only as the blood sampling detecting means for detecting the sampling of blood but also as the measuring means for measuring an amount of a specific component in blood is provided in the embodiments; however, according to the present invention, the blood sampling detecting means and the measuring means may be separately provided.

The blood sampling means is represented by the means for optically detecting the sampling of blood in the embodiments; however, according to the present invention, the blood sampling means is not limited thereto but may be configured as a means for electrically detecting the sampling of blood.

In the case of adopting the blood sampling detecting means for optically detecting the sampling of blood, the detection of the sampling of blood is not necessarily based on the manner described in the embodiments, that is, the manner of detecting the coloring (color development) of the test paper due to reaction between the component in blood and the reagent but may be based on a manner of detecting the introduction of blood in the blood passage (blood flow passage) for supplying blood to the test paper provided on the chip.

In the case of adopting the manner of detecting the introduction of blood in the blood passage, a portion, at least in the vicinity of the blood passage, of the chip may be formed of a member having a light permeability (transparency), and further, the blood sampling detecting means may be configured to emit light to the blood passage via the transparent member, receive the reflected light or transmitted light, and convert the light into an electric signal, and the control means may be configured to monitor a voltage outputted from the blood sampling detecting means. If blood is introduced in the blood passage, the color of a portion, through which the blood passes, of the blood passage is changed into nearly dark-red, to change the quantity of the reflected light or the transmitted light thereat, thereby changing a voltage outputted from the blood sampling detecting means. As a result, the sampling of blood can be detected on the basis of the change in voltage (quantity of light) outputted from the blood sampling detecting means.

The blood sampling detecting means for electrically detecting the sampling of blood is exemplified by a sensor (electrode) for detecting (measuring) an impedance of the blood passage or the like of the chip, or a bio-sensor.

In the case of adopting the bio-sensor, since a current outputted from the bio-sensor is changed if blood is introduced in the blood passage, the sampling of blood can be detected on the basis of the change in current (current value) outputted from the bio-sensor.

In the case of adopting the sensor for detecting an impedance of the blood passage, since an impedance between the electrodes of the sensor, provided across the blood passage, is changed if blood is introduced in the blood passage, the sampling of blood can be detected on the basis of the change in impedance of the blood passage.

The body fluid component measuring apparatus in each of the embodiments is configured by optically measuring the degree of the coloring of the test paper caused by reaction between the component in blood and the reagent, and converting the measured result into a value to be displayed on the display unit; however, the present invention is not limited thereto. For example, the measuring apparatus may be configured by electrically measuring a change in potential caused depending on an amount of a component in blood (specimen), and converting the measured result into a value to be displayed on the display unit.

The measurement method in each of the embodiments is configured so as to release the evacuation state prior to measurement; however, according to the present invention, the method may be configured so as to relieve the evacuation state prior to measurement.

According to the present invention, the actions of the evacuation means and the chip withdrawing mechanism may be started either in a manual manner or in an automatic manner, respectively. In the case of adopting the automatic manner, a sensor for magnetically sensing the movement of the puncture needle in the direction toward the tip side at the time of puncture may be disposed in the vicinity of a side portion of the fitting portion of the housing. In this case, the evacuation means and the chip withdrawing means can be automatically moved on the basis of information supplied from the sensor.

A body fluid component measuring apparatus according to a second aspect of the present invention will be hereinafter described in detail on the basis of preferred embodiments shown in the accompanying drawings.

It is to be noted that FIGS. 1 and 2, FIG. 5, FIGS. 7 to 10, and FIG. 13 used for the following description are the same drawings as those used for description of the body fluid component measuring apparatus according to the first aspect of the present invention.

Figure 15:
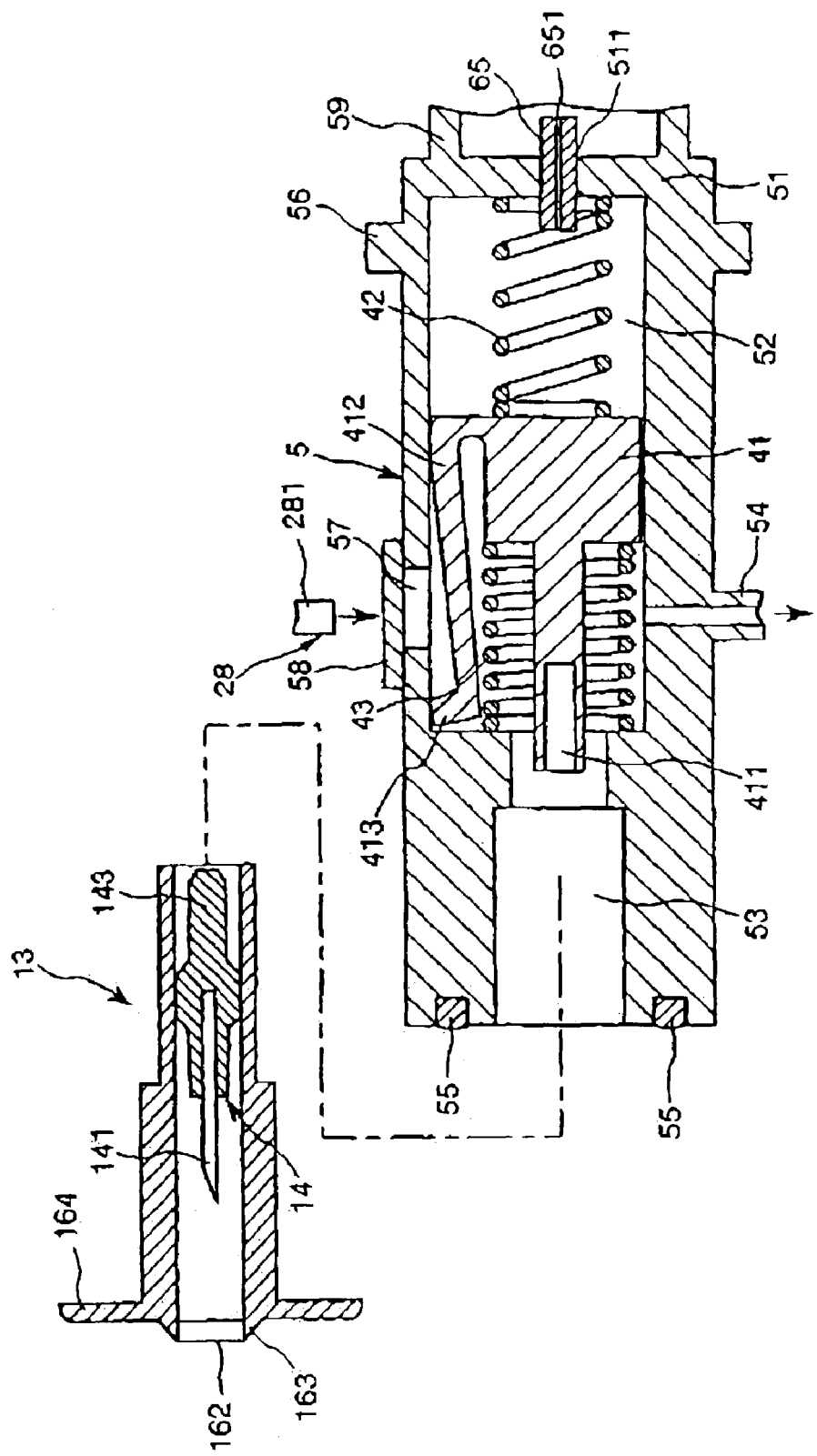
FIG. 15 is a vertical sectional view showing a configuration examples of a puncturing means and a housing for housing the puncturing means in the body fluid component measuring apparatus according to a first embodiment of a second aspect of the present invention (in a state before the chip is mounted to the housing)
Figure 16:
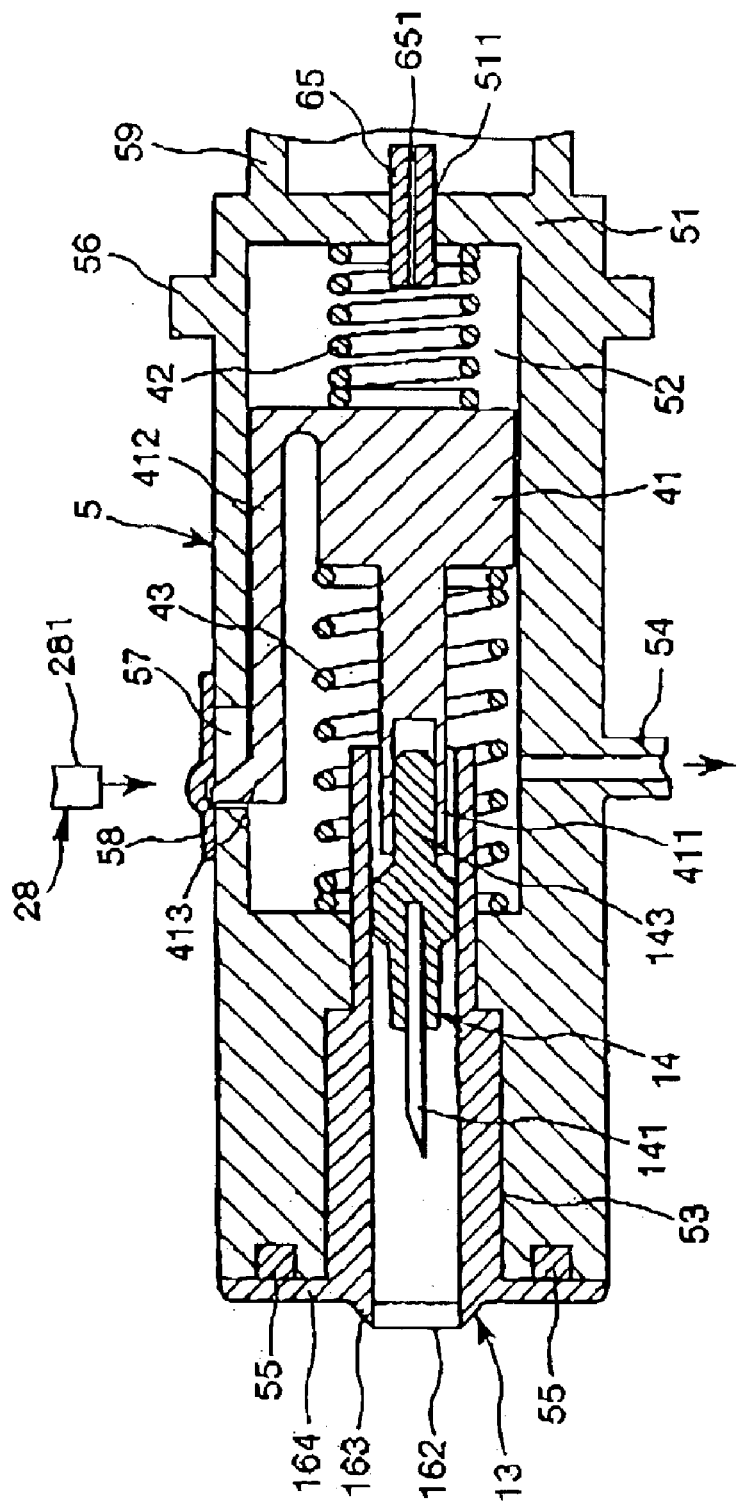
FIG. 16 is a vertical sectional view showing the configuration examples of the puncturing means and the housing for housing the puncturing means in the body fluid component measuring apparatus according to the first embodiment of the second aspect of the present invention (in a state that the chip is mounted to the housing)
Figure 19:
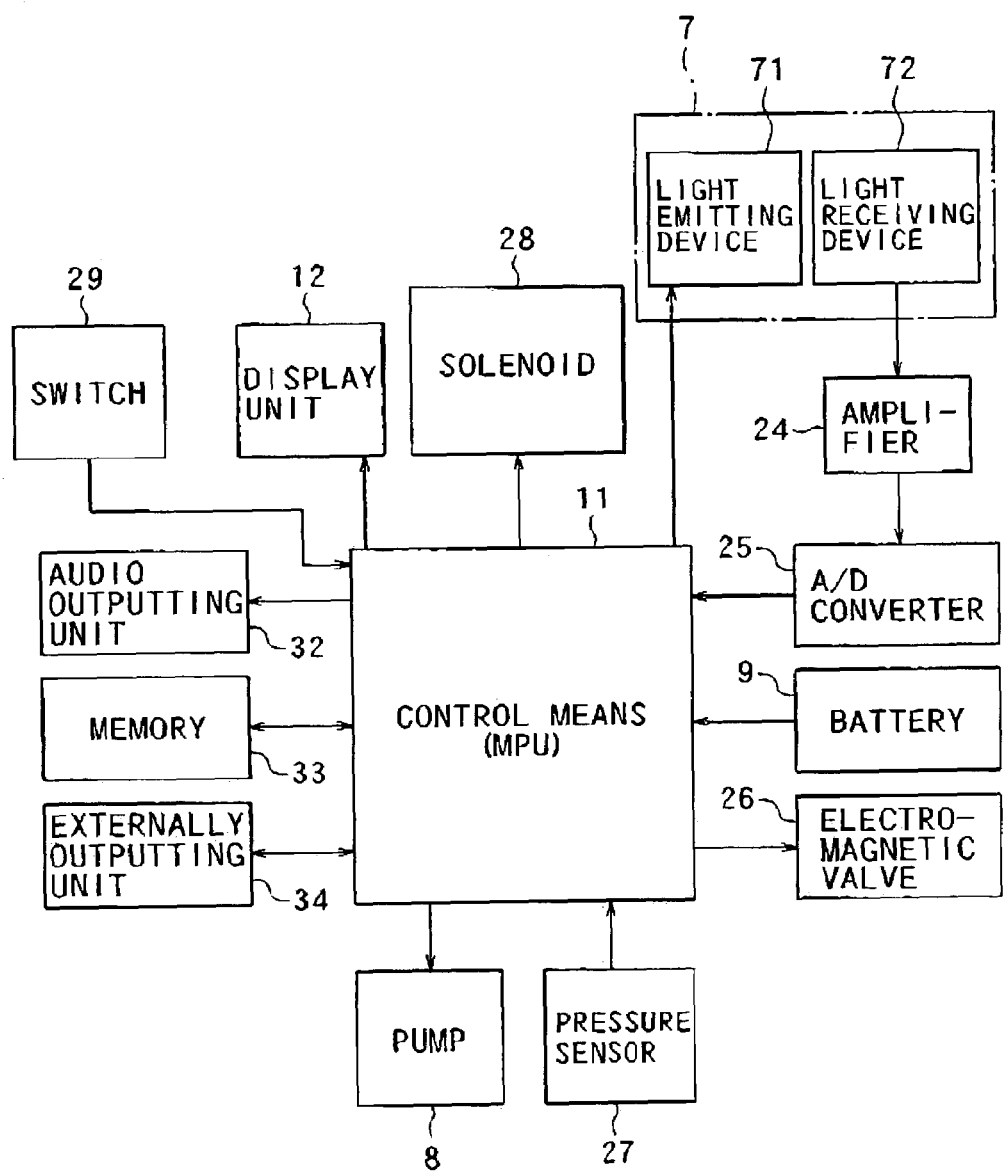
FIG. 19 is a block diagram showing a circuit configuration of the body fluid component measuring apparatus according to the first embodiment of the second aspect of the present invention.
Figure 20:
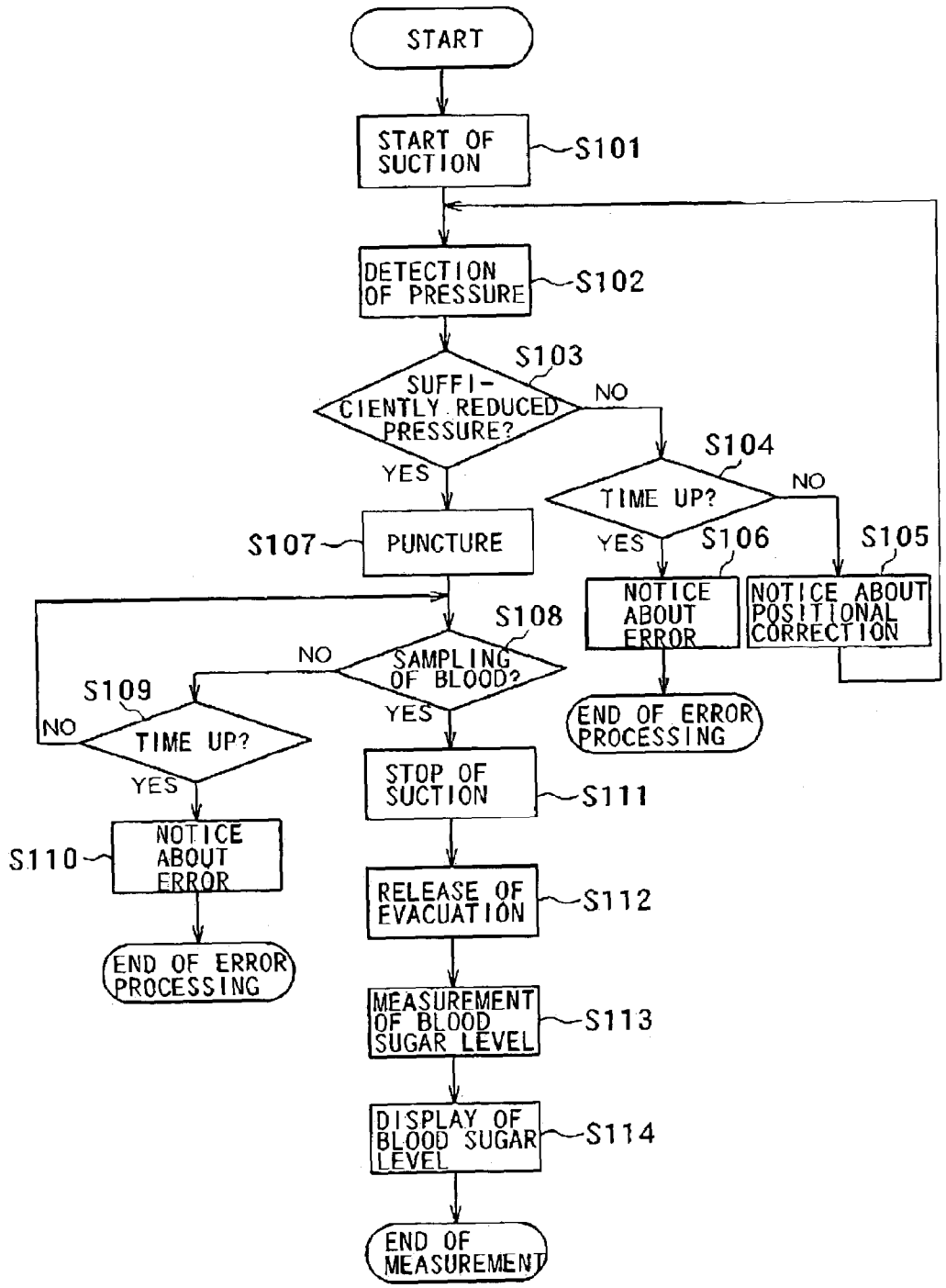
FIG. 20 is a flow chart showing a control operation of a control means for the body fluid component measuring apparatus according to the first embodiment of the second aspect of the present invention.

FIGS. 15 and 16, equivalent to FIGS. 3 and 4 used for description of the apparatus according the first aspect, are vertical sectional views showing configuration examples of a puncturing means and a housing for housing the puncturing means in the body fluid component measuring means according to a first embodiment of the second aspect (hereinafter, referred to simply as "first embodiment" with the word "second aspect" omitted, respectively; FIG. 5, FIGS. 7 to 11, and FIGS. 17 and 18 are vertical sectional views showing configuration examples of essential portions of the body fluid component measuring apparatus according to the first embodiment; FIG. 19 is a block diagram showing a circuit configuration of the body fluid component measuring apparatus according to the first embodiment; and FIG. 20 is a flow chart showing a control operation of a control means for the body fluid component measuring apparatus according to the first embodiment. In these figures, parts being identical or similar to those shown in FIGS. 1 to 14 are denoted by the same reference numerals.

It is to be noted that these drawings are depicted with the "base end side" of the apparatus taken as the right side and the "tip side" of the apparatus taken as the left side.

As shown in FIGS. 1, 5 and 19, a body fluid component measuring apparatus (blood component measuring apparatus) 1 according to the first embodiment includes a main body 2, a finger touch portion 3 disposed on the main body 2, a puncturing means 4 housed in a housing 5, a chip withdrawing mechanism 6 provided on the base end side of the housing 5, a measuring means 7 for detecting the sampling of blood (body fluid) and measuring a specific component in the sampled blood (body fluid), a pump 8 for evacuating the interior of the housing 5, an electromagnetic valve 26 for releasing, relieving, or holding an evacuation state of the interior of the housing 5, a pressure sensor (pressure detecting means) 27 for detecting the pressure in the housing 5, a solenoid (drive source) 28, a switch 29, a battery (power source) 9, a control means 11 and a memory 33 provided on a circuit board 10, a display unit (notifying means) 12, an audio outputting unit (notifying means) 32, and an externally outputting unit 34.

At time of use, the above-described chip 13 shown in FIG. 2 is mounted to the body fluid component measuring apparatus 1. Each of constituent elements of the apparatus 1 will be described below.

The main body 2 is composed of a housing body 21 and a lid body 22, which are disposed opposite to each other. The main body 2 internally has a housing space 23, in which the puncturing means 4, the housing 5, the chip withdrawing mechanism 6, the measuring means 7, the pump 8, the electromagnetic valve 26, the solenoid 28, the switch 29, the battery 9, the circuit board 10, the control means 11, the memory 33, the display unit 12, the audio outputting unit 32, and the externally outputting unit 34 are housed. The pressure sensor 27 is disposed in the housing 5.

A wall portion 211 on the tip side of the housing body 21 has an opening 212 passing through the housing body 21. The opening 212 has a circular shape in cross-section. The chip 13 is mounted (held) to the housing 5 (to be described later) via the opening 212.

The finger touch portion 3 (to which the epidermis is to be touched) is provided on a plane on the tip side of the wall portion 211 so as to surround the outer periphery of the opening 212. The finger touch portion 3 has a shape corresponding to that of the finger tip (finger). A finger touch plane 31 is formed on the tip side of the finger touch portion 3. The operator (user) operates the body fluid component measuring apparatus 1 while touching the finger tip to the finger touch portion 3 (finger touch plane 31). With such an operation of the apparatus 1, the finger tip is punctured, blood is sampled therefrom, and an amount of a specific component (represented by glucose in this embodiment) of the sampled blood is measured.

The upper surface of the lid body 22 has a display window (opening) 221 passing through the lid body 22. The display window 221 is covered with a plate member made from a transparent material.

The display unit 12 is disposed in the containing space 23 at a position corresponding to that of the display window 221. Accordingly, various kinds of information displayed on the display unit 12 can be checked via the display window 221.

The display unit 12 is composed of, for example, a liquid crystal display device. (LCD) or the like. Various kinds of information associated with ON/OFF of the power source., power voltage (remaining capacity of the battery), measured value, measurement date & hour, error indication, positional correction indication, operation guidance, and the like can be displayed on the display unit 12.

The audio outputting unit 32 is typically composed of a buzzer (device for generating a specific sound, melody, or the like) or a speaking device.

The notifying means is not limited to those described above but may be exemplified by a light emitting device such as a light emitting diode (LED) or an EL device, a lamp, or an EL display device.

The externally outputting unit 34 is adapted to output data such as the resultant blood sugar level to an external unit such as a personal computer.

An operating button 222 is provided on the upper surface of the lid body 22. In the body fluid component measuring apparatus 1, when the operating button 222 is depressed, the switch 29 is turned on along with the operation of the operating button 222, and a signal is inputted from the switch 29 to the control means 11.

The circuit board 10 is disposed under the display unit 12 in FIG. 1. The control means 11 in the form of a microcomputer and the memory 33 are mounted on the circuit board 10. The control means 11 controls various operations of the body fluid component measuring apparatus 1, for example, an operation to decide whether or not blood has been sampled and an operation to decide whether or not an evacuation state has been established. The control means 11 incorporates a calculating portion for calculating an amount of glucose (blood sugar value) in blood on the basis of a signal from the measuring means 7.

The pump 8 is disposed as the evacuating means (sucking means) under the left half of the circuit board 10 in FIG. 1. The pump 8 is electrically operated, and is connected to a ventilation passage 54 formed in the housing 5 (to be described later) via a tube 81. The tube 81 is flexible, and is made from a polymer material selected, for example, from polyolefines such as polyvinyl chloride, polyethylene, polypropylene, and ethylene-vinyl acetate copolymer (EVA), and other polymers such as polyamide, polyester, silicon rubber, and polyurethane.

The pump 8 is operated to suck and discharge air in a bore portion 52 of the housing 5 and thereby evacuate the bore portion 52 of the housing 5. In particular, the body fluid component measuring apparatus 1 is tried to evacuate the core portion 52 of the housing 5 by the pump 8 before or after puncture by the needle body 141 of the chip 13 (to be described later) or at the same time of the puncture.

The pump 8 may be any pump insofar as it can evacuate both the bore portion 52 of the housing 5 and the puncture site of the finger tip to a degree of vacuum allowing suction of blood from the puncture site of the finger (for example, about 100 to 400 mmHg).

The battery 9 is disposed as the power source under the right half of the circuit board 10 in FIG. 1. The battery 9 is electrically connected to the pump 8, the electromagnetic valve 26, the solenoid 28, the control means 11, the display unit 12, the audio outputting unit 32, and the like for supplying a necessary power to each of these constituted elements.

The measuring means 7 is disposed in front of the pump 8 in FIG. 1. The measuring means 7 is adapted to optically detect the supply (sampling) of blood to a strip of test paper 18 provided for the chip 13 (to be described later), and to optically measure an amount of glucose in the blood diffused in the test paper 18. The measuring means 7 is located in the vicinity of a side portion., at which the test paper 18 is positioned, of the chip 13 in a state that the chip 13 is mounted to and held by the housing 5.

In this way, the measuring means 7 has both the function of detecting the sampling of blood and the function of measuring an amount of glucose (specific component) in blood diffused in the test paper 18. As a result, in comparison with an apparatus in which two means having the above-described two functions are separately provided, the apparatus 1 including the measuring means 7 is advantageous in reducing the number of parts, simplifying the configuration of the apparatus 1, and reducing the number of steps of assembling the constituent elements into the apparatus 1.

The measuring means 7 has a light emitting device (light emitting diode) 11 and a light receiving device (photodiode) 72.

The light emitting device 71 is electrically connected to the control means 11, and the light receiving device 72 is electrically connected to the control means 11 via an amplifier 24 and an A/D converter 25.

The light emitting device 71 is operated for emission of light on the basis of a signal from the control means 11. The light emitted from the light emitting device 71 is preferably pulse light emitted intermittently at specific time intervals.

When the light emitting device 71 is turned on in a state that the chip 13 is mounted to the housing 5, the test paper 18 is irradiated with the light emitted from the light emitting device 71. The light is reflected from the test paper 18 and is received by the light receiving device 72. In the light receiving device 72, the light is subjected to photoelectric conversion. An analogue signal corresponding to the quantity of light is outputted from the light receiving device 72, and is suitably amplified by the amplifier 24. The amplified analogue signal is converted into a digital signal by the A/D converter 25, to be inputted in the control means 11.

The control means 11 decides, on the basis of the inputted signal, whether or not blood has been sampled, that is, whether or not blood has been diffused in the test paper 18 of the chip 13.

The control means 11 performs a specific calculating operation on the basis of the inputted signal, and further, a correcting calculation if needed, to determine an amount of glucose (blood sugar level) in the blood. The blood sugar level thus obtained is displayed on the display unit 12.

The housing 5 in which the puncturing means 4 is housed and the chip withdrawing mechanism 6 connected to the base end side of the housing 5 are disposed in front of the measuring means 7 in FIG. 1.

The chip withdrawing mechanism 6 is fixed to the housing body 21 Meanwhile, the housing 5 is not fixed to the housing body 21 but is disposed so as to be movable in the axial direction (from right or left to left or right in FIG. 1) by the chip withdrawing mechanism 6.

As described above, at time of use of the body fluid component measuring apparatus 1, the chip 13 is mounted to the housing 5. The chip 13 may be the same as that of the apparatus according to the first aspect, and therefore, the detailed description thereof is omitted.

Such a chip 13 is removably fitted in the housing 5 (fitting portion 53) via the opening 212 of the housing body 21 as described above.

As shown in FIGS. 15 and 16, the housing 5 is formed of a cylindrical member with its bottom closed with a wall portion 51, and internally has a bore portion (housing space) 52. The housing 5 internally has, on the tip side, a small-diameter fitting portion 53. To be more specific, the inner diameter of the fitting portion 53 is set to correspond to the diameter of the outer periphery of the chip 13. The chip 13 is inserted and fixedly fitted in the fitting portion 53. It is to be noted that in FIGS. 15 and 16, the chip 13 is depicted with its structure simplified for easy understanding of description.

A side portion of the housing 5 has the ventilation passage 54 for communicating the bore portion 52 to the outside. The ventilation passage 54 is connected to the pump 8 via the tube 81. Air in the bore portion 52 is sucked via the ventilation passage 54 and the tube 81 by the pump 8, to evacuate the bore portion 52 (including the interior of the chip 13).

As shown in FIG. 5, one end of a tube 82 is branched from a middle point of the tube 81, and the other end of the tube 82 is opened to the outside of the main body 21. The tube 82 is flexible, and may be made, for example, from the same material as that for forming the tube 81.

The electromagnetic valve 26 is provided in a middle point of the tube 82 for opening/closing the flow passage of the tube 82.

When the electromagnetic valve 26 remains closed (OFF state), the evacuation state of the bore portion 52 (including the interior of the chip 13) is kept. On the other hand, when the electromagnetic valve 26 is opened (ON state), air (atmospheric air) is introduced from the outside into the bore portion 52 having been kept in the evacuation state via the tubes 82 and 81 and the ventilation passage 54, to release or relieve the evacuation state of the bore portion 52.

Accordingly, an evacuation releasing means is composed of the tubes (flow passage) 81 and 82 and the electromagnetic valve 26.

As shown in FIGS. 15 and 16, an approximately central portion of the wall portion 51 of the housing 5 has a hole 511. A fine tube 65 internally having an orifice (passage) 651 is provided in the hole 511. Air flows between the bore portion 52 and a volume variable chamber 631 (to be described later), which are disposed on both sides of the fine tube 65, via the orifice 651.

A ring-shaped seal ring (sealing member) 55 is fitted in the tip surface of the housing 5. With this provision of the seal ring 55, when the chip 13 is mounted to the housing 5, the base end of the flange 164 of the chip 13 is brought into contact with the seal ring 55, to keep the air-tightness of the bore portion 52.

The seal ring 55 is made from an elastic material selected, for example, from various kinds of rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluorocarbon rubber, and various kinds of thermoplastic elastomers such as a styrene based elastomer, a polyolefine based elastomer, a polyvinyl chloride based elastomer, a polyurethane based elastomer, a polyester based elastomer, a polyamide based elastomer, a polybutadine based elastomer, and a fluorocarbon rubber based elastomer.

A ring-shaped flange 56 is formed on the outer periphery of a base end portion of the housing 5 in such a manner as to project outwardly therefrom. A cylindrical projection 59 is formed at the base end of the housing 5.

The puncturing means 4 is housed in a portion, on the base end side from the fitting portion 53, of the bore portion 52 of the housing 5. The puncturing means 4 is adapted to move the puncture needle 14 mounted thereto in the direction toward the tip side for puncturing the surface of the finger tip with the cutting edge of the needle body 141.

The puncturing means 4 is composed of the plunger 41, a coil spring (urging member) 42 for urging the plunger 41 in the direction toward the tip side, and a coil spring (urging member) 43 for urging the plunger 41 in the direction toward the base end.

A cup-shaped needle holder 411 is provided at a tip portion of the plunger 41. The small-diameter 143 of the puncture needle 14 is removably fitted in the needle holder 411. An elastically deformable elastic piece 412 is provided on a base end portion of the plunger 41. The elastic piece 412 has, at its tip, a locking portion 413 having the shape of a projecting arm.

In a state before the chip 13 is mounted to the housing 5, that is, in a state before the puncture needle 14 is mounted to the plunger 41 (see FIG. 15), the locking portion 413 is urged upwardly in FIG. 15 by the elastic force of the elastic piece 412, to be brought into contact with the inner peripheral surface of the housing 5. On the other hand, in a state that the chip 13 is mounted to the housing 5, that is, in a state that the puncture needle 14 is mounted to the plunger 41 (see FIG. 16), the locking portion 413 is inserted in an opening 57 formed so as to pass through the housing 5, to be locked with an edge portion of the opening 57. In this case, the movement of the plunger 41 in the direction toward the tip side is restricted. In addition, the opening 57 is closed with a flat seal sheet (sealing member) 58 to keep the air-tightness of the bore portion 52. The seal sheet 58 may be made from the same material as that for forming the above-described seal ring 55.

The coil spring (spring for puncture) 42 is disposed on the base end side of the plunger 41 in a state that both ends thereof are in contact with the plunger 41 and the wall portion 51. On the other hand, the coil spring (spring for return) 43 is disposed on the tip side of the plunger 41 in a state that both ends thereof are in contact with the plunger 41 and the fitting portion 53.

As shown in FIG. 19, the pressure sensor 27 is disposed in the housing 5 for detecting the pressure in the bore portion 52 (including the interior of the chip 13) of the housing 5. Information from the pressure sensor 27, more specifically, the pressure (data) detected by the pressure sensor 27 is inputted in the control means 11.

As shown in FIGS. 15 and 16, the solenoid 28 as the drive source for electrically driving the locking portion 413 is provided outside the housing 5. The solenoid 28 is disposed in such a manner as to inwardly move the locking portion 413 in the bore portion 52 (in the direction shown by an arrow in the figure) by a plunger 281 of the solenoid 28.

In the state that the locking portion 413 is locked with the opening 57, the coil spring 42 remains as compressed, to urge the plunger 41 in the direction toward the tip side. When the plunger 281 of the solenoid 28 is moved in the direction shown by the arrow in the figure to release the locking state of the locking portion 413 from the opening 57, the coil spring 42 is extended to move the plunger 41 in the direction toward the tip side, to allow the edge of the needle body 141 to puncture the surface (skin) of the finger tip. In this way, an operation starting means for starting the operation of the puncturing means 4 is composed of the solenoid 28.

At the time, the coil spring 43 is compressed to urge the plunger 41 in the direction toward the base end side, that is, to return the plunger 41 in the direction toward the base end side. Thereafter, the movement of the plunger 41 is attenuated, and the plunger 41 is rested at a position where the elastic force of the coil spring 42 is balanced against the elastic force of the coil spring 43.

In the state that the plunger 41 is rested, the cutting edge of the needle body 141 is in a state being housed in the chip 13.

The chip withdrawing mechanism 6 is provided on the base end side of the housing 5. The chip withdrawing mechanism 6 is the same as that of the apparatus according to the first aspect, and the overlapped description thereof is omitted.

Figure 17:
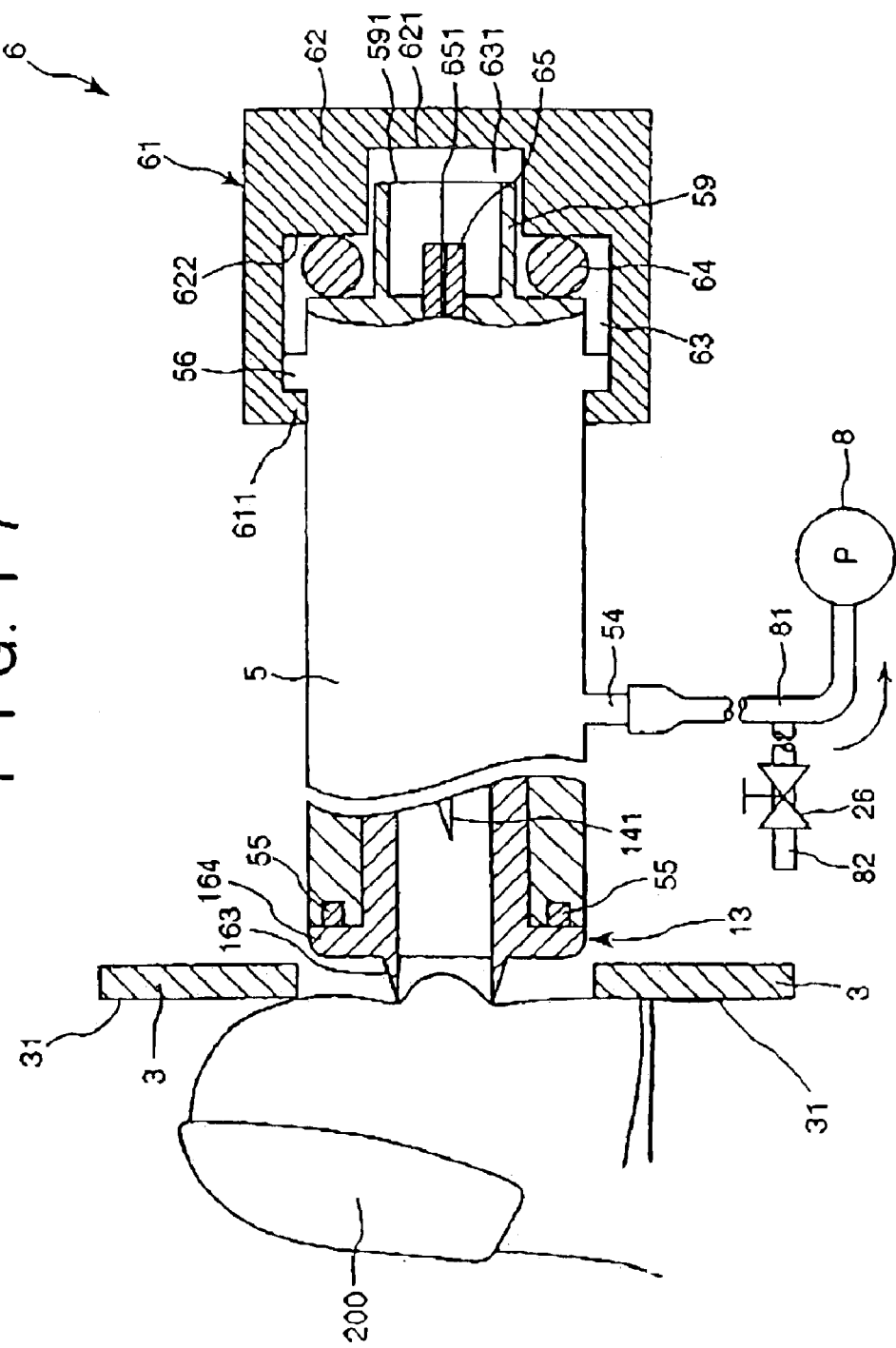
FIG. 17 is a vertical sectional view showing a configuration of essential portions of the body fluid component measuring apparatus according to the first embodiment of the second aspect of the present invention (in a state at the time of operation of an evacuating means)
Figure 18:
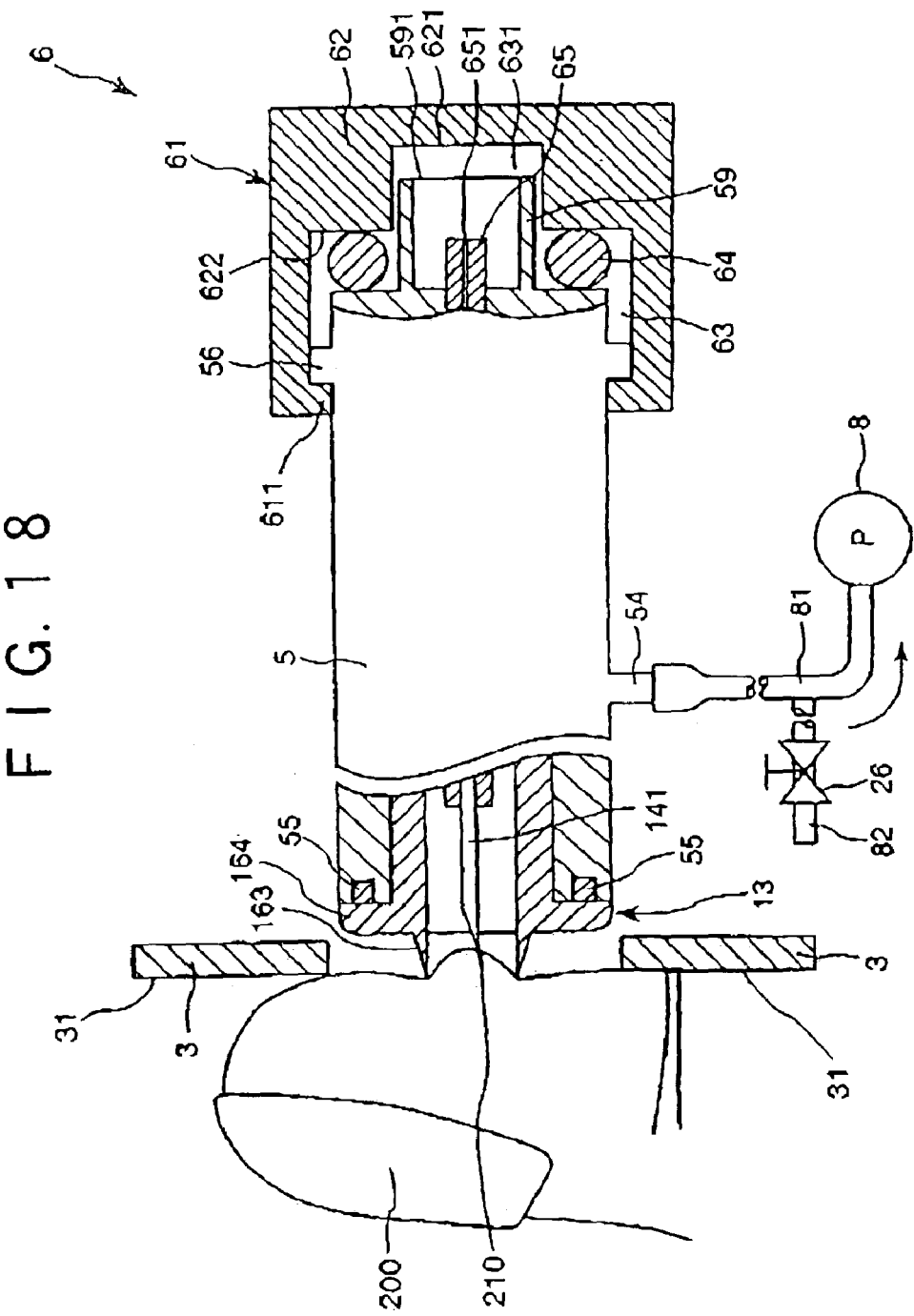
FIG. 18 is a vertical sectional view showing the configuration example of the essential portions of the body fluid component measuring apparatus according to the first embodiment of the second aspect of the present invention (in a state at the time of operation of a puncturing means)

According to the body fluid component measuring apparatus 1, as shown in FIG. 17, when the finger tip 200 is touched to the finger touch portion 3, the surface of the finger tip 200 comes into contact with the tip of the contact portion 163, with a result that blood capillaries of a portion around the puncture site 210 are compressed by the contact portion 163; however, since the chip 13 can be separated from the finger tip 200 while the puncture site 210 of the finger tip 200 is kept in the evacuation state as shown in FIG. 8, the blood capillaries of the portion around the puncture site 210, which have been compressed by the tip of the contact portion 163, are released. As a result, the blood, which is denoted by reference numeral 220 in FIG. 8, can be more certainly sucked from the puncture site 210 for a short time, and thereby an amount of blood necessary for measurement of an amount of glucose can be sufficiently sampled.

In the operational state of the chip withdrawing mechanism 6 (the state shown in FIG. 8), the housing 5 is moved in the direction toward the base end, to compress the seal ring 64. Since the seal ring 64 is formed of an elastic body as described above, in the state shown in FIG. 8, the seal ring 64 urges the housing 5 in the direction toward the tip side. Accordingly, by the opening the electromagnetic valve 26 to release the evacuation state, the seal ring 64 is returned nearly to the original shape by the self-elastic force to move the housing 5 in the direction toward the tip side (see FIGS. 9 and 10). In this case, after the tip of the flange 56 of the housing 5 comes into contact with the base end of the projection 611 of the main body portion 61, the tip of the flange 56 is no longer moved in the direction toward the tip side (see FIG. 10). In this way, the housing 5 and the chip 13 mounted thereto are returned to the positions in the state before the operation of the chip withdrawing mechanism 6.

Actions of respective constituent elements and control operations of the control means in the case of puncturing the finger tip, sampling blood therefrom, diffusing the blood in the test paper, and measuring a blood sugar level by using the body fluid component measuring apparatus will be described below with reference to the configurations of the constituent elements shown in FIGS. 2 and 5, FIGS. 7 to 10, and FIGS. 15 to 17, and further, a flow chart shown in FIG. 20.

[1] The chip 13 is inserted in the fitting portion 53 of the housing 5 via the opening 212 of the housing body 21, and the small-diameter portion 143 of the puncture needle 14 is fitted in the needle holder 411 (see FIG. 16).

The chip 13 is further pressed in the direction toward the base end side, to push the plunger 41 against the urging force of the coil spring 42 in the direction toward the base end side. Along with the movement of the plunger 41, the locking portion 413, which is in contact with the inner peripheral surface of the bore portion 52 while being urged by the elastic force of the elastic piece 412, is moved in the direction toward the base end side. When reaching the position of the opening 57, the locking portion 413 is inserted in the opening 57 (see FIG. 16) In this state, even if the pressing force of the chip 13, which force is applied to the plunger 41 in the direction toward the base end side, is released, the movement of the plunger 41 in the direction toward the tip side is restricted by locking of the locking portion 413 with the opening 57. At this time, the coil spring 42 is in the compression state. The preparation of puncturing the finger tip with the puncturing means 4 and the preparation of sampling blood (specimen) are thus accomplished.

[2] The power switch (not shown) is turned on, to activate the constituent elements of the body fluid component measuring apparatus 1, thereby bringing them into measurable states. In this state, the electromagnetic valve 26 remains closed.

[3] The finger tip (finger) 200 is touched to the touch portion 3, so that the finger tip 200 is brought into press-contact with the contact portion 163 of the chip 13. At this time, the tip opening 162 may be blocked with the finger tip 200 in such a manner as to make the leakage of air as small as possible (see FIG. 5).

[4] The operating button 222 is depressed, to operate the body fluid component measuring apparatus 1, thereby executing a program shown in FIG. 20.

Prior to puncture, the control means 11 starts the suction of air in the bore portion 52 (including the interior of the chip 13) of the housing 5 (step S101 in FIG. 20).

As a result, unless there is some problem, the pressure in the bore portion 52 (including the interior of the chip 13) is reduced, to be brought into an evacuation state (see FIG. 17). At this time, the puncture site 210, punctured by the needle body 141, of the finger tip 200 is also brought into the evacuation state. In this state, however, a portion, positioned inside the contact portion 163 (tip opening 162), of the finger tip 200 is inwardly swelled in a round shape in the chip 13, with a result that blood capillaries at a portion around the puncture site 210 being in contact with the tip of the contact portion 163 are compressed.

The pressure in the bore portion 52 (including the interior of the chip 13) of the housing 5 is detected by the pressure sensor 27 (step S102 in FIG. 20).

The control means 11 decides, on the basis of information supplied from the pressure sensor 27, whether or not the bore portion 52 (including the interior of the chip 13) has been evacuated, and specifically, whether or not the pressure in the bore portion 52 has been reduced to a predetermined pressure (step S103 in FIG. 20).

If it is decided in step S103 that the pressure has been not sufficiently reduced, it is decided whether or not a predetermined time has elapsed (step S104 in FIG. 20).

If it is decided in step S104 that the predetermined time has not elapsed, a notice about positional correction is given to the operator (step S105 in FIG. 20).

In step S105, the notice that the position of the finger touched to the finger touch portion 3 should be corrected is given in the form of written words displayed on the display unit 12 or in the form of audio words outputted from the audio outputting unit 32. It is to be noted that the notice may be of course given via both the display unit 12 and the audio outputting unit 32.

Such a notice about positional correction allows the operator (user) to comprehend the circumstance, and on the basis of such information, the operator may move the finger to a suitable position and take an appropriate attitude of the finger so as to make the leakage of air as small as possible.

After step S105 is executed, the process is returned to step S102, and steps S102, S103 and S104 are executed again. At this time, if it is decided in step S104 that the predetermined time has elapsed, a notice about error is given to the operator (step S106 in FIG. 20), and at the same time, the pump 8 is stopped and the electromagnetic valve 26 is once opened and closed again.

In step S106, the notice that an error has occurred during operation is given in the form of written words displayed on the display unit 12 or in the form of audio words outputted from the audio outputting unit 32. It is to be noted that the notice may be of course given via both the display unit 12 and the audio outputting unit 32.

Such a notice about an error allows the operator (user) to comprehend that an error (trouble) has occurred during operation.

[5] If it is decided in step S103 that the pressure has been sufficiently reduced, the surface of the finger tip 200 is punctured (step S107 in FIG. 20).

To be more specific, when it is decided that the pressure has been sufficiently reduced, the control means 11 outputs a signal for applying a current to a coil of the solenoid 28. The plunger 281 of the solenoid 28 thus energized is moved in the direction shown by the arrow in FIG. 16, to be brought into contact with the locking portion 413, whereby the locking portion 413 is pushed down in the bore portion 52 by the plunger 281. As a result, the locking of the locking portion 413 is released, so that the plunger 41 is moved in the direction toward the tip side by the elastic force of the compressed coil spring 42. Along with the movement of the plunger 41, the needle body 141 projects from the tip opening 162, to puncture the surface of the finger tip 200 (see FIG. 18). Blood flows out of the puncture site 210 punctured by the needle body 141.

After the finger tip 200 is punctured by the needle body 141, the plunger 41 is pushed back in the direction toward the base end side by the elastic force of the coil spring 43. The movement of the plunger 41 is attenuated, and finally the plunger 41 is rested at the position where the elastic force of the coil spring 43 is balanced against the elastic force of the coil spring 42 (see FIG. 8). At this time, the cutting edge of the needle body 141 is in the state being housed in the chip 13. In this way, the cutting edge of the needle body 141 does not project from the tip opening 162 except that it is used for puncture of the finger tip, to thereby eliminate erroneous damages of the skin of the finger tip and preventing infection via the needle body 141. The body fluid component measuring apparatus 1 is thus advantageous in carrying out the sampling of blood with a high safety.

[6] Along with continuation of the suction of air from the bore portion 52 by the pump 8, air in the volume variable chamber 631 gradually flows in the bore portion 52 via the orifice 651, whereby the volume of the volume variable chamber 631 is gradually reduced. As a result, the housing 5 and the chip 13 mounted thereto are gradually moved in the direction toward the base end, that is, in the direction apart from the finger tip 200.

At this time, since the bore portion 52 and the puncture site 210 of the finger tip 200 are each kept in the evacuation state, the finger tip 200 is prevented from being separated from the tip opening 162. Also, even if the chip 13 is moved in the direction apart from the finger tip 200, the finger tip 200 being in contact with the touch portion 3 does not follow the movement of the chip 13. The chip 13 is thus certainly separated from the finger tip 200.

As the chip 13 is separated from the finger tip 200, the blood capillaries at the portion around the puncture site 210 compressed by the tip of the contact portion 163 are gradually released, with a result that blood 220 is sucked from the puncture site 210 (see FIG. 9) In this way, as compared with a configuration that the chip 13 is not separated from the finger tip 200, the flow of the blood is promoted. This is advantageous in sampling a necessary amount of blood for a short time.

It is preferable to set the minimum pressure caused by the pump 8 in a range of about 100 to 400 mmHg.

The base end 591 of the projection 59 is eventually brought into contact with the bottom surface of the recess 621, to stop the movement of the housing 5 and the chip 13 mounted thereto in the direction toward the base end side. Since the chip 13 is stopped after being separated from the finger tip 200 by an appropriate distance, the finger tip 200 is prevented from being separated from the tip opening 162. This certainly prevents occurrence of an inconvenience that the blood 220 sucked from the puncture site 210 be scattered to contaminate the surroundings. In this way, the body fluid component measuring apparatus 1 is advantageous in sampling blood with a high safety.

As described above, according to the body fluid component measuring apparatus 1, the puncturing operation and the evacuating operation are nearly simultaneously performed by only one depressing operation of the operating button 222, the withdrawing action of the chip 13 is performed by making use of the evacuated pressure caused by the pump 8, and the evacuation releasing action (to be described later) is automatically started. The body fluid component measuring apparatus 1, therefore, is very excellent in its operability.

[7] The blood 220 raised in a granular shape from the puncture site 210 as a result of the operation described in the item [6] is sucked in the chip 13, to be brought into contact with the blood introducing guide 166 formed in the chip 13. The blood 220 is then introduced to the test paper 18 via the blood passage 19, being supplied to the center portion of the test paper 18, and is diffused radially in the test paper 18 (see FIG. 2).

Along with the supply and diffusion of the blood 220 on and in the test paper 18, glucose (component to be measured) in the blood 220 reacts with the reagent supported by the test paper 18, with a result that the test paper 18 is colored to a degree depending on the amount of glucose.

On the other hand, after executing step S107 shown in FIG. 20, the control means 11 drives the measuring means 7, to monitor the coloring of the test paper 18 via the measuring means 7, thereby deciding whether or not the blood has been sampled (step S108 in FIG. 20).

In step S108, if the voltage level of a signal inputted from the light receiving device 72 of the measuring means 7 is more than a predetermined threshold value, it is decided that the blood has been sampled, and if the voltage level of the above signal is equal to or less than the threshold value, it is decided that the blood has been not sampled.

The threshold value is set to a value sufficiently larger than a voltage level of the signal before coloring of the test paper 18 and sufficiently smaller than a voltage level of the signal at the time of coloring of the test paper 18.

If it is decided in step S108 that the blood has been not sampled, it is decided whether or not the predetermined time has elapsed (step S109 in FIG. 20).

If it is decided in step S104 that the predetermined time has not elapsed, the process is returned to step S108, and steps S108 and S109 are executed again. At this time, if it is decided in step S109 that the predetermined time has elapsed, a notice about an error is given to the operator (step S110 in FIG. 20), and at the same time, the pump 8 is stopped and the electromagnetic valve 26 is opened once to release the evacuation state and is closed again.

In step S106, the notice that an error has occurred during operation is given in the form of written words displayed on the display unit 12 or in the form of audio words outputted from the audio outputting unit 32. It is to be noted that the notice may be of course given via both the display unit 12 and the audio outputting unit 32.

Such a notice about an error allows the operator (user) to comprehend that an error (trouble) has occurred during operation.

If it is decided in step S108 that the blood has been sampled, the pump 8 is stopped, and more specifically, the suction of air in the bore portion 52 by the pump 8 is stopped (step S111 in FIG. 20).

The electromagnetic valve 26 is opened to release the evacuation state (step S112 in FIG. 20).

When the electromagnetic valve 26 is opened, outside air (atmospheric air) flows in the bore portion 52 (including the interior of the chip 13) and the puncture site 210 via the tubes 82, 81 and the ventilation passage 54, whereby the pressure in the bore portion 52 (including the interior of the chip 13) and the puncture site 210 is returned to atmospheric air (see FIG. 10).

The seal ring 64 is also nearly returned to the original shape by the self-elastic force, to move the housing 5 in the direction toward the tip side (see FIGS. 10 and 11). After a while, the tip of the flange 56 of the housing 5 is brought into contact with the base end of the projection 611 of the main body portion 61, to restrict the movement of the housing 5 in the direction toward the tip side (see FIG. 11).

When the operator becomes insensible of suction at the portion, around the puncture site 210, of the finger tip 200 and thereby recognizes that the internal pressure is returned to atmospheric pressure, he or she separates the finger tip 200 from the contact portion 163 of the chip 13.

[8] After executing step S112 shown in FIG. 20, the control means 11 causes the measuring means 7 to measure the degree of coloring of the test paper 18, executes arithmetic operation based on the data thus obtained, and performs correcting calculation such as temperature correcting calculation or hematocrit value correcting calculation, to quantify the blood sugar level (step S113 in FIG. 20).

In this case, since the evacuation state of the bore portion 52 (including the interior of the chip 13), that is, the evacuation state of the housing space of the test paper 18 is released, a component (for example, oxygen, carbon dioxide, or water vapor) in atmospheric air necessary for reaction between glucose (component to be measured) in the blood 220 and the reagent supported by the test paper 18 can be sufficiently supplied to the test paper 18, whereby the blood sugar level can be accurately measured.

The blood sugar level thus calculated is displayed on the display unit 12 (step S114 in FIG. 20).

The operator can thus confirm his or her blood sugar level from the value displayed on the display unit 12.

In addition, after the evacuation state is released in step S112, the electromagnetic valve 26 is closed again for the next measurement.

As described above, according to the body fluid component measuring apparatus 1, it is possible to certainly sample a sufficient amount of blood necessary for measurement for a short time and to accurately, certainly measure the blood sugar level (amount of a specific component in blood).

Since the puncture site is evacuated before puncture and the puncture is performed by the puncturing means 4 only when it is confirmed that the puncture site is in the evacuation state, it is possible to prevent the finger from being uselessly punctured, and hence to reduce the burden of the operator (patient).

Since the test paper 18 is provided on the chip 13, it is possible to continuously perform the puncture of the finger tip, sampling of blood, diffusion of blood in the test paper 18, and measurement (quantitative determination) of blood, and hence to easily measure the blood sugar level (component) in blood for a short time.

Since the preparation for operating the body fluid component measuring apparatus 1 is facilitated, the apparatus 1 is advantageous for periodical or repeated use thereof.

According to the body fluid component measuring apparatus 1, it is possible to prevent occurrence of an accident such as erroneous puncture of the skin of the operator again after puncture necessary for sampling of blood, and hence to sample blood with a high safety. The apparatus 1 is also advantageous in that the operator can use the apparatus 1 with less sensation of fear against puncture because the puncture needle 14 is out of the eyeshot of the operator.

Accordingly, the body fluid component measuring apparatus 1 is suitable for the operator (patient) to measure his or her blood sugar level.

The body fluid component measuring apparatus 1 is advantageous in terms of simple configuration, small size and light weight, low cost, and suitability for mass-production.

A second embodiment of a body fluid component measuring apparatus according to the second aspect of the present invention will be described below.

Figure 21:
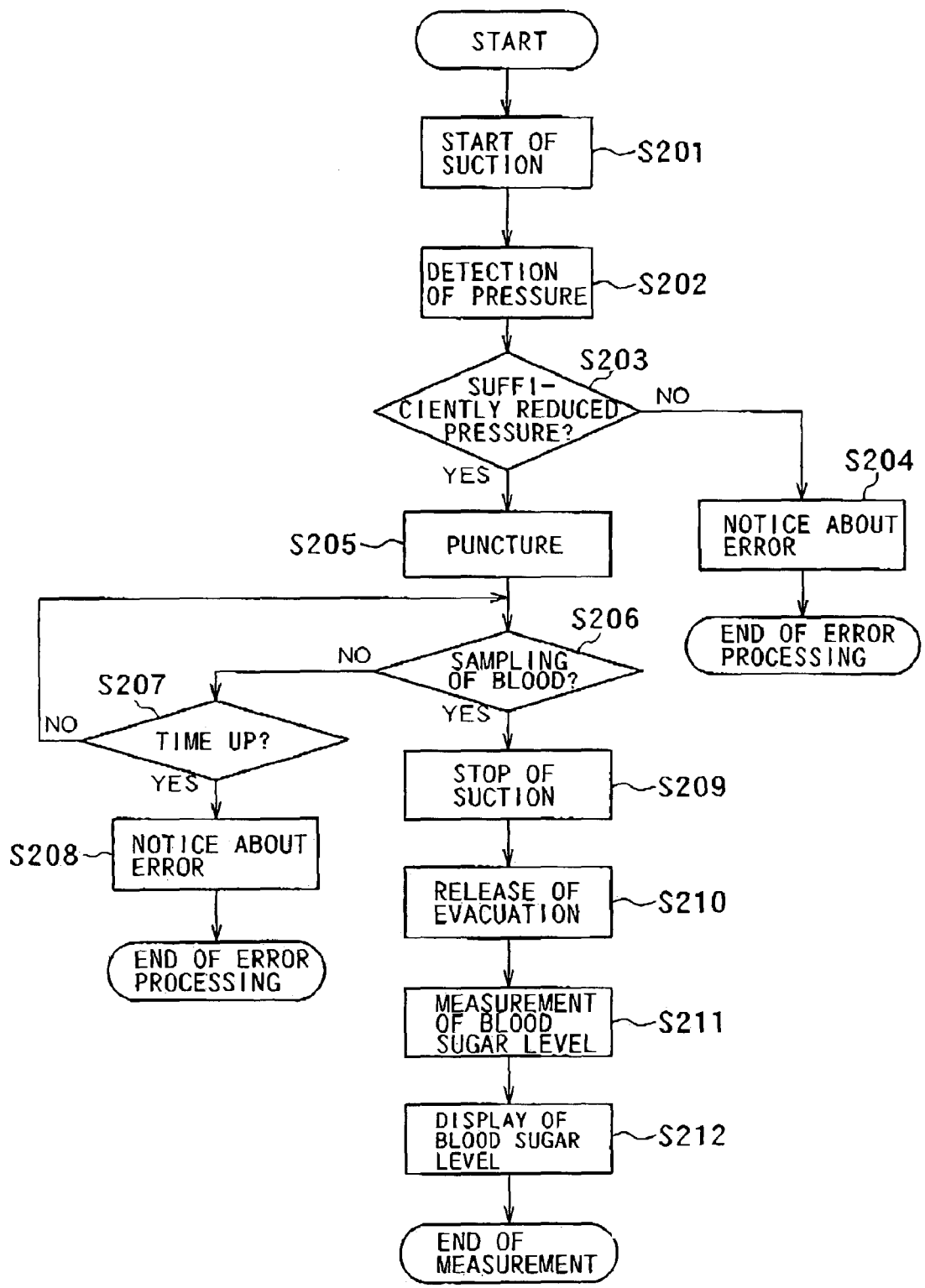
FIG. 21 is a flow chart showing a control operation of a control means for a body fluid component measuring apparatus according to a second embodiment of the second aspect of the present invention.

FIG. 21 is a flow chart showing a control operation of a control means for the body fluid component measuring apparatus according to the second embodiment of the present invention. The following description will be made about main different points from the above-described body fluid component measuring apparatus according to the first embodiment, with the description of the common points thereto omitted.

The configuration of the body fluid component measuring apparatus 1 according to the second embodiment is the same as that of the body fluid component measuring apparatus 1 according to the first embodiment, and therefore, the description thereof is omitted, and the operations of the body fluid component measuring apparatus 1 according to the second embodiment will be described with reference to a flow chart shown in FIG. 21, principally, about different points from the body fluid component measuring apparatus 1 according to the first embodiment.

In the body fluid component measuring apparatus 1, when the operating button 222 is depressed, a program shown in FIG. 21 is executed.

Prior to puncture, the control means 11 starts the suction of air in the bore portion 52 (including the interior of the chip 13) of the housing 5 (step S201 in FIG. 21).

The pressure in the bore portion 52 (including the interior of the chip 13) of the housing 5 is detected by the pressure sensor 27 (step S202 in FIG. 21).

The control means 11 decides, on the basis of information supplied from the pressure sensor 27, whether or not the bore portion 52 (including the interior of the chip 13) has been evacuated, and specifically, whether or not the pressure in the bore portion 52 has been reduced to a predetermined pressure (step S203 in FIG. 21).

If it is decided in step S203 that the pressure has been not sufficiently reduced, a notice about error is given to the operator (step S204 in FIG. 21), and at the same time, the pump 8 is stopped and the electromagnetic valve 26 is once opened and closed again.

In step S204, the notice that an error has occurred during operation is given in the form of written words displayed on the display unit 12 or in the form of audio words outputted from the audio outputting unit 32. It is to be noted that the notice may be of course given via both the display unit 12 and the audio outputting unit 32.

Such a notice about an error allows the operator (user) to comprehend that an error (trouble) has occurred during operation.

If it is decided in step S103 that the pressure has been sufficiently reduced, the surface of the finger tip is punctured (step S205 in FIG. 21).

The control means 11 drives the measuring means 7, to monitor the coloring of the test paper 18 via the measuring means 7, thereby deciding whether or not the blood has been sampled (step S206 in FIG. 21).

If it is decided in step S206 that the blood has been not sampled, it is decided whether or not the predetermined time has elapsed (step S207 in FIG. 21).

If it is decided in step S207 that the predetermined time has not elapsed, the process is returned to step S206, and steps S206 and S207 are executed again. At this time, if it is decided in step S207 that the predetermined time has elapsed, a notice about an error is given to the operator (step S208 in FIG. 21), and at the same time, the pump 8 is stopped and the electromagnetic valve 26 is opened once to release the evacuation state and is closed again.

In step S208, the notice that an error has occurred during operation is given in the form of written words displayed on the display unit 12 or in the form of audio words outputted from the audio outputting unit 32. It is to be noted that the notice may be of course given via both the display unit 12 and the audio outputting unit 32.

Such a notice about an error allows the operator (user) to comprehend that an error (trouble) has occurred during operation.

If it is decided in step S206 that the blood has been sampled, the pump 8 is stopped, and more specifically, the suction of air in the bore portion 52 by the pump 8 is stopped (step S209 in FIG. 21).

The electromagnetic valve 26 is opened to release the evacuation state (step S210 in FIG. 21).

The control means 11 causes the measuring means 7 to measure the degree of coloring of the test paper 18, executes arithmetic operation based on the data thus obtained, and performs correcting calculation such as temperature correcting calculation or hematocrit value correcting calculation, to quantify the blood sugar level (step S211 in FIG. 21).

The blood sugar level thus calculated is displayed on the display unit 12 (step S212 in FIG. 21).

The operator can thus confirm his or her blood sugar level from the value displayed on the display unit 12.

In addition, after the evacuation state is released in step S210, the electromagnetic valve 26 is closed again for the next measurement.

According to the body fluid component measuring apparatus 1, it is possible to obtain the same effect as that obtained by the above-described the body fluid component measuring apparatus 1 according to the first embodiment.

A third embodiment of a body fluid component measuring apparatus according to the second aspect of the present invention will be described below.

Figure 22:
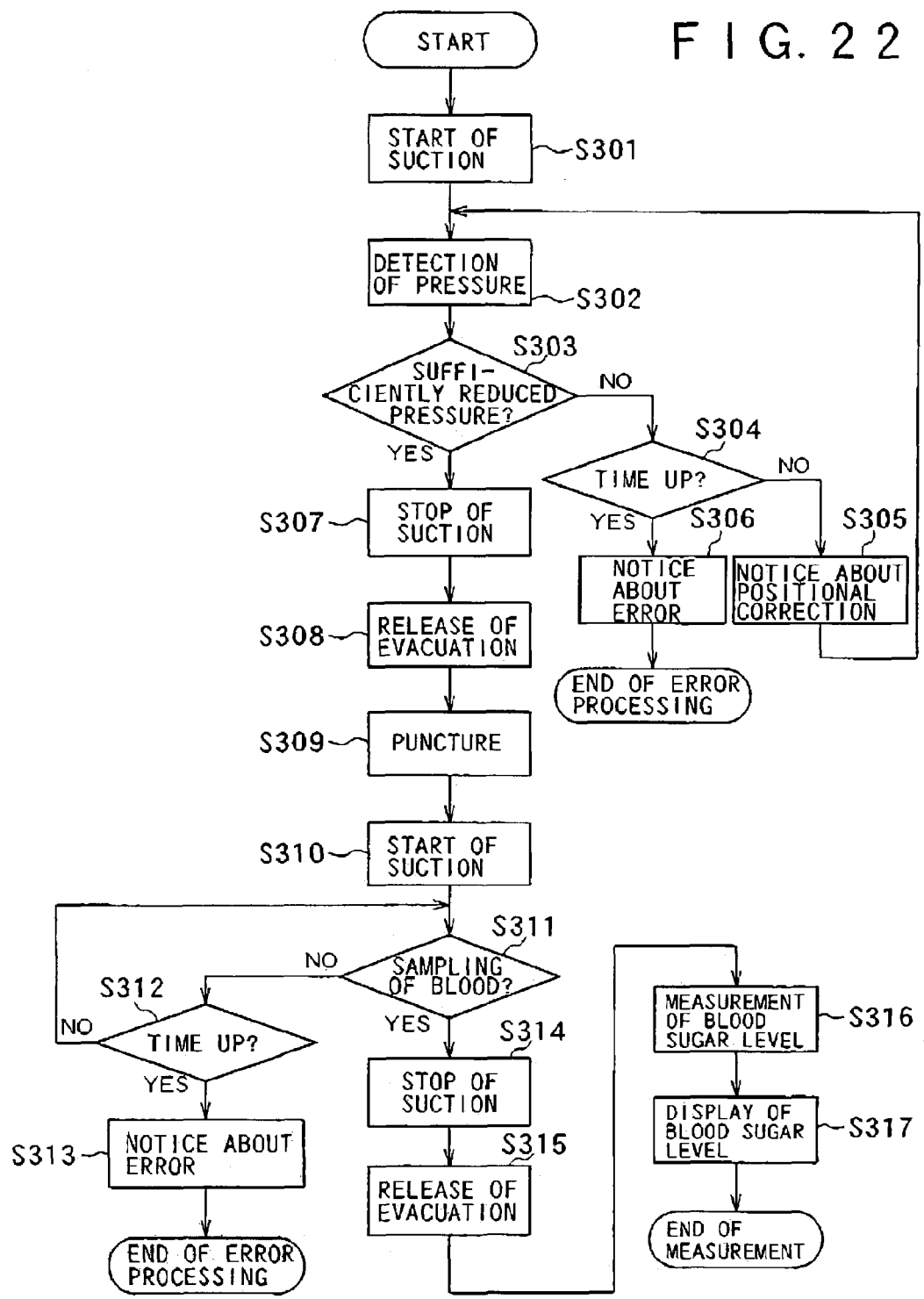
FIG. 22 is a flow chart showing a control operation of a control means for a body fluid component measuring apparatus according to a third embodiment of the second aspect of the present invention.

FIG. 22 is a flow chart showing a control operation of a control means for the body fluid component measuring apparatus according to the third embodiment of the present invention. The following description will be made about main different points from the above-described body fluid component measuring apparatus according to the first embodiment, with the description of the common points thereto omitted.

The configuration of the body fluid component measuring apparatus 1 according to the third embodiment is the same as that of the body fluid component measuring apparatus 1 according to the first embodiment, and therefore, the description thereof is omitted, and the operations of the body fluid component measuring apparatus 1 according to the second embodiment will be described with reference to a flow chart shown in FIG. 22, principally, about different points from the body fluid component measuring apparatus 1 according to the first embodiment.

In the body fluid component measuring apparatus 1, when the operating button 222 is depressed, a program shown in FIG. 22 is executed.

Prior to puncture, the control means 11 starts the suction of air in the bore portion 52 (including the interior of the chip 13) of the housing 5 (step S301 in FIG. 22).

The pressure in the bore portion 52 (including the interior of the chip 13) of the housing 5 is detected by the pressure sensor 27 (step S302 in FIG. 22).

The control means 11 decides, on the basis of information supplied from the pressure sensor 27, whether or not the bore portion 52 (including the interior of the chip 13) has been evacuated, and specifically, whether or not the pressure in the bore portion 52 has been reduced to a predetermined pressure (step S303 in FIG. 22).

If it is decided in step S203 that the pressure has been not sufficiently reduced, it is decided whether or not a predetermined time has elapsed (step S304 in FIG. 22).

If it is decided in step S304 that the predetermined time has not elapsed, a notice about positional correction is given to the operator (step S305 in FIG. 22).

In step S305, the notice that the position of the finger touched to the finger touch portion 3 should be corrected is given in the form of written words displayed on the display unit 12 or in the form of audio words outputted from the audio outputting unit 32. It is to be noted that the notice may be of course given via both the display unit 12 and the audio outputting unit 32.

Such a notice about positional correction allows the operator (user) to comprehend the circumstance, and on the basis of such information, the operator may move the finger to a suitable position and take an appropriate attitude of the finger so as to make the leakage of air as small as possible.

After step S305 is executed, the process is returned to step S302, and steps S302, S303 and S304 are executed again. At this time, if it is decided in step S304 that the predetermined time has elapsed, a notice about error is given to the operator (step S306 in FIG. 22), and at the same time, the pump 8 is stopped and the electromagnetic valve 26 is once opened and closed again.

In step S306, the notice that an error has occurred during operation is given in the form of written words displayed on the display unit 12 or In the form of audio words outputted from the audio outputting unit 32. It is to be noted that the notice may be of course given via both the display unit 12 and the audio outputting unit 32.

Such a notice about an error allows the operator (user) to comprehend that an error (trouble) has occurred during operation.

It is decided in step S303 that the pressure has been sufficiently reduced, the pump 8 is stopped, and specifically, the suction of air in the bore portion 52 by the pump 8 is stopped (step S307 in FIG. 22).

The electromagnetic valve 26 is once opened, to release the evacuation state (step S308 in FIG. 22). It is to be noted that after the evacuation state is released in step S308, the electromagnetic valve 26 is closed again.

The surface of the finger tip 200 is then punctured (step S309 in FIG. 22).

The pump 8 is operated, to start the suction of air in the bore portion 52 (including the interior of the chip 13) of the housing 5 (step S310 in FIG. 22).

The control means 11 drives the measuring means 7, to monitor the coloring of the test paper 18 via the measuring means 7, thereby deciding whether or not the blood has been sampled (step S311 in FIG. 22).

If it is decided in step S311 that the blood has not sampled, it is decided whether or not the predetermined time has elapsed (step S312 in FIG. 22).

If it is decided in step S312 that the predetermined time has not elapsed, the process is returned to step S311, and steps S311 and S312 are executed again. At this time, if it is decided in step S312 that the predetermined time has elapsed, a notice about an error is given to the operator (step S313 in FIG. 22), and at the same time, the pump 8 is stopped and the electromagnetic valve 26 is opened once to release the evacuation state and is closed again.

In step S313, the notice that an error has occurred during operation is given in the form of written words displayed on the display unit 12 or in the form of audio words outputted from the audio outputting unit 32. It is to be noted that the notice may be of course given via both the display unit 12 and the audio outputting unit 32.

Such a notice about an error allows the operator (user) to comprehend that an error (trouble) has occurred during operation.

If it is decided in step S311 that the blood has been sampled, the pump 8 is stopped, and more specifically, the suction of air in the bore portion 52 by the pump 8 is stopped (step S314 in FIG. 22).

The electromagnetic value 26 is opened to release the evacuation state (step S315 in FIG. 22).

The control means 11 causes the measuring means 7 to measure the degree of coloring of the test paper 18, executes arithmetic operation based on the data thus obtained, and performs correcting calculation such as temperature correcting calculation or hematocrit value correcting calculation, to quantify the blood sugar level (step S316 in FIG. 22).

The blood sugar level thus calculated is displayed on the display unit 12 (step S317 in FIG. 22).

The operator can thus confirm his or her blood sugar level from the value displayed on the display unit 12.

In addition, after the evacuation state is released in step S315, the electromagnetic valve 26 is closed again for the next measurement.

According to the body fluid component measuring apparatus 1, it is possible to obtain the same effect as that obtained by the above-described the body fluid component measuring apparatus 1 according to the first embodiment.

According to this body fluid component measuring apparatus 1, when the evacuated state is detected, the evacuation state is once released and then the puncture is performed. Accordingly, although a difference in swelled amount of the skin of the finger tip by the pressure occurs among individuals because of a difference in rigidity of the skin of the finger tip among individuals, it is possible to make such a difference in swelled amount of the skin of the finger tip as small as possible, and hence to puncture the finger tip with the puncture depth kept highly constant irrespective of a difference among individuals.

It is to be noted that according to the present invention, steps S304 and S305 may be omitted.

A fourth embodiment according to the second aspect of the present invention will be described with reference to FIG. 13.

A body fluid component measuring apparatus 1 according to the fourth embodiment is the same as the above-described body fluid component measuring apparatus 1 according to each of the first, second and third embodiments except for the configuration of the evacuation releasing means, and therefore, the overlapped description thereof is omitted.

In this body fluid component measuring apparatus 1, as shown in FIG. 13, a fine tube 83 is provided in place of the electromagnetic valve 26 of the body fluid component measuring apparatus 1 according to each of the first, second, and third embodiments.

The fine tube 83 is formed of a cylindrical member and internally has an orifice (flow passage) 831. The fine tube 83 is connected to an end portion of the tube 82, and the tip of the fine tube 83 (orifice 831) is opened to the outside of the main body 2.

The orifice 831 of the fine tube 83 is required to be narrow enough to keep a large passing resistance of air. The diameter of the orifice 831 is not particularly limited but is preferably in a range of about 0.01 to 0.3 mm. The length of the orifice 831 is not particularly limited but is preferably in a range of about 5 to 15 mm. By setting the diameter of the orifice 831 within the above range, it is possible to certainly keep the necessary passing (flow) resistance of air.

An evacuation releasing means is composed of the tubes (flow passage) 81, 82 and the fine tube 83.

It is to be noted that the fine tube 83 is not limited to that shown in the figure, and although only one fine tube 83 is provided in this embodiment, a plurality of fine tubes (orifices) may be provided if needed.

In operation of the body fluid component measuring apparatus 1 according to this embodiment, since the flow rate of air sucked by the pump 8 is larger than the flow rate of outside air (atmospheric air) flowing from the orifice 831 of the fine tube 83, when the pump 8 is operated in step S2, the suction of air in the bore portion 52 of the housing 5 is started, whereby the pressure in the bore portion 52 (including the interior of the chip 13) is reduced, to thereby bring the bore portion 52 into an evacuation state.

When the pump 8 is stopped in step S6, outside air (atmospheric air) flows in the bore portion 52 (including the interior of the chip 13) and the puncture site 210 via the orifice 831 of the fine tube 83, the tubes 82 and 81, and the ventilation passage 54, to release the evacuation state of the bore portion 52 (including the interior of the chip 13) and the puncture site 210. The pressure in the bore portion 52 (including the interior of the chip 13) and the puncture site 210 is thus returned to atmospheric pressure.

The body fluid component measuring apparatus 1 according to this embodiment can obtain the same effect as that obtained by the above-described body fluid component measuring apparatus 1 according to each of the first, second, and third embodiments.

While the body fluid component measuring apparatus according to the second aspect of the present invention has been described on the basis of the first and second embodiments shown in the figures, the present invention is not limited thereto. For example, the configuration of each of the constituent elements described in the embodiments may be replaced with any configuration exhibiting the same function.

In the above-described embodiments according to the second aspect, the body fluid to be sampled is represented by blood; however, according to the present invention, the body fluid to be sampled is not limited thereto but may be exemplified by sweat, lymph, cerebrospinal fluid, or the like.

The component to be measured is represented by glucose (blood sugar level) in the embodiments; however, according to the present invention, the component to be measured is not limited thereto but may be exemplified by protein, cholesterol, uric acid, creatinine, alcohol, or ions of an inorganic matter such as sodium.

The measuring means in the embodiments is configured to measure an amount of a specific component; however, according to the present invention, the measuring means may be configured to measure a property of a specific component, or to measure both an amount and a property of a specific component.

According to the present invention, a suction force generated by the pump 8, that is, the pressure in the puncture needle housing space (bore portion 52) at the time of sampling blood may be kept constant or changed (with elapsed time).

FIGS. 23 and 24 each show a pressure pattern in the puncture needle housing space (bore portion 52) at the time of sampling blood.

According to the present invention, as shown in FIG. 23, the pressure in the puncture needle housing space (bore portion 52) may be alternately changed between a low pressure and a high pressure; or as shown in FIG. 24, the pressure in the puncture needle housing space. (bore portion 52) may be gradually increased. In this case, the puncture timing is not particularly limited.

An amount, necessary and adequate for measurement, of blood can be more certainly sampled for a shorter time by changing the pressure in the puncture needle housing space (bore potion 52).

The pressure detecting means in the embodiments is represented by the pressure sensor; however, according to the present invention, the pressure detecting means is not limited thereto but may be exemplified by a position sensor.

In the case of using a position sensor as the pressure detecting means, a mark may be attached to the housing 5 and a photo-interrupter representative of the position sensor be provided on the housing body 21 of the main body 2. With this configuration, when the housing 5 is drawn in the chip withdrawing mechanism 6 along with a change in pressure, the position of the housing 5 can be detected by the position sensor.

The means (called "measuring means") used as not only as the blood sampling detecting means for detecting the sampling of blood but also as the measuring means for measuring an amount of a specific component in blood is provided in the embodiments; however, according to the present invention, the blood sampling detecting means and the measuring means may be separately provided.

The blood sampling means is represented by the means for optically detecting the sampling of blood in the embodiments; however, according to the present invention, the blood sampling means is not limited thereto but may be configured as a means for electrically detecting the sampling of blood.

In the case of adopting the blood sampling detecting means for optically detecting the sampling of blood, the detection of the sampling of blood is not necessarily based on the manner described in the embodiments, that is, the manner of detecting the coloring (color development) of the test paper due to reaction between the component in blood and the reagent but may be based on a manner of detecting the introduction of blood in the blood passage (blood flow passage) for supplying blood to the test paper provided on the chip.

In the case of adopting the manner of detecting the introduction of blood in the blood passage, a portion, at least in the vicinity of the blood passage, of the chip may be formed of a member having a light permeability (transparency), and further, the blood sampling detecting means may be configured to emit light to the blood passage via the transparent member, receive the reflected light or transmitted light, and convert the light into an electric signal, and the control means may be configured to monitor a voltage outputted from the blood sampling detecting means. If blood is introduced in the blood passage, the color of a portion, through which the blood passes, of the blood passage is changed into nearly dark-red, to change the quantity of the reflected light or the transmitted light thereat, thereby changing a voltage outputted from the blood sampling detecting means. As a result, the sampling of blood can be detected on the basis of the change in voltage (quantity of light) outputted from the blood sampling detecting means.

The blood sampling detecting means for electrically detecting the sampling of blood is exemplified by a sensor (electrode) for detecting (measuring) an impedance of the blood passage or the like of the chip, or a bio-sensor.

In the case of adopting the bio-sensor, since a current outputted from the bio-sensor is changed if blood is introduced in the blood passage, the sampling of blood can be detected on the basis of the change in current (current value) outputted from the bio-sensor.

In the case of adopting the sensor for detecting an impedance of the blood passage, since an impedance between the electrodes of the sensor, provided across the blood passage, is changed if blood is introduced in the blood passage, the sampling of blood can be detected on the basis of the change in impedance of the blood passage.

The body fluid component measuring apparatus in each of the embodiments is configured by optically measuring the degree of the coloring of the test paper caused by reaction between the component in blood and the reagent, and converting the measured result into a value to be displayed on the display unit; however, the present invention is not limited thereto. For example, the measuring apparatus may be configured by electrically measuring a change in potential caused depending on an amount of a component in blood (specimen), and converting the measured result into a value to be displayed on the display unit.

The measurement method in each of the embodiments is configured so as to release the evacuation state prior to measurement; however, according to the present invention, the method may be configured so as to relieve the evacuation state prior to measurement.

According to the present invention, the actions of the evacuation means, the puncturing means, and the chip withdrawing mechanism may be started either in a manual manner or in an automatic manner, respectively.

A body fluid component measuring apparatus according to a third aspect of the present invention will be hereinafter described in detail on the basis of preferred embodiments shown in the accompanying drawings.

It is to be noted that FIGS. 2 and 9 used for the following description are the same drawings as those used for description of the body fluid component measuring apparatus according to the first aspect of the present invention.

Figure 25:
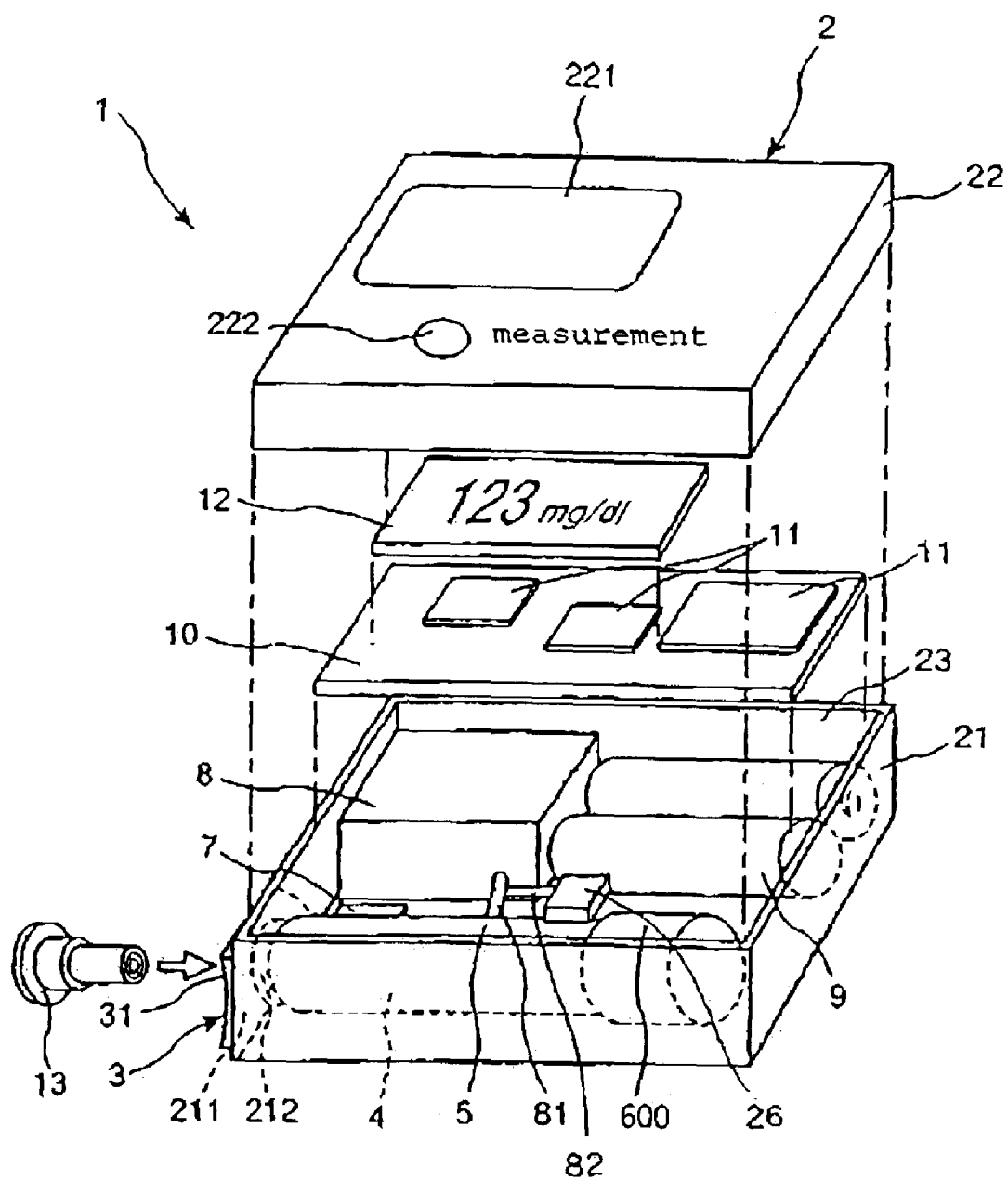
FIG. 25 is a perspective view typically showing a first embodiment of a body fluid component measuring apparatus according a third aspect of the present invention.
Figure 26:
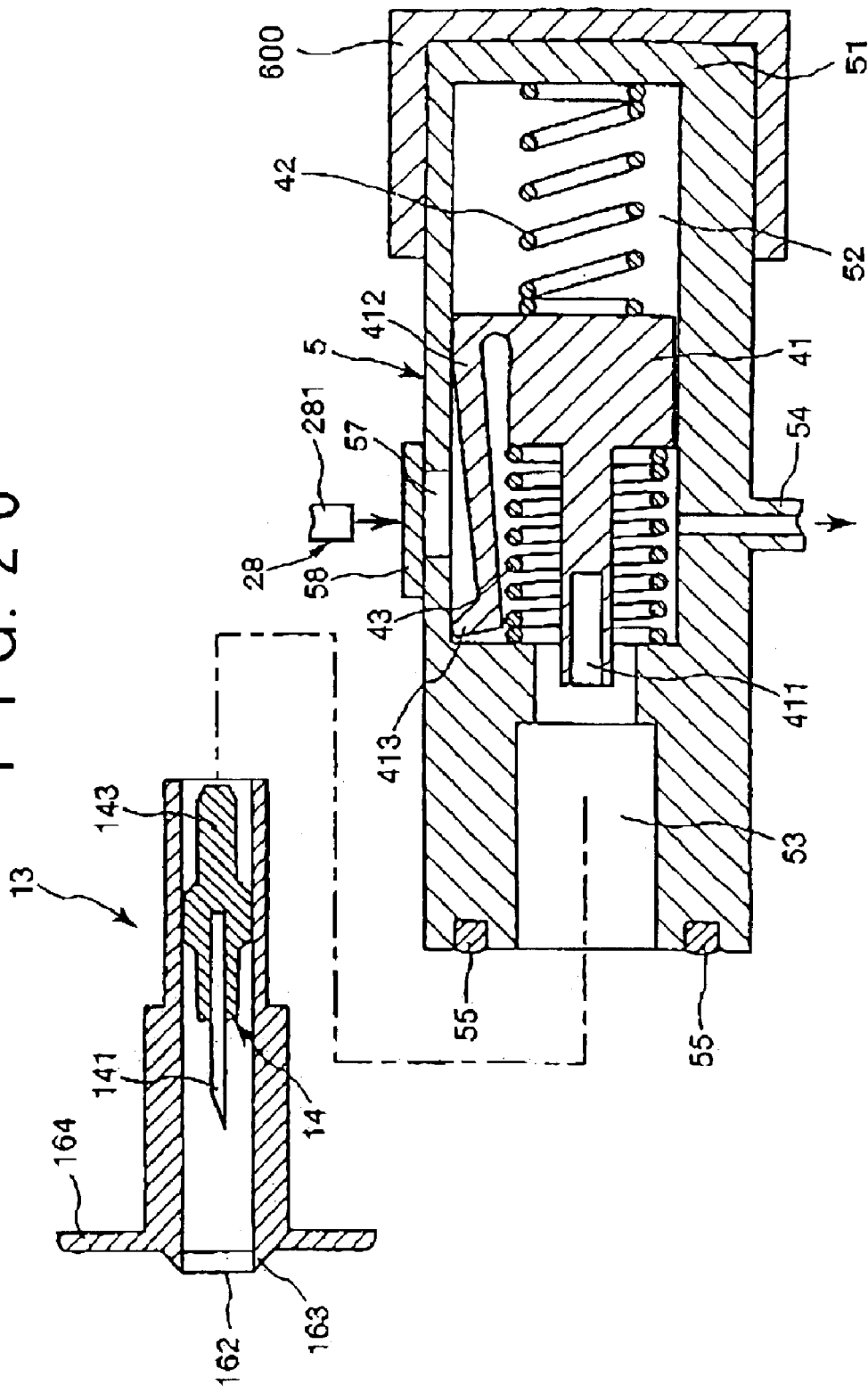
FIG. 26 is a vertical sectional view showing a configuration examples of a puncturing means and a housing for housing the puncturing means in the body fluid component measuring apparatus according to the first embodiment of the third aspect of the present invention (in a state before a chip is mounted to the housing)
Figure 27:
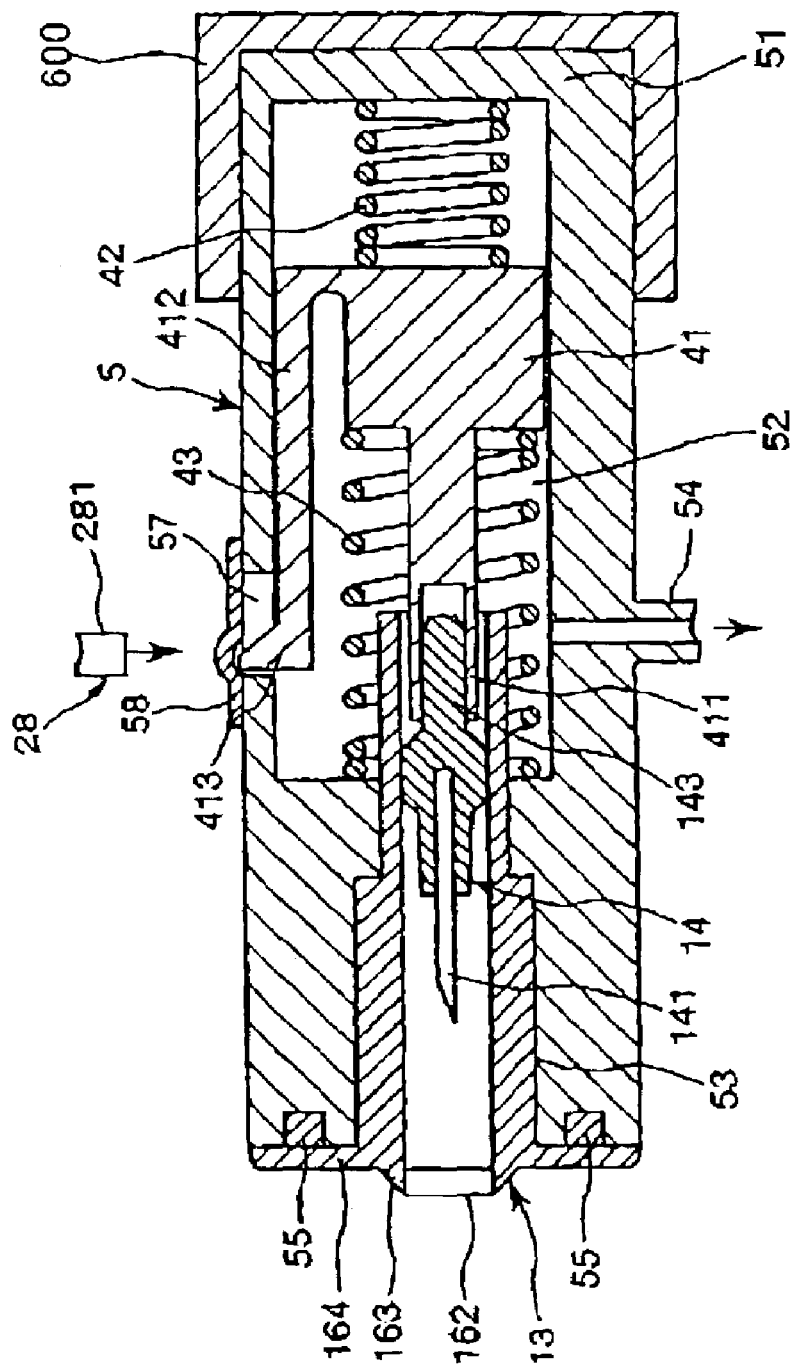
FIG. 27 is a vertical sectional view showing the configuration examples of the puncturing means and the housing for housing the puncturing means in the body fluid component measuring apparatus according to the first embodiment of the third aspect of the present invention (a state after the chip is mounted to the housing)

FIG. 25, equivalent to FIG. 1 used for description of the first aspect, is a perspective view typically showing a first embodiment of the body fluid component measuring apparatus according to the third aspect (hereinafter, the word "third aspect" is omitted); FIGS. 26 and 27 are vertical sectional views showing configuration examples of a puncturing means and a housing for housing the puncturing means, which are equivalent to FIGS. 3 and 4 used for description of the first aspect except that the chip withdrawing mechanism 61 is replaced with a supporting portion 600, respectively; FIGS. 28 to 31 are vertical sectional views showing configuration examples of essential portions of the body fluid component measuring apparatus according to the first embodiment, which are equivalent to FIGS. 5, 6, and 8 and FIG. 10 except that the chip withdrawing mechanism 61 is replaced with the supporting portion 600, respectively.

Figure 32:
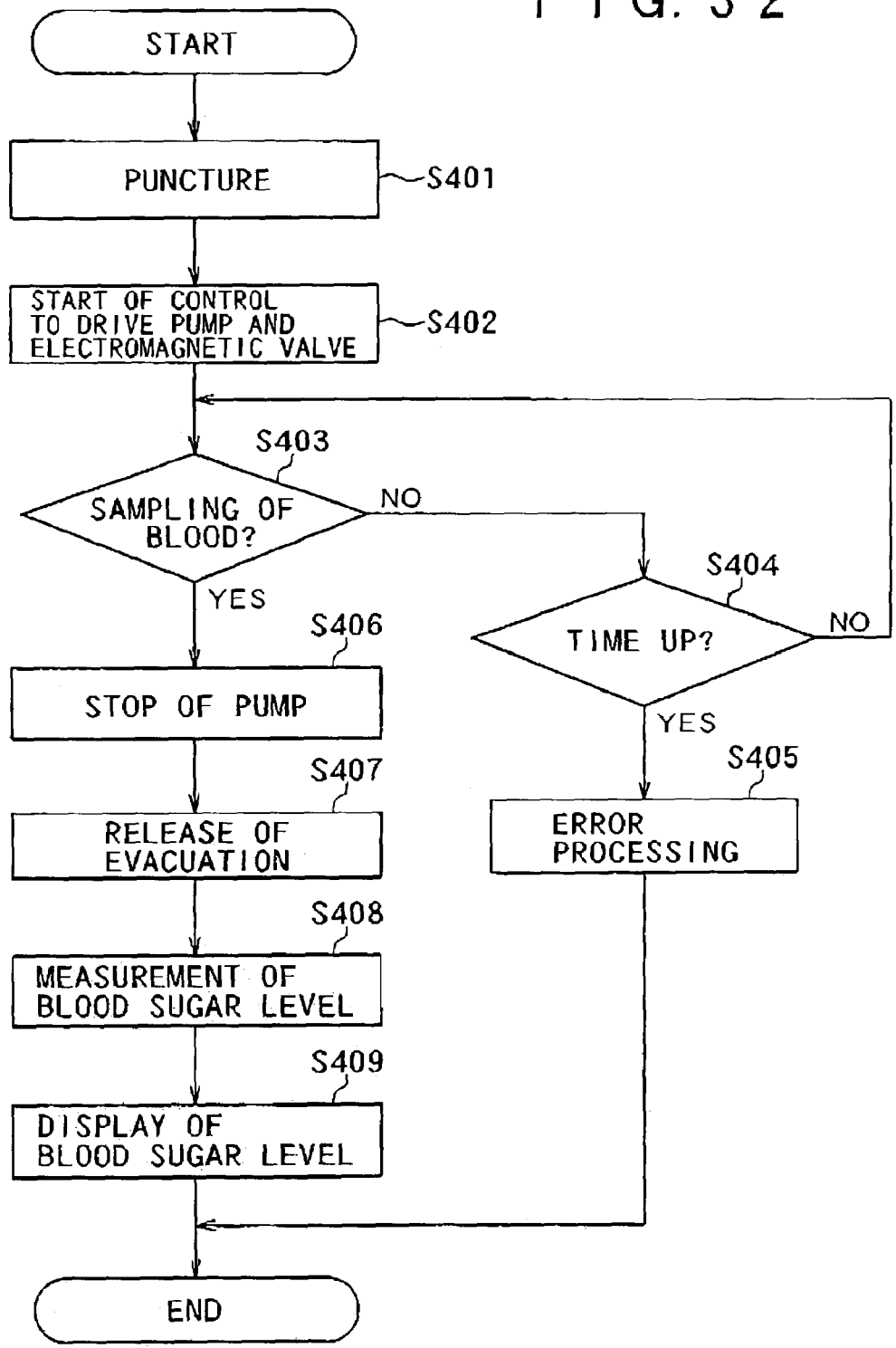
FIG. 32 is a flow chart showing a control operation of a control means for the body fluid component measuring apparatus according to the first embodiment of the third aspect of the present invention.

FIG. 32 is a flow chart showing a control operation of a control means for the body fluid component measuring apparatus according to the first embodiment. In these figures, parts corresponding to those shown in the previous figures are denoted by the same reference numerals.

It is to be noted that these drawings are depicted with the "base end side" of the apparatus taken as the right side and the "tip side" of the apparatus taken as the left side.

Figure 28:
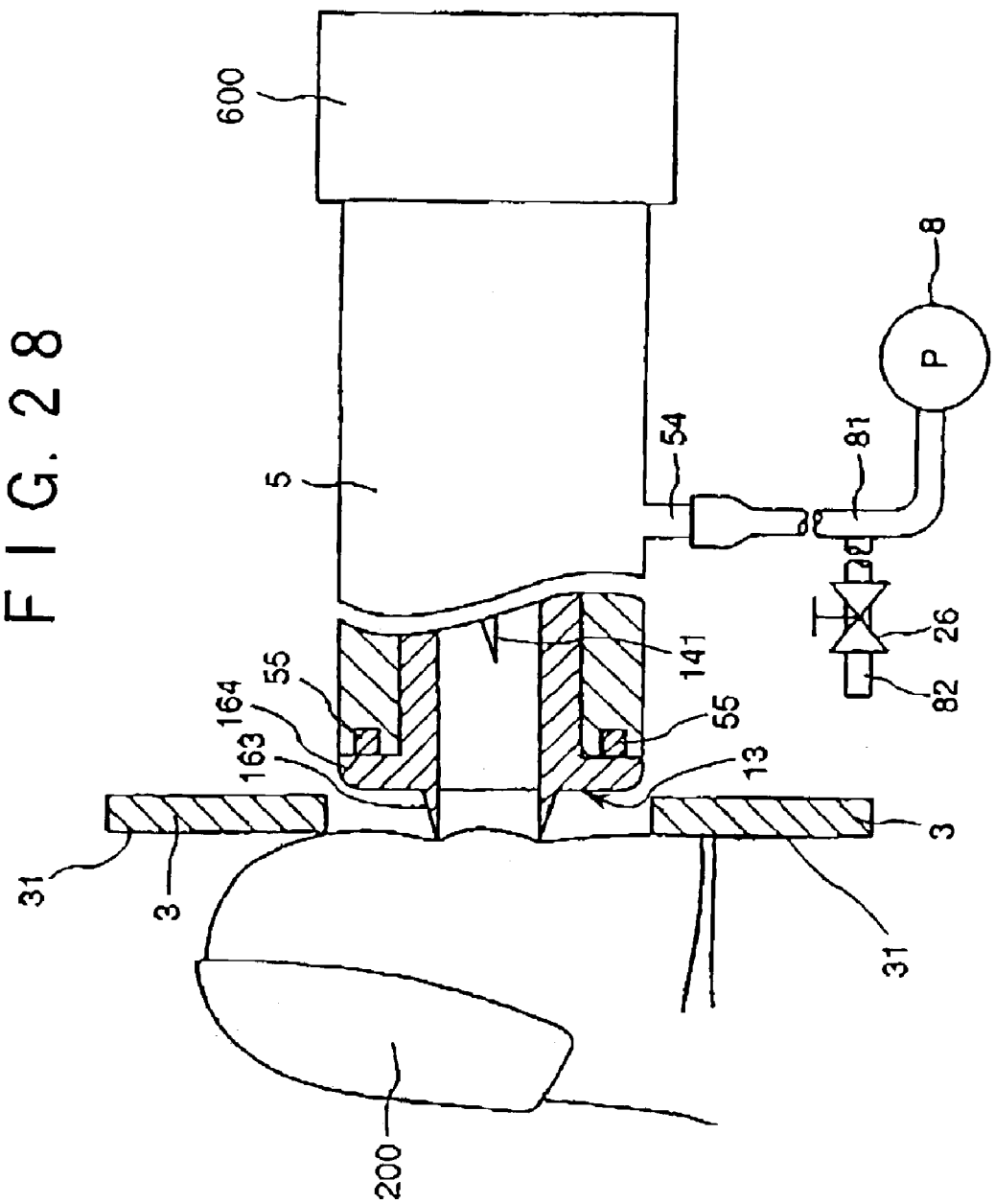
FIG. 28 is a vertical sectional view showing a configuration example of essential portions of the body fluid component measuring apparatus according to the first embodiment of the third aspect of the present invention (in a state before operation of a pressure adjusting means and the puncturing means)
Figure 29:
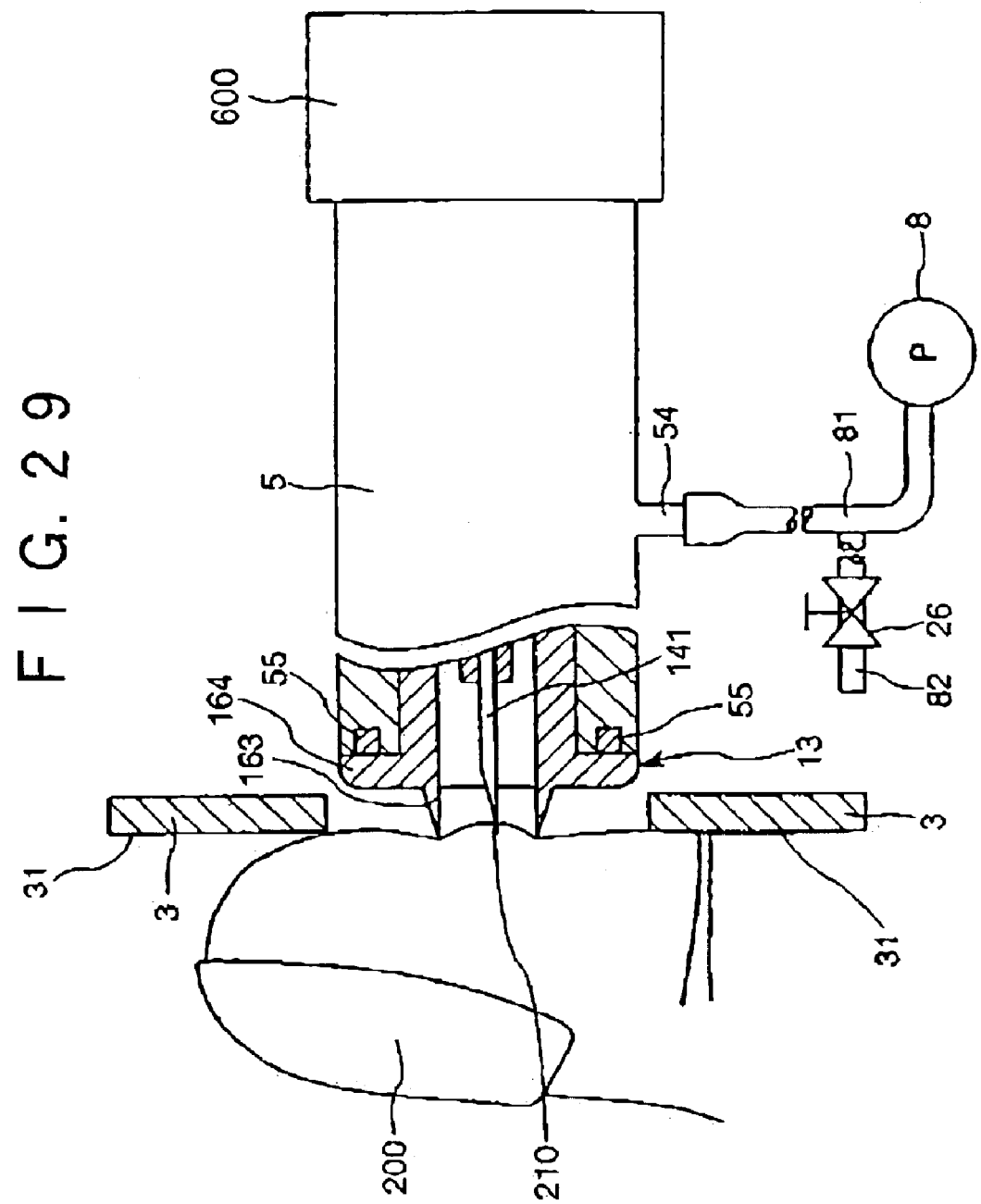
FIG. 29 is a vertical sectional view showing the configuration example of the essential portions of the body fluid component measuring apparatus according to the first embodiment of the third aspect of the present invention (in a state at the time of operation of the puncturing means)

As shown in FIGS. 25, 28 and 9, a body fluid component measuring apparatus (blood component measuring apparatus) 1 according to the first embodiment includes a main body 2, a finger touch portion 3 disposed on the main body 2, a puncturing means 4 housed in a housing 5, a measuring means 7 for detecting the sampling of blood (body fluid) and measuring a specific component in the sampled blood (body fluid), a pump 8 for evacuating the interior of the housing 5, an electromagnetic valve 26 for releasing, relieving, or holding an evacuation state of the interior of the housing 5, a pressure sensor (pressure detecting means) 27 for detecting the pressure in the housing 5, a solenoid (drive source) 28, a switch 29, a battery (power source) 9, a control means 11 and a memory 33 provided on a circuit board 10, a display unit (notifying means) 12, an audio outputting unit (notifying means) 32, and an externally outputting unit 34.

At time of use, the chip 13 is mounted to the body fluid component measuring apparatus 1. Each of constituent elements of the apparatus 1 will be described below.

The main body 2 is composed of a housing body 21 and a lid body 22, which are disposed opposite to each other. The main body 2 internally has a housing space 23, in which the puncturing means 4, the housing 5, the measuring means 7, the pump 8, the electromagnetic valve 26, the solenoid 28, the switch 29, the battery 9, the circuit board 10, the control means 11, the memory 33, the display unit 12, the audio outputting unit 32, and the externally outputting unit 34 are housed. The pressure sensor 27 is disposed in the housing 5.

A wall portion 211 on the tip side of the housing body 21 has an opening 212 passing through the housing body 21. The opening 212 has a circular shape in cross-section. The chip 13 is mounted (held) to the housing 5 (to be described later) via the opening 212.

The finger touch portion 3 (to which the epidermis is to be touched) is provided on a plane on the tip side of the wall portion 211 so as to surround the outer periphery of the opening 212. The finger touch portion 3 has a shape corresponding to that of the finger tip (finger). A finger touch plane 31 is formed on the tip side of the finger touch portion 3. The operator (user) operates the body fluid component measuring apparatus 1 while touching the finger tip to the finger touch portion 3 (finger touch plane 31). With such an operation of the apparatus 1, the finger tip is punctured, blood is sampled therefrom, and an amount of a specific component (represented by glucose in this embodiment) of the sampled blood is measured.

The upper surface of the lid body 22 has a display window (opening) 221 passing through the lid body 22. The display window 221 is covered with a plate member made from a transparent material.

The display unit 12 is disposed in the containing space 23 at a position corresponding to that of the display window 221. Accordingly, various kinds of information displayed on the display unit 12 can be checked via the display window 221.

The display unit 12 is composed of, for example, a liquid crystal display device (LCD) or the like. Various kinds of information associated with ON/OFF of the power source, power voltage (remaining capacity of the battery), measured value, measurement date & hour, error indication, positional correction indication, operation guidance, and the like can be displayed on the display unit 12.

The audio outputting unit 32 is typically composed of a buzzer (device for generating a specific sound, melody, or the like) or a speaking device.

The notifying means is not limited to those described above but may be exemplified by a light emitting device such as a light emitting diode (LED) or an EL device, a lamp, or an EL display device.

The externally outputting unit 34 is adapted to output data such as the resultant blood sugar level to an external unit such as a personal computer.

An operating button 222 is provided on the upper surface of the lid body 22. In the body fluid component measuring apparatus 1, when the operating button 222 is depressed, the switch 29 is turned on along with the operation of the operating button 222, and a signal is inputted from the switch 29 to the control means 11.

The circuit board 10 is disposed under the display unit 12 in FIG. 25. The control means 11 in the form of a microcomputer and the memory 33 are mounted on the circuit board 10. The control means 11 controls various operations of the body fluid component measuring apparatus 1, for example, an operation to decide whether or not blood has been sampled. The control means 11 incorporates a calculating portion for calculating an amount of glucose (blood sugar value) in blood on the basis of a signal from the measuring means 7.

The pump 8 is disposed as the evacuating means (sucking means) under the left half of the circuit board 10 in FIG. 25. The pump 8 is electrically operated, and is connected to a ventilation passage 54 formed in the housing 5 (to be described later) via a tube 81. The tube 81 is flexible, and is made from a polymer material selected, for example, from polyolefines such as polyvinyl chloride, polyethylene, polypropylene, and ethylene-vinyl acetate copolymer (EVA), and other polymers such as polyamide, polyester, silicon rubber, and polyurethane.

The pump 8 is operated to suck and discharge air in a bore portion 52 of the housing 5 and thereby evacuate the bore portion 52 of the housing 5.

The pump 8 may be any pump insofar as it can evacuate both the bore portion 52 of the housing 5 and the puncture site of the finger tip to a degree of vacuum allowing suction of blood from the puncture site of the finger (for example, about 100 to 600 mmHg).

The battery 9 is disposed as the power source under the right half of the circuit board 10 in FIG. 25. The battery 9 is electrically connected to the pump 8, the electromagnetic valve 26, the solenoid 28, the control means 11, the display unit 12, the audio outputting unit 32, and the like for supplying a necessary power to each of these constituted elements.

The measuring means 7 is disposed in front of the pump 8 in FIG. 25. The measuring means 7 is adapted to optically detect the supply (sampling) of blood to a strip of test paper 18 provided for the chip 13 (to be described later), and to optically measure an amount of glucose in the blood diffused in the test paper 18. The measuring means 7 is located in the vicinity of a side portion, at which the test paper 18 is positioned, of the chip 13 in a state that the chip 13 is mounted to and held by the housing 5.

In this way, the measuring means 7 has both the function of detecting the sampling of blood and the function of measuring an amount of glucose (specific component) in blood diffused in the test paper 18. As a result, in comparison with an apparatus in which two means having the above-described two functions are separately provided, the apparatus 1 including the measuring means 7 is advantageous in reducing the number of parts, simplifying the configuration of the apparatus 1, and reducing the number of steps of assembling the constituent elements into the apparatus 1.

The measuring means 7 has a light emitting device (light emitting diode) 71 and a light receiving device (photodiode) 72.

The light emitting device 71 is electrically connected to the control means 11, and the light receiving device 72 is electrically connected to the control means 11 via an amplifier 24 and an A/D converter 25.

The light emitting device 71 is operated for emission of light on the basis of a signal from the control means 11. The light emitted from the light emitting device 71 is preferably pulse light emitted intermittently at specific time intervals.

When the light emitting device 71 is turned on in a state that the chip 13 is mounted to the housing 5, the test paper 18 is irradiated with the light emitted from the light emitting device 71. The light is reflected from the test paper 18 and is received by the light receiving device 72. In the light receiving device 72, the light is subjected to photoelectric conversion. An analogue signal corresponding to the quantity of light is outputted from the light receiving device 72, and is suitably amplified by the amplifier 24. The amplified analogue signal is converted into a digital signal by the A/D converter 25, to be inputted in the control means 11.

The control means 11 decides, on the basis of the inputted signal, whether or not blood has been sampled, that is, whether or not blood has been diffused in the test paper 18 of the chip 13.

The control means 11 performs a specific calculating operation on the basis of the inputted signal, and further, a correcting calculation if needed, to determine an amount of glucose (blood sugar level) in the blood. The blood sugar level thus obtained is displayed on the display unit 12.

The housing 5 in which the puncturing means 4 is housed is disposed in front of the measuring means 7 in FIG. 25.

As described above, at time of use of the body fluid component measuring apparatus 1, the chip 13 is mounted to the housing 5. As is shown in FIG. 2, the chip 13 includes a puncture needle 14, a first housing 15 for slidably housing the puncture needle 14, a second housing 16 disposed on the outer periphery of the first housing 15, a test paper fixing portion 17 disposed on an outer peripheral portion of the second housing 16, and the test paper 18 fixed to the test paper fixing portion 17.

The puncture needle 14 is composed of a needle body 141 and a hub 142 fixed to the base end side of the needle body 141. The puncture needle 15 is housed in a bore portion 152 of the first housing 15.

The needle body 141 is formed of a hollow member or a solid member made from a metal material such as a stainless steel, aluminum, an aluminum alloy, titanium, or a titanium alloy. A sharp edge (needle tip) is formed at the tip of the needle body 141. The surface (skin) of the finger tip is punctured by the cutting edge of the needle body 141.

The hub 142 is formed of an approximately columnar member. The hub 142 is slid with its outer periphery being in contact with an inner peripheral surface 151 of the first housing 15.

A small-diameter portion 143 is formed on the base end side of the hub 142. The small-diameter portion 143 is fitted in a needle holder 411 of a plunger 41 constituting part of the puncturing means 4 (to be described later).

The first housing 15 is formed of a cylindrical member with its bottom closed with a wall portion 153, and internally has a bore portion 152.

An approximately central portion of the wall portion 153 has a hole 154 formed into a circular shape in cross-section. At the time of puncture of the finger tip (finger), the needle body 141 passes through the hole 154. The diameter of the hole 154 is set to be smaller than the outer diameter of the tip of the hub 142. Accordingly, after the puncture needle 14 is moved in the bore portion 152 in the direction toward the tip side until the tip of the hub 142 comes in contact with the base end of the wall portion 153, the puncture needle 14 is no longer moved in the direction toward the tip side. As a result, at the time of puncture of the finger tip, the length of a portion, projecting from the tip of the chip 13, of the needle body 141 can be kept constant. This is advantageous in that the finger tip can be more certainly prevented from being too deeply punctured with the cutting edge of the needle body 141.

The puncture depth of the cutting edge of the needle body 141 in the finger tip may be adjusted by providing a mechanism for adjusting a movement distance of the plunger 41 (to be described later).

The second housing 16 is fixed to the outer periphery of the first housing 15.

The second housing 16 is formed of an approximately cylindrical member, and internally has a bore portion 161.

A ring-shaped contact portion 163 is formed at the tip of the second housing 16 in such a manner as to project outwardly therefrom. The contact portion 163 is a portion to which the finger tip is to be touched, and internally has a top opening (opening) 162 through which the bore portion 161 is opened. The outer peripheral edge of the tip of the contact portion 163 is formed into a shape suitable for stimulating, when the finger tip is touched thereto, the neighborhood of the puncture site to moderate pain caused by puncture, and also suitable for suppressing, when the bore portion 161 is evacuated, the flow of air between the tip of the contact portion 163 and the surface of the finger tip as much as possible. It is to be noted that the contact portion 163 is not necessarily provided at the tip of the second housing 16. For example, the tip surface of the second housing 16 may be flattened in place of provision of the contact portion 163 at the tip of the second housing 16.

In the second housing 16, a ring-shaped flange 164 is formed on an outer peripheral portion near the base end of the contact portion 163 in such a manner as to project outwardly therefrom. When the chip 13 is mounted to the housing 5 (to be described later), the base end of the flange 164 is brought into contact with the tip of the housing 5, to determine the position of the chip 13 to the housing 5.

An outer peripheral portion of the second housing 16 has a recess 165. The test paper fixing portion 17 on which the disk-like test paper 18 has been fixed is mounted in the recess 165.

A blood introducing guide 166 is formed on an inner peripheral surface of the second housing 16 in such a manner as to project inwardly therefrom in the bore portion 161. The blood introducing guide 166 has a function of receiving, after puncture of the finger tip, the blood (specimen) having flown from the tip opening 162 into the bore portion 161.

In such a chip 13, a blood passage 19 communicating the bore portion 161 of the second housing 16 to the outside of the chip 13 via the second housing 16 and the test paper fixing portion 17 is formed. The blood passage 19 is a flow passage for introducing the blood obtained by puncture of the finger tip to the test paper 18. The blood passage 19 has both a passage opening 191 opened to the bore portion 161 and a passage opening 192 opened to the outside of the chip 13. It is to be noted that the passage opening 192 is located at a center portion of the test paper 18.

The blood introducing guide 166 is formed near the passage opening 191. Accordingly, the blood received by the blood introducing guide 166 is efficiently introduced from the passage opening 191 to the blood passage 19. The blood flowing in the blood passage 19 reaches the passage opening 192 due to a capillary phenomenon, and is supplied to the center portion of the test paper 18 disposed to cover the passage opening 192, to be thus radially diffused in the test paper 18.

The test paper 18 is configured by supporting a reagent on a carrier capable of absorbing and diffusing blood therein.

The carrier is formed of a sheet-like porous member such as a non-woven fabric, a woven fabric, or an expanded sheet. The porous member preferably has a hydrophilic property.

The reagent to be supported on the carrier is suitably determined depending on a component, to be measured, in blood (specimen). For example, a combination of glucose oxidase (GOD), peroxidase (POD), and a color coupler (coloring reagent) such as 4-aminoantipyrin or N-ethyl-N-(2-hydroxy-3-sulfopropyl)-m-toluidine may be used as a reagent for measurement of a blood sugar level. A combination of a material reactive with a blood component, for example, ascorbate oxidase, alcohol oxidase, or cholesterol oxidase and the above-described color coupler (coloring reagent) may be also used depending on a component to be measured. The reagent may contain a buffer such as a phosphate buffer. It is to be noted that the kind of reagent and a component to be measured are, of course, not limited to those described above.

Such a chip 13 is removably fitted in the housing 5 (fitting portion 53) via the opening 212 of the housing body 21 as described above.

As shown in FIGS. 25, 26, and 27, a cylindrical supporting portion 600 with its bottom closed is fixed on the base end side of the housing body 21. The base end side of the housing 5 is fitted in the supporting portion 600.

As shown in FIGS. 26 and 27, the housing 5 is formed of a cylindrical member with its bottom closed with a wall portion 51, and internally has a bore portion (housing space) 52. The housing 5 internally has, on the tip side, a small-diameter fitting portion 53. To be more specific, the inner diameter of the fitting portion 53 is set to correspond to the diameter of the outer periphery of the chip 13. The chip 13 is inserted and fixedly fitted in the fitting portion 53. It is to be noted that in FIGS. 26 and 27, the chip 13 is depicted with its structure simplified for easy understanding of description.

A side portion of the housing 5 has the ventilation passage 54 for communicating the bore portion 52 to the outside. The ventilation passage 54 is connected to the pump 8 via the tube 81. Air in the bore portion 52 is sucked via the ventilation passage 54 and the tube 81 by the pump 8, to evacuate the bore portion 52 (including the interior of the chip 13).

As shown in FIG. 28, one end of a tube 82 is branched from a middle point of the tube 81, and the other end of the tube 82 is opened to the outside of the main body 21. The tube 82 is flexible, and may be made, for example, from the same material as that for forming the tube 81.

The electromagnetic valve 26 is provided in a middle point of the tube 82 for opening/closing the flow passage of the tube 82.

When the electromagnetic valve 26 remains closed (OFF state), the evacuation state of the bore portion 52 (including the interior of the chip 13) is kept. On the other hand, when the electromagnetic valve 26 is opened (ON state), air (atmospheric air) is introduced from the outside into the bore portion 52 having been kept in the evacuation state via the tubes 82 and 81 and the ventilation passage 54, to release or relieve the evacuation state of the bore portion 52.

Accordingly, an evacuation releasing means is composed of the tubes (flow passage) 81 and 82 and the electromagnetic valve 26.

A pressure adjusting means for adjusting the pressure in the bore portion 52 (including the interior of the chip 13) is composed of the evacuation releasing means and the pump 8.

A ring-shaped seal ring (sealing member) 55 is fitted in the tip surface of the housing 5. With this provision of the seal ring 55, when the chip 13 is mounted to the housing 5, the base end of the flange 164 of the chip 13 is brought into contact with the seal ring 55, to keep the air-tightness of the bore portion 52.

The seal ring 55 is made from an elastic material selected, for example, from various kinds of rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluorocarbon rubber, and various kinds of thermoplastic elastomers such as a styrene based elastomer, a polyolefine based elastomer, a polyvinyl chloride based elastomer, a polyurethane based elastomer, a polyester based elastomer, a polyamide based elastomer, a polybutadine based elastomer, and a fluorocarbon rubber based elastomer.

The puncturing means 4 is housed in a portion, on the base end side from the fitting portion 53, of the bore portion 52 of the housing 5. The puncturing means 4 is adapted to move the puncture needle 14 mounted thereto in the direction toward the tip side for puncturing the surface of the finger tip with the edge of the needle body 141.

The puncturing means 4 is composed of the plunger 41, a coil spring (urging member) 42 for urging the plunger 41 in the direction toward the tip side, and a coil spring (urging member) 43 for urging the plunger 41 in the direction toward the base end.

A cup-shaped needle holder 411 is provided at a tip portion of the plunger 41. The small-diameter 143 of the puncture needle 14 is removably fitted in the needle holder 411. An elastically deformable elastic piece 412 is provided on a base end portion of the plunger 41. The elastic piece 412 has, at its tip, a locking portion 413 having the shape of a projecting arm.

In a state before the chip 13 is mounted to the housing 5, that is, in a state before the puncture needle 14 is mounted to the plunger 41 (see FIG. 26), the locking portion 413 is urged upwardly in FIG. 26 by the elastic force of the elastic piece 412, to be brought into contact with the inner peripheral surface of the housing 5. On the other hand, in a state that the chip 13 is mounted to the housing 5, that is, in a state that the puncture needle 14 is mounted to the plunger 41 (see FIG. 27), the locking portion 413 is inserted in an opening 57 formed so as to pass through the housing 5, to be locked with an edge portion of the opening 57. In this case, the movement of the plunger 41 in the direction toward the tip side is restricted. In addition, the opening 57 is closed with a flat seal sheet (sealing member) 58 to keep the air-tightness of the bore portion 52. The seal sheet 58 may be made from the same material as that for forming the above-described seal ring 55.

The coil spring (spring for puncture) 42 is disposed on the base end side of the plunger 41 in a state that both ends thereof are in contact with the plunger 41 and the wall portion 51. On the other hand, the coil spring (spring for return) 43 is disposed on the tip side of the plunger 41 in a state that both ends thereof are in contact with the plunger 41 and the fitting portion 53.

The pressure sensor 27 is disposed in the housing 5 for detecting the pressure in the bore portion 52 (including the interior of the chip 13) of the housing 5. Information from the pressure sensor 27, more specifically, the pressure (data) detected by the pressure sensor 27 is inputted in the control means 11.

As shown in FIGS. 26 and 27, the solenoid 28 as the drive source for electrically driving the locking portion 413 is provided outside the housing 5 The solenoid 28 is disposed in such a manner as to inwardly move the locking portion 413 in the bore portion 52 (in the direction shown by an arrow in the figure) by a plunger 281 of the solenoid 28.

In the state that the locking portion 413 is locked with the opening 57, the coil spring 42 remains as compressed, to urge the plunger 41 in the direction toward the tip side. When the plunger 281 of the solenoid 28 is moved in the direction shown by the arrow in the figure to release the locking state of the locking portion 413 from the opening 57, the coil spring 42 is extended to move the plunger 41 in the direction toward the tip side, to allow the edge of the needle body 141 to puncture the surface (skin) of the finger tip. In this way, an operation starting means for starting the operation of the puncturing means 4 is composed of the solenoid 28.

At the time, the coil spring 43 is compressed to urge the plunger 41 in the direction toward the base end side, that is, to return the plunger 41 in the direction toward the base end side. Thereafter, the movement of the plunger 41 is attenuated, and the plunger 41 is rested at a position where the elastic force of the coil spring 42 is balanced against the elastic force of the coil spring 43.

In the state that the plunger 41 is rested, the cutting edge of the needle body 141 is in a state being housed in the chip 13.

In the body fluid component measuring apparatus 1, when the chip 13 is inserted in the fitting portion 53 of the housing 5 and the small-diameter portion 143 of the puncture needle 14 is fitted in the needle holder 411, the tip of the contact portion 163 is nearly aligned to the finger touch plane 31 or slightly projects from the finger touch plane 31 (see FIGS. 27 and 28). As a result, when the finger tip 200 is touched to the finger touch portion 3, the surface of the finger tip 200 is certainly brought into contact with the contact portion 163, to block the tip opening 162.

According to the body fluid component measuring apparatus 1 described above, at the time of sampling blood from the puncture site, the drive of the pump 8 and the electromagnetic valve 26 is controlled, on the basis of information supplied from the pressure sensor 27, in such a manner as to evacuate the bore portion 52 (including the interior of the chip 13) with the pressure fluctuated (changed) with elapsed time.

The pressure pattern in the bore portion 52 at the time of sampling blood is not particularly limited insofar as the bore portion 52 is evacuated with the pressure fluctuated with elapsed time. One example of the pressure pattern in the bore portion will be described below.

Figure 33:
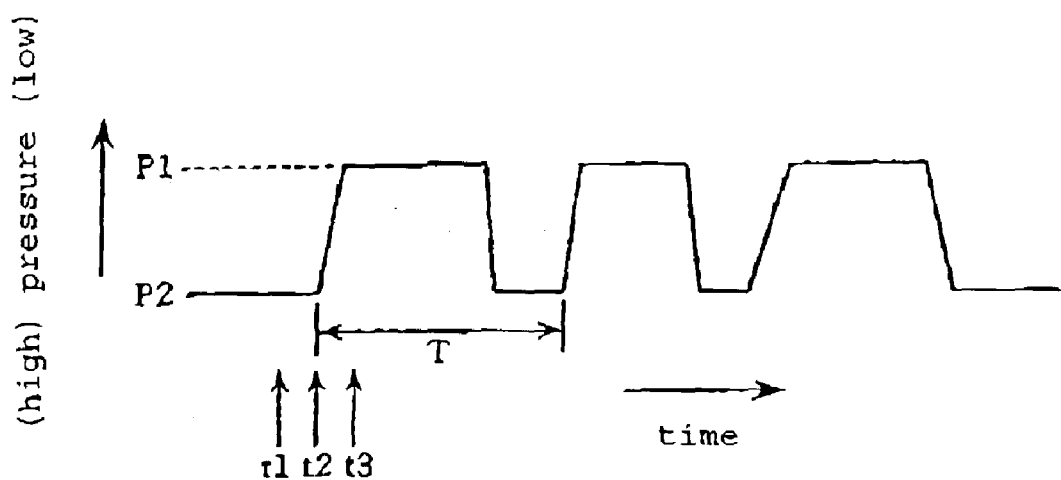
FIG. 33 is a graph showing a pressure pattern in the puncture needle housing space (bore portion 52) at the time of sampling blood in the body fluid component measuring apparatus according to the first embodiment of the third aspect of the present invention.

FIG. 33 is a graph showing one example of the pressure pattern in the bore portion 52 at the time of sampling blood.

As shown in the figure, according to the body fluid component measuring apparatus 1, at the time of sampling blood, the drive of the pump 8 and the electromagnetic valve 26 is controlled in such a manner as to alternately change the pressure in the bore portion 52 between a first pressure P1 lower than atmospheric pressure and a second pressure P2 higher than the first pressure P1.

By setting the pressure pattern in the bore portion 52 as described above, it is possible to certainly sample an amount, necessary and adequate for measurement, of blood for a short time.

The second pressure P2 is preferably set to be nearly equal to or lower than atmospheric pressure.

By setting the second pressure P2 as described above, it is possible to more certainly sample an amount, necessary and adequate for measurement, of blood for a shorter time.

The first pressure P1 is preferably set in a range of about 100 to 600 mmHg, more preferably, in a range of about 400 to 600 mmHg.

By setting the first pressure P1 as described above, it is possible to more certainly sample an amount, necessary and adequate for measurement, of blood for a shorter time.

A difference between the second pressure P2 and the first pressure P1 is preferably set in a range of about 100 to 600 mmHg, more preferably, in a range of about 300 to 600 mmHg.

By setting the pressure difference as described above, it is possible to more certainly sample an amount, necessary and adequate for measurement, of blood for a shorter time.

A period T in the pressure fluctuation pattern is preferably set in a range of about 1 to 30 sec, more preferably, in a range of about 1 to 5 sec.

By setting the period T as described above, it is possible to more certainly sample an amount, necessary and adequate for measurement, of blood for a shorter time.

According to the present invention, the shapes of respective waveforms shown in FIG. 33 may be nearly equal to each other, or be partially or wholly different from each other.

Actions of respective constituent elements and control operations of the control means in the case of puncturing the finger tip, sampling blood therefrom, diffusing the blood in the test paper, and measuring a blood sugar level by using the body fluid component measuring apparatus will be described below with reference to the configurations of the constituent elements shown in FIGS. 2 and 9 and FIGS. 26 to 31, and further a flow chart shown in FIG. 32.

[1] The chip 13 is inserted in the fitting portion 53 of the housing 5 via the opening 212 of the housing body 21, and the small-diameter portion 143 of the puncture needle 14 is fitted in the needle holder 411 (see FIG. 27).

The chip 13 is further pressed in the direction toward the base end side, to push the plunger 41 against the urging force of the coil spring 42 in the direction toward the base end side. Along with the movement of the plunger 41, the locking portion 413, which is in contact with the inner peripheral surface of the bore portion 52 while being urged by the elastic force of the elastic piece 412, is moved in the direction toward the base end side. When reaching the position of the opening 57, the locking portion 413 is inserted in the opening 57 (see FIG. 27). In this state, even if the pressing force of the chip 13, which force is applied to the plunger 41 in the direction toward the base end side, is released, the movement of the plunger 41 in the direction toward the tip side is restricted by locking of the locking portion 413 with the opening 57. At this time, the coil spring 42 is in the compression state. The preparation of puncturing the finger tip with the puncturing means 4 and the preparation of sampling blood (specimen) are thus accomplished.

[2] The power switch (not shown) is turned on, to activate the constituent elements of the body fluid component measuring apparatus 1, thereby bringing them into measurable states. In this state, the electromagnetic valve 26 remains closed.

[3] The finger tip (finger) 200 is touched to the touch portion 3, so that the finger tip 200 is brought into press-contact with the contact portion 163 of the chip 13. At this time, the tip opening 162 may be blocked with the finger tip 200 in such a manner as to make the leakage of air as small as possible (see FIG. 28).

[4] The operating button 222 is depressed, to operate the body fluid component measuring apparatus 1, thereby executing a program shown in FIG. 32.

The surface of the finger tip 200 is first punctured with the needle body 141 of the puncture needle 14 (step S407 in FIG. 32).

To be more specific, when it is decided that the pressure has been sufficiently reduced, the control means 11 outputs a signal for applying a current to a coil of the solenoid 28. The plunger 281 of the solenoid 28 thus energized is moved in the direction shown by the arrow in FIG. 27, to be brought into contact with the locking portion 413, whereby the locking portion 413 is pushed down in the bore portion 52 by the plunger 281. As a result, the locking of the locking portion 413 is released, so that the plunger 41 is moved in the direction toward the tip side by the elastic force of the compressed coil spring 42. Along with the movement of the plunger 41, the needle body 141 projects from the tip opening 162, to puncture the surface of the finger tip 200 (see FIG. 29). Blood flows out of the puncture site 210 punctured by the needle body 141.

After the finger tip 200 is punctured by the needle body 141, the plunger 41 is pushed back in the direction toward the base end side by the elastic force of the coil spring 43. The movement of the plunger 41 is attenuated, and finally the plunger 41 is rested at the position where the elastic force of the coil spring 43 is balanced against the elastic force of the coil spring 42 (see FIG. 30). At this time, the edge of the needle body 141 is in the state being housed in the chip 13. In this way, the cutting edge of the needle body 141 does not project from the tip opening 162 except that it is used for puncture of the finger tip, to thereby eliminate erroneous damages of the skin of the finger tip and preventing infection via the needle body 141. The body fluid component measuring apparatus 1 is thus advantageous in carrying out the sampling of blood with a high safety.

The control means 11 then starts the control of drive of the pump 8 and the electromagnetic valve 26 (step S402 in FIG. 32).

To be more specific, the control means 11 controls the drive of the pump 8 and the electromagnetic valve 26 in such a manner as to alternately change the pressure in the bore portion 52 (including the interior of the chip 13) between the first pressure P1 and the second pressure P2 as shown in FIG. 33. It is to be noted that the pressure at a portion, in the vicinity of the puncture site 210 punctured by the needle body 141, of the finger tip 200 is fluctuated along with the fluctuation of the pressure in the bore portion 52.

In this case, first, in a state that the electromagnetic valve 26 is closed, the pump 8 is operated to suck air in the bore portion 52 until the pressure in the bore portion 52 is reduced to the first pressure P1, and to keep the pressure in the bore portion 52 at the first pressure P1 for a specific time.

The pump 8 is then stopped, and the electromagnetic valve 26 is opened to discharge air in the bore portion 52 until the pressure in the bore portion 52 is reduced to the second pressure P2, and to keep the pressure in the bore portion 52 at the second pressure P2 for a specific time. Such an operation is then repeated.

Figure 30:
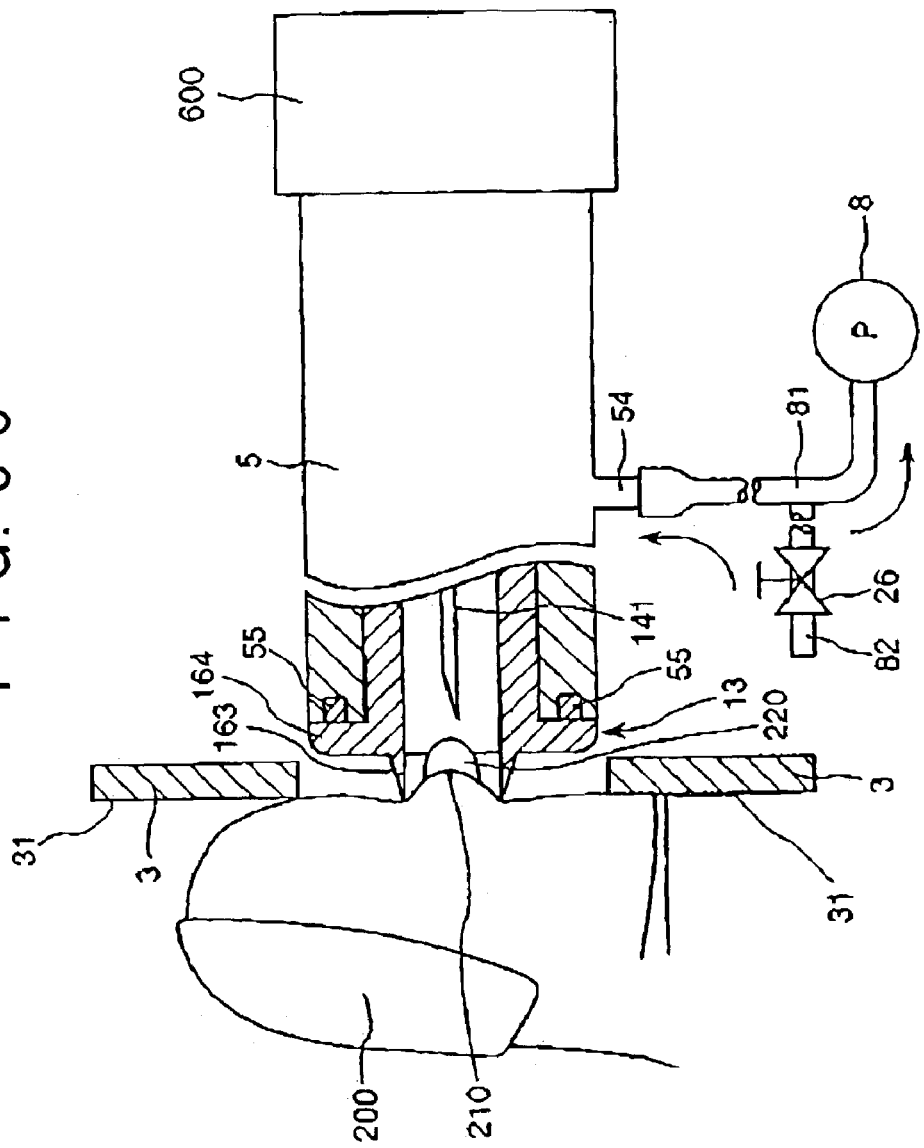
FIG. 30 is a vertical sectional view showing the configuration example of the essential portions of the body fluid component measuring apparatus according to the first embodiment of the third aspect of the present invention (in a state after puncture and at the time of operation of the pressure adjusting means)

As a result, the blood 220 is sucked from the puncture site 210 (see FIG. 30). In particular, as compared with a case where the pressure in the bore portion 52 is kept constant, a necessary amount of blood can be certainly sampled for a short time.

As described above, according to the body fluid component measuring apparatus 1, the puncturing operation and the evacuation operation are performed by only one depressing operation of the operating button 222, and the evacuation releasing operation (to be described later) is automatically performed. Accordingly, the apparatus 1 is very excellent in operability.

[5] The blood 220 raised in a granular shape from the puncture site 210 as a result of the operation described in the item [4] is sucked in the chip 13, to be brought into contact with the blood introducing guide 166 formed in the chip 13. The blood 220 is then introduced to the test paper 18 via the blood passage 19, being supplied to the center portion of the test paper 18, and is diffused radially in the test paper 18 (see FIG. 2).

Along with the supply and diffusion of the blood 220 on and in the test paper 18, glucose (component to be measured) in the blood 220 reacts with the reagent supported by the test paper 18, with a result that the test paper 18 is colored to a degree depending on the amount of glucose.

On the other hand, after executing step S402 shown in FIG. 32, the control means 11 drives the measuring means 7, to monitor the coloring of the test paper 18 via the measuring means 7, thereby deciding whether or not the blood has been sampled (step S403 in FIG. 32).

In step S403, if the voltage level of a signal inputted from the light receiving device 72 of the measuring means 7 is more than a predetermined threshold value, it is decided that the blood has been sampled, and if the voltage level of the above signal is equal to or less than the threshold value, it is decided that the blood has been not sampled.

The threshold value is set to a value sufficiently larger than a voltage level of the signal before coloring of the test paper 18 and sufficiently smaller than a voltage level of the signal at the time of coloring of the test paper 18.

If it is decided in step S403 that the blood has been not sampled, it is decided whether or not the predetermined time has elapsed (step S404 in FIG. 32).

If it is decided in step S404 that the predetermined time has not elapsed, the process is returned to step S403, and steps S403 and S404 are executed again. At this time, if it is decided in step S404 that the predetermined time has elapsed, error processing is performed (step S405 in FIG. 32).

In step S405, the pump 8 is stopped and the electromagnetic valve 26 is opened to release the evacuation state, and further, the notice that an error has occurred during operation is given in the form of written words displayed on the display unit 12 or in the form of audio words outputted from the audio outputting unit 32. It is to be noted that the notice may be of course given via both the display unit 12 and the audio outputting unit 32.

Such a notice about an error allows the operator (user) to comprehend that an error (trouble) has occurred during operation.

If it is decided in step S403 that the blood has been sampled, the pump 8 is stopped (step S406 in FIG. 32).

The electromagnetic valve 26 is opened to release the evacuation state of the bore portion 52 (including the interior of the chip 13) (step S407 in FIG. 32).

When the electromagnetic valve 26 is opened, outside air (atmospheric air) flows in the bore portion 52 (including the interior of the chip 13) and the puncture site 210 via the tubes 82, 81 and the ventilation passage 54, whereby the pressure in the bore portion 52 (including the interior of the chip 13) and the puncture site 210 is returned to atmospheric air (see FIG. 31).

When the operator becomes insensible of suction at the portion, around the puncture site 210, of the finger tip 200 and thereby recognizes that the internal pressure is returned to atmospheric pressure, he or she separates the finger tip 200 from the contact portion 163 of the chip 13.

After executing step S407 shown in FIG. 32, the control means 11 causes the measuring means 7 to measure the degree of coloring of the test paper 18, executes arithmetic operation based on the data thus obtained, and performs correcting calculation such as temperature correcting calculation or hematocrit value correcting calculation, to quantify the blood sugar level (step S408 in FIG. 32).

In this case, since the evacuation state of the bore portion 52 (including the interior of the chip 13), that is, the evacuation state of the housing space of the test paper 18 is released, a component (for example, oxygen, carbon dioxide, or water vapor) in atmospheric air necessary for reaction between glucose (component to be measured) in the blood 220 and the reagent supported by the test paper 18 can be sufficiently supplied to the test paper 18, whereby the blood sugar level can be accurately measured.

The blood sugar level thus calculated is displayed on the display unit 12 (step S409 in FIG. 32).

The operator can thus confirm his or her blood sugar level from the value displayed on the display unit 12.

In addition, after the evacuation state is released in step S407, the electromagnetic valve 26 is closed again for the next measurement.

As described above, according to the body fluid component measuring apparatus 1, it is possible to certainly sample a sufficient amount of blood necessary for measurement for a short time and to accurately, certainly measure the blood sugar level (amount of a specific component in blood).

Since the test paper 18 is provided on the chip 13, it is possible to continuously perform the puncture of the finger tip, sampling of blood, diffusion of blood in the test paper 18, and measurement (quantitative determination) of blood, and hence to easily measure the blood sugar level (component) in blood for a short time.

Since the preparation for operating the body fluid component measuring apparatus 1 is facilitated, the apparatus 1 is advantageous for periodical or repeated use thereof.

According to the body fluid component measuring apparatus 1, it is possible to prevent occurrence of an accident such as erroneous puncture of the skin of the operator again after puncture necessary for sampling of blood, and hence to sample blood with a high safety. The apparatus 1 is also advantageous in that the operator can use the apparatus 1 with less sensation of fear against puncture because the puncture needle 14 is out of the eyeshot of the operator.

Accordingly, the body fluid component measuring apparatus 1 is suitable for the operator (patient) to measure his or her blood sugar level.

The body fluid component measuring apparatus 1 is advantageous in terms of simple configuration, small size and light weight, low cost, and suitability for mass-production.

As shown in FIG. 33, according to this embodiment, the puncture is performed before the operation of the pump 8 is started (at a time point t1); however, according to the present invention, the puncture may be performed nearly simultaneously with the operation of the pump 8 (at a time point t2), or the puncture may be performed after the operation of the pump 8 is started (at a time point t3). In other words, according to the present invention, the puncture may be performed when the pressure in the bore portion 52 (including the interior of the chip 13) is equal to either atmospheric pressure or the first pressure P1.

A second embodiment of the body fluid component measuring apparatus of the present invention will be described below.

Figure 34:
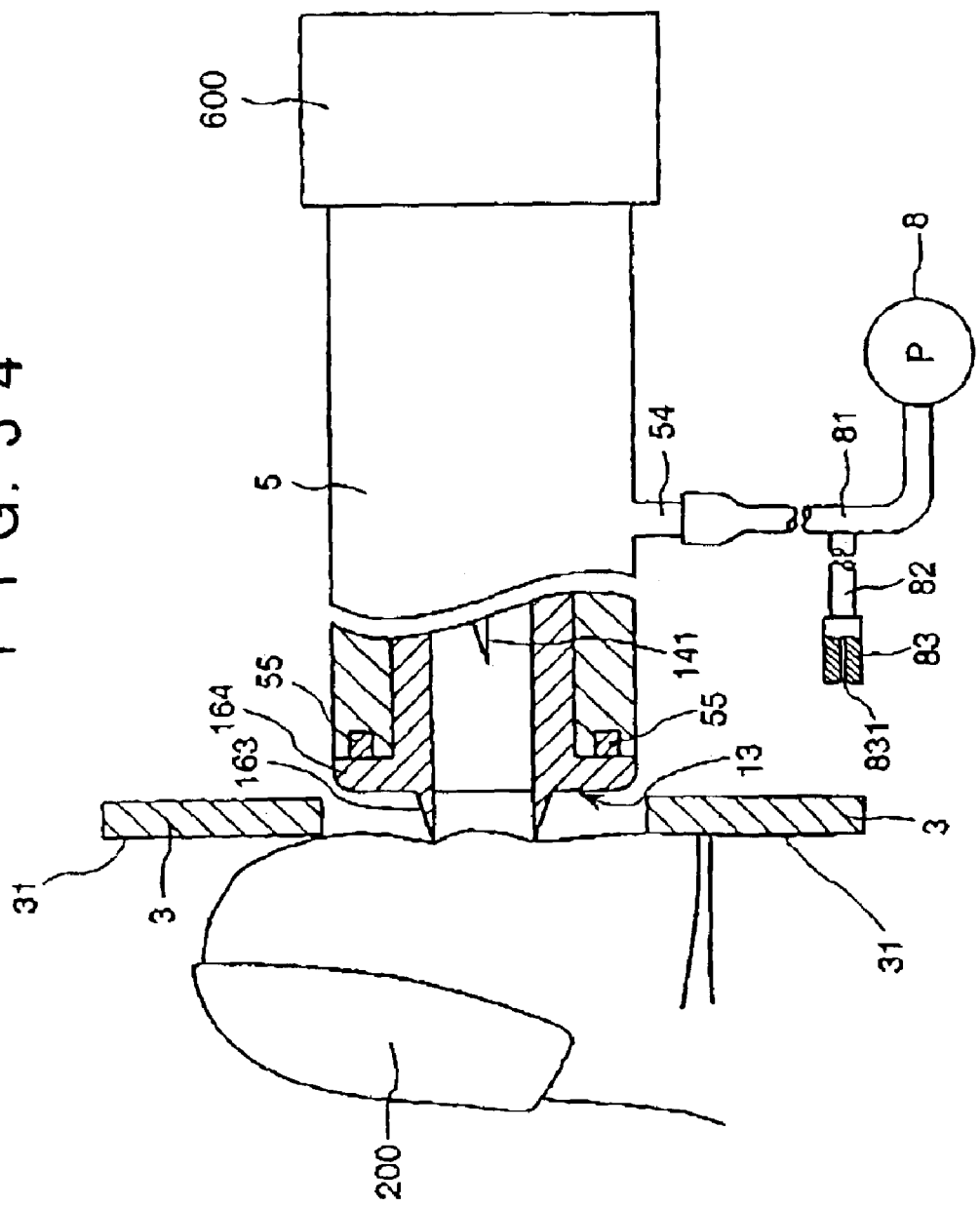
FIG. 34 is a vertical perspective view showing essential portions of a second embodiment of a body fluid component measuring apparatus according to the third aspect of the present invention.

FIG. 34 is a vertical sectional view showing configuration examples of essential portions of the second embodiment of the body fluid component measuring apparatus according to the present invention. The following description will be made, principally, about different points from the above-described body fluid component measuring apparatus 1 according to the first embodiment, with the common points thereto omitted. It is to be noted that FIG. 34 is depicted with the "base end side" of the apparatus taken as the right side and the "tip side" of the apparatus taken as the left side.

The body fluid component measuring apparatus 1 according to the second embodiment is different from the body fluid component measuring apparatus 1 according to the first embodiment in configuration of the pressure adjusting means.

In this body fluid component measuring apparatus 1, as shown in FIG. 34, a fine tube 83 is provided in place of the electromagnetic valve 26 of the body fluid component measuring apparatus 1 according to the first embodiment.

The fine tube 83 is formed of a cylindrical member and internally has an orifice (flow passage) 831. The fine tube 83 is connected to an end portion of the tube 82, and the tip of the fine tube 83 (orifice 831) is opened to the outside of the main body 2.

The orifice 831 of the fine tube 83 is required to be narrow enough to keep a large passing resistance of air. The diameter of the orifice 831 is not particularly limited but is preferably in a range of about 0.01 to 0.3 mm. The length of the orifice 831 is not particularly limited but is preferably in a range of about 5 to 15 mm. By setting the diameter of the orifice 831 within the above range, it is possible to certainly keep the necessary passing (flow) resistance of air.

An evacuation releasing means is composed of the tubes (flow passage) 81, 82 and the fine tube 83. The pressure adjusting means is composed of the evacuation releasing means and the pump 8.

It is to be noted that the fine tube 83 is not limited to that shown in the figure, and although only one fine tube 83 is provided in this embodiment, a plurality of fine tubes (orifices) may be provided if needed.

According to the body fluid component measuring apparatus 1, at the time of sampling blood from the puncture site, the drive of the pump 8 and the electromagnetic valve 26 is controlled, on the basis of information supplied from the pressure sensor 27, in such a manner as to evacuate the bore portion 52 (including the interior of the chip 13) with the pressure fluctuated (changed) with elapsed time.

The pressure pattern in the bore portion 52 at the time of sampling blood is not particularly limited insofar as the bore portion 52 is evacuated with the pressure fluctuated with elapsed time. One example of the pressure pattern in the bore portion will be described below.

Figure 35:
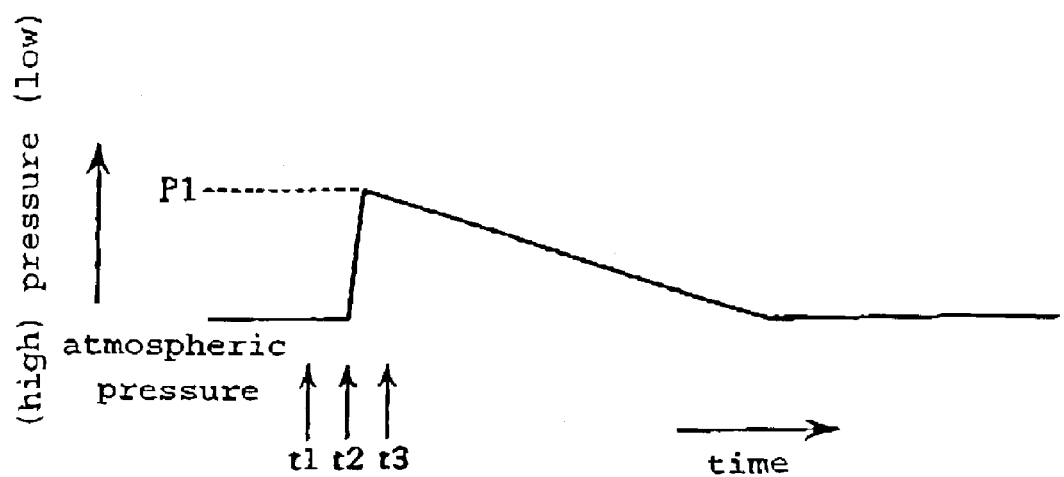
FIG. 35 is a graph showing a pressure pattern in a puncture needle housing space (bore portion 52) at the time of sampling blood in the body fluid component measuring apparatus according to the second embodiment of the third aspect of the present invention.

FIG. 35 is a graph showing one example of the pressure pattern in the bore portion 52 at the time of sampling blood.

As shown in the figure, according to the body fluid component measuring apparatus 1, at the time of sampling blood, the drive of the pump 8 is controlled in such a manner as to reduce the pressure in the bore portion 52 once to the first pressure P1 lower than atmospheric pressure and then gradually increase the pressure in the bore portion 52.

As a result, it is possible to certainly sample an amount, necessary and adequate for measurement, of blood for a short time.

The first pressure P1 is preferably set in a range of about 300 to 600 mmHg, more preferably, in a range of about 400 to 600 mmHg.

As a result, it is possible to more certainly sample an amount, necessary and adequate for measurement, of blood for a shorter time.

The increasing rate (pressure intensifying rate) of the pressure in the bore portion 52 from the first pressure P1 is preferably set in a range of about 100 to 300 mmHg/sec, more preferably, in a range of about 200 to 250 mmHg/sec.

As a result, it is possible to more certainly sample an amount, necessary and adequate for measurement, of blood for a shorter time.

The pressure intensifying rate may be arbitrarily set by, for example, adjusting the number of the fine tubes 83, the number of the orifices 831, and the diameter of each orifice 831.

According to the body fluid component measuring apparatus 1, since the flow rate of air sucked by operating the pump 8 is larger than the flow rate of outside air (atmospheric air) flowing from the orifice 831 of the fine tube 83, the air in the bore portion 52 of the housing 5 is sucked by operating the pump 8. As a result, the pressure in the bore portion 52 (including the interior of the chip 13) is reduced to the first pressure P1, and therefore, the bore portion 52 (including the interior of the chip 13) is brought into an evacuation state.

When the pump 8 is stopped, outside air (atmospheric air) flows in the bore portion 52 (including the interior of the chip 13) via the orifice 831 of the fine tube 83, the tubes 82 and 81, and the ventilation passage 54, so that the pressure in the bore portion 52 (including the interior of the chip 13) is gradually increased from the first pressure P1. As a result, the evacuation state of the bore portion 52 (including the interior of the chip 13) and the puncture site 210 is released.

In other words, the pressure in the bore portion 52 (including the interior of the chip 13) and around the puncture site 210 is returned to atmospheric pressure.

As shown in FIG. 35, the puncture may be performed before the start of operation of the pump 8 (at a time point t1), nearly simultaneously with operation of the pump 8 (at a time point t2), or after the start of operation of the pump 8 (at a time point t3). In other words, the puncture may be performed when the bore portion 52 (including the interior of the chip 13) is either in the atmospheric pressure state or in the evacuation state.

The pressure increasing rate (pressure intensifying rate) of the pressure in the bore portion 52 from the first pressure P1 may be kept constant or fluctuated (changed) with elapsed time.

According to the body fluid component measuring apparatus 1, the cycle (shown in FIG. 35) of reducing the pressure in the core portion 52 once to the first pressure P1 lower than atmospheric pressure and then gradually increasing the pressure in the bore portion 52 may be performed by only one time or repeated by a plurality of times.

The body fluid component measuring apparatus 1 according to this embodiment can obtain the same effect as that obtained by the above-described body fluid component measuring apparatus 1 according to the first embodiment.

While the body fluid component measuring apparatus according to the third aspect of the present invention has been described on the basis of the first and second embodiments shown in the figures, the present invention is not limited thereto. For example, the configuration of each of the constituent elements described in the embodiments may be replaced with any configuration exhibiting the same function.

According to the present invention, the specific configurations of the above-described embodiments may be appropriately combined with each other.

In the above-described embodiments according to the second aspect, the body fluid to be sampled is represented by blood; however, according to the present invention, the body fluid to be sampled is not limited thereto but may be exemplified by sweat, lymph, cerebrospinal fluid, or the like.

The component to be measured is represented by glucose (blood sugar level) in the embodiments; however, according to the present invention, the component to be measured is not limited thereto but may be exemplified by protein, cholesterol, uric acid, creatinine, alcohol, or ions of an inorganic matter such as sodium.

The measuring means in the embodiments is configured to measure an amount of a specific component; however, according to the present invention, the measuring means may be configured to measure a property of a specific component, or to measure both an amount and a property of a specific component.

The means (called "measuring means") used as not only as the blood sampling detecting means for detecting the sampling of blood but also as the measuring means for measuring an amount of a specific component in blood is provided in the embodiments; however, according to the present invention, the blood sampling detecting means and the measuring means may be separately provided.

The blood sampling means is represented by the means for optically detecting the sampling of blood in the embodiments; however, according to the present invention, the blood sampling means is not limited thereto but may be configured as a means for electrically detecting the sampling of blood.

In the case of adopting the blood sampling detecting means for optically detecting the sampling of blood, the detection of the sampling of blood is not necessarily based on the manner described in the embodiments, that is, the manner of detecting the coloring (color development) of the test paper due to reaction between the component in blood and the reagent but may be based on a manner of detecting the introduction of blood in the blood passage (blood flow passage) for supplying blood to the test paper provided on the chip.

In the case of adopting the manner of detecting the introduction of blood in the blood passage, a portion, at least in the vicinity of the blood passage, of the chip may be formed of a member having a light permeability (transparency), and further, the blood sampling detecting means may be configured to emit light to the blood passage via the transparent member, receive the reflected light or transmitted light, and convert the light into an electric signal, and the control means may be configured to monitor a voltage outputted from the blood sampling detecting means. If blood is introduced in the blood passage, the color of a portion, through which the blood passes, of the blood passage is changed into nearly dark-red, to change the quantity of the reflected light or the transmitted light thereat, thereby changing a voltage outputted from the blood sampling detecting means. As a result, the sampling of blood can be detected on the basis of the change in voltage (quantity of light) outputted from the blood sampling detecting means.

The blood sampling detecting means for electrically detecting the sampling of blood is exemplified by a sensor (electrode) for detecting (measuring) an impedance of the blood passage or the like of the chip, or a bio-sensor.

In the case of adopting the bio-sensor, since a current outputted from the bio-sensor is changed if blood is introduced in the blood passage, the sampling of blood can be detected on the basis of the change in current (current value) outputted from the bio-sensor.

In the case of adopting the sensor for detecting an impedance of the blood passage, since an impedance between the electrodes of the sensor, provided across the blood passage, is changed if blood is introduced in the blood passage, the sampling of blood can be detected on the basis of the change in impedance of the blood passage.

The body fluid component measuring apparatus in each of the embodiments is configured by optically measuring the degree of the coloring of the test paper caused by reaction between the component in blood and the reagent, and converting the measured result into a value to be displayed on the display unit; however, the present invention is not limited thereto. For example, the measuring apparatus may be configured by electrically measuring a change in potential caused depending on an amount of a component in blood (specimen), and converting the measured result into a value to be displayed on the display unit.

The measurement method in each of the embodiments is configured so as to release the evacuation state prior to measurement; however, according to the present invention, the method may be configured so as to relieve the evacuation state prior to measurement.

According to the present invention, the operation of the puncturing means and the pressure adjusting means may be started either in a manual manner or automatic manner.

According to the present invention, a chip withdrawing mechanism for moving the housing 5 and the chip 13 mounted thereto in the direction apart from the finger (toward the base end side) may be provided. The chip withdrawing mechanism may be the same as the chip withdrawing mechanism 61 described in each of the embodiments according to the first or second aspect.

According to the present invention, the body fluid component measuring apparatus in the first aspect may include the pressure detecting means and the notifying means specified in the second aspect and/or the pressure adjusting means specified in the item (25) in the third aspect.

Each of these means added to the first aspect is the same as that described in each of the embodiments in the second and third aspects, and therefore, the overlapped description thereof is omitted.

To be brief, the body fluid component measuring apparatus according to the first aspect may be configured to include the pressure detecting means for detecting the pressure in the housing space and the notifying means for notifying specific information, wherein the pressure in the housing space be reduced by the evacuating means and a notice be given to an operator (user) on the basis of the information from the pressure detecting means by the notifying means.

Alternatively, the body fluid component measuring means according to the first aspect may be configured to include the pressure adjusting means for adjusting the pressure in the puncture needle housing space.

The body fluid component measuring apparatus according to the first aspect, which is configured to include the pressure detecting means for detecting the pressure in the housing space and the notifying means for notifying specific information, wherein the pressure in the housing space be reduced by the evacuating means and a notice be given to an operator (user) on the basis of the information from the pressure detecting means by the notifying means, may further include the pressure adjusting means for adjusting the pressure in the puncture needle housing space.

INDUSTRIAL APPLICABILITY

As described above, according to the present invention, it is possible to provide a body fluid component measuring apparatus capable of accurately and certainly measuring, at the time of sampling a body fluid (for example, at the time of sampling blood from a puncture site), a specific component in the body fluid (for example, blood) for a short time.

In particular, it is possible to prevent an epidermis of a patient from being uselessly punctured, thereby reducing the burden of the patient.

In the case of the body fluid component measuring apparatus having a pressure adjusting means, since a space (for example, a puncture needle housing space) is evacuated with the pressure fluctuated with elapsed time, it is possible to certainly sample an amount, necessary and adequate for measurement, of blood for a short time, and hence to certainly measure a specific component in the blood for a short time.

In the case of the body fluid component measuring apparatus in which a strip of test paper is provided on a chip, it is possible to continuously perform the puncture of a finger, the sampling of blood, the diffusion of the blood in the test paper, and the measurement (quantitative determination) of a specific component in the blood, and hence to easily perform the measurement of a body fluid for a short time.

Since the preparation for operating the body fluid component measuring apparatus is easy, the apparatus is advantageous for periodical or repeated use thereof.

According to the body fluid component measuring apparatus, it is possible to prevent an accident such as erroneous puncture of the skin of a patient again after puncture for sampling blood, and hence to sample blood with a high safety. The apparatus is also advantageous in that a patient can use the apparatus with less sensation of fear against puncture because the puncture needle is out of the eyeshot of the patient.

The body fluid component measuring apparatus of the present invention, therefore, is suitable for a patient to measure his or her blood sugar level or the like.

The body fluid component measuring apparatus of the present invention is also advantageous in terms of simple configuration, small size and light weight, low cost, and suitability for mass-production.

What is claimed is:

1. A combination of a body fluid component measuring apparatus and a chip adapted to be mounted thereto, said chip comprising a chip housing, a puncture needle and a strip of test paper disposed on said chip housing, said chip housing possessing a contact portion at a tip side thereof, and said contact portion internally possessing a tip opening, said body fluid component measuring apparatus comprising:
   a touch portion to which an epidermis to be punctured is touched;
   a housing space for holding said chip;
   puncturing means for operating said puncture needle when said chip is mounted to said apparatus so as to puncture the epidermis touched to said touch portion;
   evacuating means for evacuating a puncture site of the epidermis to be punctured by said puncture needle as well as the housing space;
   measuring means for measuring an amount of a specific component of a body fluid sampled from the puncture site and diffused in said test paper;
   body fluid sampling detecting means for detecting the sampling of the body fluid; and
   evacuation releasing means for releasing or relieving the evacuation state of at least said housing space;
   wherein when the sampling of the body fluid is detected by said body fluid sampling detecting means, the evacuation state of at least said housing space is released or relieved, and then the amount of the specific component in the sampled body fluid is measured by said measuring means.

2. The combination of the body fluid component measuring apparatus and the chip according to claim 1, wherein the measurement of the amount of the specific component in the body fluid requires a specific component in atmospheric air.

3. The combination of the body fluid component measuring apparatus and the chip according to claim 1, wherein said evacuation releasing means has a flow passage for communicating said housing space to the outside and a valve for opening/closing said flow passage.

4. The combination of the body fluid component measuring apparatus and the chip according to claim 1, wherein said evacuation releasing means has a flow passage for communicating said housing space to the outside, and at least part of said flow passage has a portion in which an air passing resistance is relatively high.

5. The combination of the body fluid component measuring apparatus and the chip according to claim 1, wherein a component forming at least part of said measuring means also forms at least part of said body fluid sampling detecting means.

6. The combination of the body fluid component measuring apparatus and the chip according to claim 1, the body fluid component measuring apparatus further comprising an apparatus housing which houses said puncturing means, said housing space being provided at said apparatus housing wherein said evacuating means brings said housing space in said housing into an evacuation state.

7. The combination of the body fluid component measuring apparatus and the chip according to claim 6, wherein said evacuation releasing means releases or relives the evacuation state of said housing space in said apparatus housing.

8. The combination of the body fluid component measuring apparatus and the chip apparatus according to claim 1, wherein the operation of said puncturing means and the operation of said evacuating means are allowed to be nearly simultaneously started.

9. The combination of the body fluid component measuring apparatus and the chip according to claim 1, wherein said test paper is specialized for measurement of a blood sugar level.

10. The combination of the body fluid component measuring apparatus and the chip according to claim 1, the body fluid component measuring apparatus further comprising:
   pressure detecting means for detecting the pressure in said housing space; and
   notifying means for notifying specific information;
   wherein upon operation of said evacuating means to evacuate said housing space, a notice based on the information from said pressure detecting means is outputted by said notifying means.

11. The combination of the body fluid component measuring apparatus and the chip according to claim 1, the body fluid component measuring apparatus further comprising:
   pressure adjusting means for adjusting the pressure in said housing space;
   wherein at the time of sampling the body fluid from the puncture site, said housing space is evacuated by said pressure adjusting means with the pressure fluctuated with elapsed time.

12. A combination of a body fluid component measuring apparatus and a chip adapted to be mounted thereto for sampling a body fluid via an epidermis and measuring a component of the body fluid,
   said chip comprising:
      a housing;
      a puncture needle; and
      a strip of test paper disposed on said housing;
      said housing possessing a contact portion at a tip side thereof, and said contact portion internally possessing a tip opening,
   said body fluid component measuring apparatus comprising:
      a touch portion to which the epidermis is touched;
      a housing space for holding said chip air-tightly sealed with the epidermis touched to said touch portion;
      evacuating means for evacuating said space;
      measuring means for measuring an amount and/or a property of a specific component in the body fluid sampled in said space;
      pressure detecting means for detecting the pressure in said space; and
      notifying means for notifying specific information;
      wherein upon operation of said evacuating means to evacuate said space, a notice based on the information from said pressure detecting means is outputted by said notifying means.

13. The combination of the body fluid component measuring apparatus and the chip according to claim 12, wherein said body fluid component measuring apparatus comprises puncturing means for operating said puncture needle when said chip is mounted to said apparatus so as to puncture the epidermis touched to said touch portion.

14. A combination of a body fluid component measuring apparatus and a chip adapted to be mounted thereto, said chip comprising a housing, a puncture needle and a strip of test paper disposed on said housing, said housing possessing a contact portion at a tip side hereof, and said contact portion internally possessing a tip opening, said body fluid component measuring apparatus comprising:

a touch portion to which an epidermis is touched;

puncturing means for operating said puncture needle when said chip is mounted to said apparatus so as to puncture the epidermis touched to said touch portion;

evacuating means for evacuating the puncture site of the epidermis to be punctured by said puncture needle as well as a housing space of said body fluid component measuring apparatus;

pressure detecting means for detecting the pressure in said housing space;

measuring means for measuring an amount of a specific component in the body fluid sampled from the puncture site; and notifying means for notifying specific information;

wherein upon operation of said evacuating means to evacuate said housing space, a notice based on the information from said pressure detecting means is outputted by said notifying means.

15. The combination of the body fluid component measuring apparatus and the chip according to claim 14, wherein when the evacuation state of said housing space is detected by said pressure detecting means, said puncture needle is operated by said puncturing means.

16. The combination of the body fluid component measuring apparatus and the chip according to claim 15, the body fluid component measuring apparatus further comprising:

operation starting means including an electrical drive source, said means being used for starting the operation of said puncturing means by drive of said drive source;

wherein the evacuation state of said housing space is detected by said pressure detecting means, the operation of said puncturing means is started by said operation starting means and said puncture needle is operated by said puncturing means.

17. The combination of the body fluid component measuring apparatus and the chip according to claim 14, wherein said puncturing means has a plunger and an urging member for urging said plunger in the direction toward the touch portion.

18. The combination of the body fluid component measuring apparatus and the chip according to claim 17, wherein said plunger has a locking portion for restricting the movement of said plunger in the direction toward the touch portion, and when the locking of said locking portion is released in the state that the plunger remains urged by said urging member, said plunger is moved in the direction toward the touch portion to allow said puncture needle to puncture the epidermis.

19. The combination of the body fluid component measuring apparatus and the chip according to claim 18, further comprising operation starting means including an electrical drive source, said means being used for releasing the locking of said locking portion by drive of said drive source;

wherein when the evacuation state of said housing space is detected by said pressure detecting means, the locking of said locking portion is released by said operation starting means.

20. The combination of the body fluid component measuring apparatus and the chip according to claim 14, wherein when the evacuation state of said housing space is detected by said pressure detecting means, the evacuation state is once released, and then the puncture is performed and the puncture site of the finger punctured by said puncture needle as well as said housing space for housing said puncture needle are evacuated.

21. A body fluid component measuring apparatus used with a chip mounted thereto, said chip including a puncture needle, said apparatus comprising:

a touch portion to which an epidermis to be punctured is touched;

puncturing means for operating said puncture needle so as to puncture the epidermis touched to said touch portion;

evacuating means for evacuating the puncture site of the epidermis to be punctured by said puncture needle as well as a housing space for housing said puncture needle;

pressure detecting means for detecting the pressure in said housing space;

measuring means for measuring an amount of a specific component in the body fluid sampled from the puncture site; and notifying means for notifying specific information;

wherein when said evacuating means is operated and the pressure in said housing space as determined by the detecting means is not sufficiently reduced, a notice about an error is outputted by said notifying means.

22. The combination of the body fluid component measuring apparatus and the chip according to claim 21, wherein when an evacuation state of said housing space is detected by said pressure detecting means, said puncture needle is operated by said puncturing means.

23. The combination of the body fluid component measuring apparatus and the chip according to claim 22, the body fluid component measuring apparatus further comprising:

operation starting means including an electrical drive source, said means being used for starting the operation of said puncturing means by drive of said drive source;

wherein the evacuation state of said housing space is detected by said pressure detecting means, the operation of said puncturing means is started by said operation starting means and said puncture needle is operated by said puncturing means.

24. The combination of the body fluid component measuring apparatus and the chip according to claim 21, wherein said puncturing means has a plunger and an urging member for urging said plunger in the direction toward the touch portion.

25. The combination of the body fluid component measuring apparatus and the chip according to claim 24, wherein said plunger has a locking portion for restricting the movement of said plunger in the direction toward the touch portion, and when the locking of said locking portion is released in the state that the plunger remains urged by said urging member, said plunger is moved in the direction toward the touch portion to allow said puncture needed to puncture the epidermis.

26. The combination of the body fluid component measuring apparatus and the chip according to claim 25, the body fluid component measuring apparatus further comprising operation starting means including an electrical drive source, said means being used for releasing the locking of said locking portion by drive of said drive source;
wherein when the evacuation state of said housing space is detected by said pressure detecting means, the locking of said locking portion is released by said operation starting means.

27. The combination of the body fluid component measuring apparatus and the chip according to claim 21, wherein when an evacuation state of said housing space is detected by said pressure detecting means, the evacuation state is once released, and then the puncture is performed and the puncture site of the finger punctured by said puncture needle as well as said housing space are evacuated.

28. A body fluid component measuring apparatus used with a chip mounted thereto, said chip including a puncture needle, said apparatus comprising:
a touch portion to which an epidermis to be punctured is touched;
puncturing means for operating said puncture needle so as to puncture the epidermis touched to said touch portion;
evacuating means for evacuating a puncture site of the epidermis to be punctured by said puncture needle as well as a housing space for housing said puncture needle;
pressure detecting means for detecting the pressure in said housing space;
measuring means for measuring an amount of a specific component in a body fluid sampled from the puncture site;
notifying means for notifying specific information;
wherein when said evacuating means is operated and the pressure in said housing space as determined by the detecting means is not sufficiently reduced, a notice to correct the position of the epidermis touched to said touch portion is outputted by said notifying means, and when the evacuation state of said housing space is not detected by said pressure detecting means even after a specific time has elapsed, a notice about an error is outputted by said notifying means.

29. A combination of a body fluid component measuring apparatus and a chip adapted to be mounted thereto, said chip comprising a housing, a puncture needle and a strip of test paper disposed on said housing, said housing possessing a contact portion at a tip side thereof, and said contact portion internally possessing a tip opening, said body fluid component measuring apparatus comprising:
a touch portion to which an epidermis to be punctured is touched;
puncturing means for operating said puncture needle when said chip is mounted to said apparatus so as to puncture the epidermis touched to said touch portion;
evacuating means for evacuating a puncture site of the epidermis to be punctured by said puncture needle as well as a housing space for housing said chip;
pressure detecting means for detecting the pressure in said housing space; and
measuring means for measuring an amount of a specific component in a body fluid sampled from the puncture site;
wherein, when said evacuating means is operated and the pressure in said housing space as determined by the detecting means is sufficiently reduced, said puncture needle is operated by said puncturing means.

30. A combination of a body fluid component measuring apparatus and a chip adapted to be mounted thereto for sampling a body fluid via an epidermis and measuring a component of the body fluid,
said chip comprising:
a housing;
a puncture needle; and
a strip of test paper disposed on said housing;
said housing possessing a contact portion at a tip side thereof, and said contact portion internally possessing a tip opening,
said body fluid component measuring apparatus comprising:
a touch portion to which the epidermis is touched;
a housing space for holding said chip air-tightly sealed by the epidermis touched to said touch portion;
pressure adjusting means for adjusting the pressure in said space; and
measuring means for measuring an amount and/or a property of a specific component of the body fluid sampled in said space;
wherein at the time of sampling the body fluid in said space via the epidermis, said space is evacuated by said pressure adjusting means with the pressure fluctuated with elapsed time.

31. The combination of the body fluid component measuring apparatus and the chip according to claim 30, wherein said body fluid component measuring apparatus comprises puncturing means for operating said puncture needle when said chip is mounted to said apparatus so as to puncture the epidermis touched to said touch portion.

32. A combination of a body fluid component measuring apparatus and a chip adopted to be mounted thereto, said chip comprising a puncture needle, said body fluid component measuring apparatus comprising:
a touch portion to which an epidermis to be punctured is touched;
puncturing means for operating said puncture needle when said chip is mounted to said apparatus so as to puncture the epidermis touched to said touch portion;
pressure adjusting means for adjusting the pressure in a housing space for housing said chip; and
measuring means for measuring an amount of a specific component in a body fluid sampled from the puncture site;
wherein at the time of sampling the body fluid from the puncture site, at least one cycle of reducing the pressure in said housing space once to a first pressure lower than atmospheric pressure and then gradually increasing the pressure in said housing space is performed by said pressure adjusting means with the pressure fluctuated with elapsed time.

33. The combination of the body fluid component measuring apparatus and the chip according to claim 32, the body fluid component measuring apparatus further comprising:
pressure detecting means for detecting the pressure in said housing space;
wherein the pressure in said housing space is adjusted, on the basis of information from said pressure detecting means, by said pressure adjusting means.

34. The combination of the body fluid component measuring apparatus and the chip according to claim 32, wherein at the time of sampling the body fluid, the pressure in said housing space is alternately changed, by said pressure adjusting means, between a first pressure lower than atmospheric pressure and a second pressure higher than the first pressure.

35. The combination of the body fluid component measuring apparatus and the chip according to claim 34, wherein said second pressure is equal to or less than atmospheric pressure.

36. The combination of the body fluid component measuring apparatus and the chip according to claim 34, wherein a difference between said second pressure and said first pressure is in a range of 100 to 600 mmHg.

37. The combination of the body fluid component measuring apparatus and the chip according to claim 32, wherein a period of the pressure fluctuation is in a range of 1 to 30 sec.

38. The combination of the body fluid component measuring apparatus and the chip according to claim 32, wherein said first pressure is in a range of 100 to 600 mmHg.

* * * * *

UNITED STATES PATENT AND TRADEMARK OFFICE
CERTIFICATE OF CORRECTION

PATENT NO. : 7,207,952 B2
APPLICATION NO. : 10/333582
DATED : April 24, 2007
INVENTOR(S) : Masao Takinami et al.

It is certified that error appears in the above-identified patent and that said Letters Patent is hereby corrected as shown below:

On the face of the patent, Section 87 (PCT Pub. No.): change "WO02/07399" to --WO02/07599--.

Column 17, Line 66: change "mechanisms" to --mechanism--.

Column 17, Line 66: insert --6-- after the word "mechanism" (should read: ing mechanism 6 after the operation of the pump 8 can be . . .)

Column 28, Line 44: change "it" to --if-- (should read: correcting calculation if needed, to determine . . .)

Signed and Sealed this

Twenty-ninth Day of December, 2009

David J. Kappos
*Director of the United States Patent and Trademark Office*